(12) United States Patent
Rinsch et al.

(10) Patent No.: US 11,969,408 B2
(45) Date of Patent: *Apr. 30, 2024

(54) METHOD FOR IMPROVING MITOPHAGY IN SUBJECTS

(71) Applicant: Amazentis SA, Ecublens (CH)

(72) Inventors: Christopher Rinsch, Morges (CH); Penelope Andreux, Lausanne (CH); Anurag Singh, Ecublens (CH)

(73) Assignee: Amazentis SA, Lausanne (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/915,842

(22) Filed: Mar. 8, 2018

(65) Prior Publication Data

US 2018/0256539 A1    Sep. 13, 2018

(30) Foreign Application Priority Data

| Mar. 8, 2017 | (GB) | 1703736 |
| Apr. 25, 2017 | (GB) | 1706596 |
| May 16, 2017 | (GB) | 1707863 |

(51) Int. Cl.

| A61K 31/366 | (2006.01) |
| A61K 9/00 | (2006.01) |
| A61K 9/48 | (2006.01) |
| A61K 31/197 | (2006.01) |
| A61K 47/14 | (2017.01) |
| A61P 3/00 | (2006.01) |
| C07D 311/80 | (2006.01) |

(52) U.S. Cl.
CPC .......... *A61K 31/366* (2013.01); *A61K 9/0053* (2013.01); *A61K 9/4825* (2013.01); *A61K 9/4858* (2013.01); *A61K 31/197* (2013.01); *A61K 47/14* (2013.01); *A61P 3/00* (2018.01); *C07D 311/80* (2013.01)

(58) Field of Classification Search
CPC .. A61K 31/366; A61K 31/205; A61K 9/0053; A61K 9/4825; A61K 47/14; C07D 311/80; A61P 3/00
See application file for complete search history.

(56) References Cited

U.S. PATENT DOCUMENTS

| 6,133,311 | A | 10/2000 | Bok et al. |
| 6,440,436 | B1 | 8/2002 | Ghosal |
| 8,183,282 | B2 | 5/2012 | Seeram et al. |
| 8,894,993 | B2 | 11/2014 | Ghosal |
| 9,872,850 | B2 | 1/2018 | Rinsch et al. |
| 9,962,366 | B2 | 5/2018 | Rinsch et al. |
| 2003/0078212 | A1 | 4/2003 | Li et al. |
| 2005/0234031 | A1 | 10/2005 | Schrimpf et al. |
| 2005/0282781 | A1 | 12/2005 | Ghosal |
| 2007/0184136 | A1 | 8/2007 | Aviram |
| 2007/0197567 | A1 | 8/2007 | Sherris |
| 2008/0031862 | A1 | 2/2008 | Ghosal |
| 2008/0039179 | A1 | 2/2008 | Seelig et al. |
| 2008/0206275 | A1 | 8/2008 | Ramazanov et al. |
| 2008/0213401 | A1 | 9/2008 | Smith |
| 2009/0246300 | A1 | 10/2009 | Swilling |
| 2009/0326057 | A1 | 12/2009 | Seeram et al. |
| 2010/0004334 | A1 | 1/2010 | Jouni et al. |
| 2010/0021533 | A1 | 1/2010 | Mazed et al. |
| 2010/0055247 | A1 | 3/2010 | Tirrito |
| 2011/0263521 | A1 | 10/2011 | Moutet et al. |
| 2014/0018415 | A1 | 1/2014 | Rinsch et al. |

FOREIGN PATENT DOCUMENTS

| CN | 101301319 A | 11/2008 |
| CN | 103442594 | 12/2013 |
| EP | 2033526 A1 | 3/2009 |
| EP | 2068864 A2 | 6/2009 |
| JP | H02304080 A | 12/1990 |

(Continued)

OTHER PUBLICATIONS

Cecil Textbook of Medicine, 20th Edition, vol. 1, 1996.*

(Continued)

*Primary Examiner* — Shobha Kantamneni
(74) *Attorney, Agent, or Firm* — Foley Hoag LLP; Dana M. Gordon; Lawrence P. Tardibono

(57) ABSTRACT

The invention provides a compound of formula (I)

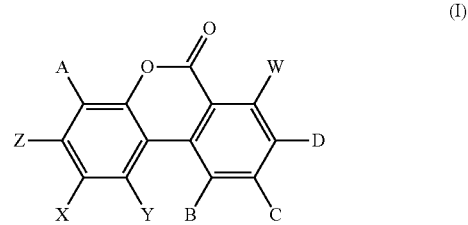

wherein:

A, B, C, D, W, X, Y and Z are each independently selected from H and OH;

or a salt thereof;

for use in the treatment and/or prophylaxis of a condition, disease or disorder in a subject, wherein the compound or salt is orally administered to a subject in a daily amount of from 2.8 to 6.6 mmol per day, over a period of at least 21 days. Also are provided are the compound of formula (I) for use in increasing mitophagy and/or autophagy, maintaining and/or improving muscle function and administration as a dietary, nutritional and/or health supplement.

19 Claims, 14 Drawing Sheets

(56) References Cited

FOREIGN PATENT DOCUMENTS

| | | |
|---|---|---|
| JP | 2008-503456 A | 2/2008 |
| JP | 2010-280627 A | 12/2010 |
| WO | WO-00/15044 A1 | 3/2000 |
| WO | WO-01/49281 A2 | 7/2001 |
| WO | WO-2002/094984 A2 | 11/2002 |
| WO | WO-2005/077899 A2 | 8/2005 |
| WO | WO-2005/097106 A1 | 10/2005 |
| WO | WO-2006/007310 A2 | 1/2006 |
| WO | WO-2006/127832 A2 | 11/2006 |
| WO | WO-2007/101247 A2 | 9/2007 |
| WO | WO-2007/127263 A2 | 11/2007 |
| WO | WO-2008/016554 A1 | 2/2008 |
| WO | WO-2007/133249 A3 | 2/2009 |
| WO | WO-2009/031023 A2 | 3/2009 |
| WO | WO-2009/120799 A2 | 10/2009 |
| WO | WO-2009/153652 A2 | 12/2009 |
| WO | WO-2011/011721 A2 | 1/2011 |
| WO | WO-2012/088519 A2 | 6/2012 |
| WO | WO-2012/113835 A1 | 8/2012 |
| WO | WO-2014004902 A2 | 1/2014 |
| WO | WO-2015/097231 A1 | 7/2015 |

OTHER PUBLICATIONS

Gura et al. (Science 1997).*
Johnson et al., (British J. of Cancer 2001).*
Merck Manual, 16th ed., 1992 p. 365-367, 413.*
Remington, The Science and Practice of Pharmacy, 19th Edition, 1995, pp. 1642-1646.*
"What Is Atherosclerosis?" NHLBI, National Institutes of Health (2016).
Abstract of unexamined Japanese application No. JP2010-280627 published Dec. 16, 2010.
Adams et al., "Pomegranate Ellagitannin-Derived Compounds Exhibit Antiproliferative and Antiaromatase Activity in Breast Cancer Cells In Vitro," Cancer Prev Res, 3: 108-113 (2010).
Basu et al., "Pomegranate juice: A heart-healthy fruit juice," Nutr Rev, 67(1): 49-56 (2009).
Berry Health Benefits Symposium (2009 Berry Health Benefis Symposium).
Bhattacharyya et al., "Beneficial Effect of Processed Shilajit on Swimming Exercise Induced Impaired Energy Status of Mice," Pharmacologyonline, 1: 817-825 (2009).
Bhattacharyya et al., "Shilajit Dibezno-alpha-Pyrones: Mitochondria Targeted Antioxidants," Pharmacologyonline, 2: 690-698 (2009).
Bialonska, et al., "Urolithins, Intenstinal Microbial Metabolites of Pomegranate Ellagitannins, Exhibit Potent Antioxidant Activity in a Cell-Based Assay," J Agric Food Chem, 57(21); 10181-10186, 2009.
Cerda et al., "Repeated oral administration of high doses of the pomegranate ellagitannin punialagin to rats for 37 days is not toxic," J. Agric. Food Chem., 51(11):3493-3501 (2003).
Cerda, et al., "Identification of Urolithin A as a metabolite produced by human colon microflora from ellagic acid and related compounds," J Agric Food Chem, 53(14): 5571-5576 (2005).
Cerda, et al., "Pomegranate juice supplementation in a chronic obstructive pulmonary disease: a 5-week, randomized, double-blind, placebo-controlled trial," Eur J Clin Nutr, 60: 245-253 (2006).
Chen, T. et al., "Rapamycin and other longevity-promoting compounds enhance the generation of mouse induced pluripotent stem cells", Aging Cell, 10(5):908-911 (Anatomical Society of Great Britain and Ireland, UK, Jun. 14, 2011).
Dell'agli, et al., "Ellagitannins of fruit rind of pomegranate (*Punica granatum*) antagonize in vitro the host inflammatory response mechanism involved in the onset of malaria," Malaria J, 9: 208 (2010).
Dr. Mark Percival, "Antioxidants," Clinical Nurtition Insights, 1998.
Esmaillzadeh et al., "Concentrated pomegranate juice improves lipid profiles in diabetic patients with hyperlipidemia," J Med Food, 7(3): 305-308 (2004).
Espín et al., "Iberian pig as a model to clarify obscure points in the bioavailability and metabolism of ellagitannins in humans," J Agric Food Chem, 55(25): 10476-10485 (2007).
Examination Report No. 2 dated Mar. 9, 2016 from corresponding Australian patent application No. 2011348068.
Ghosal et al., "Effects of shilajit and its active constituents on learning and memory in rats," Phytotherapy Res, 7(1): 29-34 (1993).
Ghosal et al., "Shilajit. Part 4. Chemistry of Two Bioactive Benzopyrone Metabolites," J Chem Research (S), 11: 350-351 (1989).
Gulcin et al., "Antioxidant and Antiradical Activities of L-carnitine," Life Sciences, 78: 803-811 (2006).
Hartman, R. E. et al. "Pomegranate juice decreases amyloid load and improves behavior in a mouse model of Alzheimer's disease", *Neurobiology of Disease*, 24(3):506-515 (Elsevier Inc., St. Louis, MO 2006).
International Search Report and Written Opinion from corresponding PCT application PCT/US2013/048310 dated Jan. 22, 2014.
International Search Report and Written Opinion from parent PCT application PCT/US2011/067229 dated Jul. 25, 2012.
Johanningsmeier et al., "Pomegranate as a functional food and nutraceutical source," Ann Rev Food Sci Technol, 2:181-201 (2010).
Kasimsetty, et al., "Colon cancer chemopreventive activities of pomegranate ellagitannins and Urolithins," J Agric Food Chem, 58(4): 2180-2187 (2010).
Kiss, A. K. et al., "Epigenetic modulation of mechanisms involved in inflammation: Influence of selected polyphenolic substances on histone acetylation state", *Food Chemistry*, 131(3):1015-1020 (Elsevier Ltd., Netherlands, Sep. 26, 2011).
Landete, J. M., "Ellagitannins, ellagic acid and their derived metabolites: A review about source, metabolism, functions and health", Food Research International, 44(5):1150-1160 (Elsevier Applied Science, Barking, GB, Apr. 17, 2011).
Larossa, M. et al., "Anti-inflammatory properties of a pomegranate extract and its metabolite urolithin-A in a colitis rat model and the effect of colon inflammation on phenolic metabolism", *Journal of Nutritional Biochemistry*, 21:717-725 (Elsevier Inc., 2010).
Larrosa, M. et al., "Ellagitannins, ellagic acid and vascular health", *Molecular Aspects of Medicine*, 31(6):513-539 (Pergamon Press, Oxford, Great Britain, Dec. 1, 2010).
Lee, H.-J. et al., "β-Secretase (BACE1) Inhibitors from Sanguisorbae Radix", *Arch. Pharm. Res.*, 28(7):799-803 (Korea, 2005).
Lin et al., "Pharmacological Promotion of Autophagy Alleviates Steatosis and Injury in Alcoholic and Non-alcoholic Fatty Liver Conditions in Mice," J Hepatol. May 2013; 58(5):993-999.
Manach et al., "Bioavailability and bioefficacy of polyphenols in humans. I. Review of 97 bioavailability studies [1-3]," Am. J. Clin. Nutr. 81(suppl):230S-242S (2005).
Office Action from corresponding Chinese Patent Application No. 201180067142.4 dated Jul. 3, 2014.
Office Action from corresponding Colombian Patent Application No. 12-172.849 dated Aug. 28, 2014.
Office Action from corresponding Mexican Patent Application No. MX/a/2013/007262, dated Mar. 11, 2016.
Office Action in co-pending US 2012/0164243-A1, dated Jul. 6, 2015.
Office Action in corresponding Japanese application No. JP2013-546456 dated Oct. 27, 2015.
Partial European Search Report for European Application No. 17186188.3 dated Oct. 27, 2017.
Rock et al., "Consumption of wonderful variety pomegranate juice and extract by diabetic patients increases paraoxonase 1 association with high-density lipoprotein and stimulates its catalytic activities," J Agric Food Chem, 56(18): 8704-8713 (2008).
Saul, N. et al., "Diversity of Polyphenol Action in Caenohabditis elegans: Between Toxicity and Longevity", *Journal of Natural Products*, 74(8):1713-1720 (American Chemical Society and American Society of Pharmacognosy, USA, Aug. 26, 2011).

(56) References Cited

OTHER PUBLICATIONS

Seeram, N. P. et al., "Pomegranate Ellagitannin-Derived Metabolites Inhibit Prostate Cancer Growth and Localize to the Mouse Prostate Gland", *J. Agric. Food Chem.*, 55:7732-7737 (American Chemcal Society, USA, 2007).

Sumner et al., "Effects of pomegranate juice consumption on myocardial perfusion in patients with coronary heart disease," Am J Cardiol, 96(6): 810-814 (2005).

Trombold, J. R. et al., "Ellagitannin Consumption Improves Strength Recovery 2-3 d after Eccentric Exercise", *Medicine and Science in Sports and Exercise*, 42:493-498 (American College of Sports Medicine, Mar. 2010).

Viuda-Martos, M. et al., "Pomegranate and its Many Functional Components as Related to Human Health: A Review", *Comprehensive Reviews in Food Science and Food Safety*, 9(6):635-654 (Oct. 22, 2010).

Zenjun et al., "Distribution of Ellagic Acids in Plantae and Thier Bioactivies," Natural Product Research and Development, 22:519-524 and 540 (2010).

Andreux et al., "Mitochondrial function is impaired in the skeletal muscle of pre-frail elderly," Scientific Reports, 8(8548):1-12 (2018).

Andreux et al., "The mitophagy activator urolithin A is safe and induces a molecular signature of improved mitochondrial and cellular health in humans," Nature Metabolism, 1-10 (2019).

Andreux et al., "The mitophagy activator urolithin A is safe and induces a molecular signature of improved mitochondrial and cellular health in humans," Nature Metabolism, 1:595-603 (2019).

\* cited by examiner

Plasma pharmacokinetic variables of Urolithin A after single dose oral administration

| Dose (mg) | $t_{max}$ (h) | $C_{max}$ (pg/mL) | $AUC_{0-36h}$ (pg.h/mL) |
|---|---|---|---|
| 250 | 6.01 | 601 | 6160 |
| 1000 | 6.00 | 1920 | 15800 |
| 2000 | 6.00 | 1040 | 12400 |

Fig. 1

Plasma pharmacokinetic variables of Urolithin A at day 28 following daily oral administration

| Day | Dose (mg) | Value | $t_{max}$ (h) | $C_{max}$ (pg/mL) | $AUC_{0-24h}$ (pg.h/mL) | $t_{1/2}$ (h) |
|---|---|---|---|---|---|---|
| 28 | 1000 | N | 9 | 9 | 9 | 9 |
| | | Mean | 6.33 | 1970 | 17500 | 22.4 |
| | | SD | 2.24 | 1070 | 6480 | 17.4 |

| MUSCLE RELATED GENESETS | 1000 MG | |
|---|---|---|
| GENESETS | NES | FDR |
| GO_HEART_MORPHOGENESIS | 1.8126 | 0.02788 |
| GO_MUSCLE_SYSTEM_PROCESS | 3.2426 | 0.00000 |
| GO_HEART_DEVELOPMENT | 1.9876 | 0.00695 |
| GO_REGULATION_OF_MUSCLE_CELL_DIFFERENTIATION | 1.4705 | 0.19032 |
| GO_MUSCLE_TISSUE_DEVELOPMENT | 1.5619 | 0.12999 |
| GO_REGULATION_OF_MUSCLE_CONTRACTION | 2.4387 | 0.00000 |
| GO_REGULATION_OF_MUSCLE_SYSTEM_PROCESS | 2.8157 | 0.00000 |
| GO_CARDIAC_CHAMBER_DEVELOPMENT | 1.5083 | 0.16192 |
| GO_MUSCLE_ORGAN_DEVELOPMENT | 2.4441 | 0.00000 |
| GO_SKELETAL_MUSCLE_ORGAN_DEVELOPMENT | 2.3554 | 0.00009 |
| GO_CARDIAC_MUSCLE_TISSUE_DEVELOPMENT | 2.3623 | 0.00007 |
| GO_POSITIVE_REGULATION_OF_MUSCLE_TISSUE_DEVELOPMENT | 1.6218 | 0.09463 |
| GO_REGULATION_OF_MUSCLE_TISSUE_DEVELOPMENT | 1.5619 | 0.12999 |
| GO_REGULATION_OF_MYOBLAST_DIFFERENTIATION | 1.5628 | 0.13006 |
| GO_REGULATION_OF_MUSCLE_ORGAN_DEVELOPMENT | 1.5478 | 0.13635 |
| GO_CARDIAC_VENTRICLE_DEVELOPMENT | 1.6122 | 0.09906 |
| GO_REGULATION_OF_SKELETAL_MUSCLE_TISSUE_DEVELOPMENT | 1.6580 | 0.07675 |
| GO_POSITIVE_REGULATION_OF_MUSCLE_TISSUE_DEVELOPMENT | 1.6218 | 0.09463 |
| GO_REGULATION_OF_STRIATED_MUSCLE_CELL_DIFFERENTIATION | 1.7741 | 0.03574 |
| GO_MUSCLE_ORGAN_MORPHOGENESIS | 2.1343 | 0.00114 |
| GO_STRIATED_MUSCLE_CONTRACTION | 2.2312 | 0.00032 |
| GO_SARCOLEMMA | 2.3495 | 0.00009 |
| GO_REGULATION_OF_MUSCLE_ADAPTATION | 2.3165 | 0.00011 |
| GO_REGULATION_OF_CARDIAC_CONDUCTION | 2.3576 | 0.00010 |
| GO_ACTOMYOSIN_STRUCTURE_ORGANIZATION | 2.3833 | 0.00005 |
| GO_MYOFIBRIL_ASSEMBLY | 2.4923 | 0.00000 |
| GO_STRUCTURAL_CONSTITUENT_OF_MUSCLE | 2.3990 | 0.00000 |
| GO_A_BAND | 2.4931 | 0.00000 |
| GO_SARCOPLASMIC_RETICULUM_MEMBRANE | 2.5287 | 0.00000 |
| GO_SARCOPLASM | 2.6827 | 0.00000 |
| GO_STRIATED_MUSCLE_CELL_DIFFERENTIATION | 2.7823 | 0.00000 |
| GO_MUSCLE_CELL_DIFFERENTIATION | 2.8332 | 0.00000 |
| GO_I_BAND | 2.9871 | 0.00000 |
| GO_MUSCLE_CELL_DEVELOPMENT | 2.9213 | 0.00000 |
| GO_MUSCLE_STRUCTURE_DEVELOPMENT | 3.0188 | 0.00000 |
| GO_MUSCLE_CONTRACTION | 3.1556 | 0.00000 |
| GO_CONTRACTILE_FIBER | 3.3752 | 0.00000 |

Fig. 7

| MITOCHONDRIAL RELATED GENESETS | 1000 MG | |
| --- | --- | --- |
| GENESETS | NES | FDR |
| GO_INNER_MITOCHONDRIAL_MEMBRANE_PROTEIN_COMPLEX | 1.6395 | 0.0855 |
| GO_MITOCHONDRIAL_PROTEIN_COMPLEX | 1.6686 | 0.0728 |
| GO_MITOCHONDRION_ORGANIZATION | 1.7571 | 0.0398 |
| GO_MITOCHONDRIAL_ENVELOPE | 1.7629 | 0.0387 |
| GO_MITOCHONDRIAL_MEMBRANE_PART | 1.6972 | 0.0621 |
| GO_MITOCHONDRION | 1.9391 | 0.0102 |
| GO_MITOCHONDRIAL_MATRIX | 1.9872 | 0.0069 |
| GO_MITOCHONDRIAL_PART | 2.0906 | 0.0021 |

Fig. 8

METHOD FOR IMPROVING MITOPHAGY IN SUBJECTS

FIELD

The present disclosure relates to methods involving oral administration of urolithins according to a specific dosage regime, resulting in the provision of beneficial health effects, for example improved mitochondrial function and cellular metabolism. The methods are useful, e.g, for improving the health and wellbeing of subjects, particularly the elderly or frail; and for improving fitness, muscle performance and/or to endurance of those engaging in exercise. The methods are also useful in treating or preventing various conditions, e.g. conditions associated with inadequate mitochondrial activity, and/or muscle-related disorders.

BACKGROUND

The past hundred years has seen dramatic increases in human life expectancy. Old age is often associated with increased health problems and/or decreased body function. As one example, good muscle performance is important for effective living at all stages of life, and loss of muscle mass or poor muscle performance in the elderly can present problems with mobility and completion of everyday tasks. Many of those in their later years are encouraged to eat a balanced diet, take regular exercise and take dietary supplements, in order to remain healthy.

Changes in lifestyle habits over recent decades (e.g. diet, inactivity) have also seen an increase in the number of people who are overweight or obese, which disorders are associated with conditions such as diabetes and heart disease, placing strain on health services. Consequently, there remains a real need for new approaches to maintain health and facilitate active lifestyles.

Many individuals do of course undertake regular exercise, and of those a number consume supplements to help improve fitness and/or assist recovery from injuries. For example, improved muscle performance is of particular interest to many athletes. An increase in muscular contraction strength, increase in amplitude of muscle contraction, or shortening of muscle reaction time between stimulation and contraction would all be of benefit to individuals undertaking exercise. It would be desirable to provide new approaches to support those undertaking exercise to improve their physical fitness and endurance further.

Low muscle mass or poor muscle performance are also characteristics of many diseases and conditions. Muscle-related pathological conditions include myopathies, neuromuscular diseases, such as Duchenne muscular dystrophy, acute sarcopenia, for example muscle atrophy and/or cachexia, for example associated with burns, bed rest, limb immobilization, or major thoracic, abdominal, neck and/or orthopedic surgery. Age-related muscle-loss is an especially prevalent condition. Cachexia due to prolonged immobilization or other diseases, for example cancer, are other conditions that are often characterised by poor muscle performance. It would further be desirable to provide new means of treating, preventing or at least reducing the effects of such disorders.

Urolithins are a group of ellagitannin- and ellagic acid-derived metabolites produced by, e.g., mammalian colonic microflora. Urolithins have been proposed as being compounds useful for promoting longevity, see for example WO2014/004902.

However, the development of effective and safe new dietary supplements and therapies is a complex, time-consuming and unpredictable field. A number of substances purported to have beneficial effects have ultimately proved to be unsuitable, for example as a result of poor efficacy, unacceptable side effects, or unsuitable pharmacokinetic properties. In many cases, such problems do not emerge until clinical trials are carried out.

The present inventors have now found that oral administration of urolithin A according to a particular dosage regimen in human subjects results in unexpectedly good pharmacokinetic properties, such that the dosage regime resulted in significant effects on biomarkers associated with muscle and/or mitochondrial function being observed. Oral administration of urolithin A at 1000 mg dosage unexpectedly resulted in improved pharmacokinetics (higher $C_{max}$ and AUC) compared with administration of the same compound at 2000 mg dosage.

SUMMARY

The present disclosure provides a compound of formula (I)

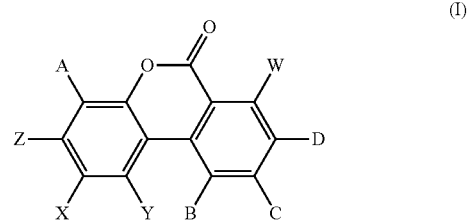

wherein:
A, B, C, D, W, X, Y and Z are each independently selected from H and OH;
or a salt thereof;
for use as a dietary, nutritional and/or health supplement, as a food ingredient or as an active ingredient used in food, or as an active ingredient used in a pharmaceutical product wherein the compound or salt is orally administered to a subject in a daily amount of from 2.8 to 6.0 mmol per day, over a period of at least 21 days.

In a further embodiment, the compound of formula (I) is administered to the subject in a daily amount of from 2.8 to 6.6 mmol per day, over a period of at least 21 days.

For the avoidance of doubt, conventional rounding is assumed herein. For example, the figure 2.8 as used above in the context of 2.8 mmol (with two significant figures) refers to an amount which, when rounded up or down to two significant figures, gives 2.8. It includes, for example, 2.84 and 2.75.

The present disclosure also provides a compound of formula (I) wherein: A, B, C, D, W, X, Y and Z are each independently selected from H and OH;
or a salt thereof;
for use as a dietary, nutritional and/or health supplement, as a food ingredient, or as an active ingredient used in food or as an active ingredient used in a pharmaceutical product, wherein the compound or salt is orally administered at a dose sufficient to achieve peak plasma levels of a compound of formula (I), and/or metabolites thereof, of 900-1350 ng/ml.

In one embodiment peak plasma levels are between 1000-1250 ng/ml of total compound of formula (I), for example, about 1100 ng/ml, for example about 1000 ng/ml.

In one embodiment peak plasma levels are maintained for between 5-12 hours, for example 5-10 hours, for example about 8 hours, for example about 7 hours, for example about 6 hours, for example such as about 5 hours.

In one embodiment peak plasma levels are obtained within 7 days with once daily dosing, for example, within 6 days, 5 days, 4 days, 3 days or 2 days.

The term 'about' or 'approximately' may be used herein refers to ±20%, for example, ±15%, for example ±10% such as ±5%.

The word 'total' when used in connection with the words/phrase compound of formula (I) or urolithin refers to the sum of the compound and its metabolites for example, the glucuronide and the sulphate forms.

The present disclosure also provides use of a compound of formula (I) wherein: A, B, C, D, W, X, Y and Z are each independently selected from H and OH;
or a salt thereof;
as a dietary, nutritional and/or health supplement, as a food ingredient, or as an active ingredient used in food, wherein the compound or salt is orally administered at a dose sufficient to achieve steady state plasma levels of a compound of formula (I) and/or metabolites thereof, of 260-960 ng/ml.

The 'steady state' level is defined as the minimum concentration of total compound in plasma comprising the parent compound, for example, Urolithin A and its metabolites such as urolithin A glucuronide and urolithin A sulphate to which the concentration of total compound falls after 24 hour post dosing, prior to giving the next dose.

In one embodiment, steady state levels are 300-960 ng/ml, for example, 340-940 ng/ml, such as 380-840 ng/ml, such as 380-720 ng/ml, such as about 600 ng/ml. In a further embodiment steady state levels are 400-700 ng/ml.

The present disclosure also provides a method of increasing mitophagy and/or autophagy, improving mitochondrial function and/or improving cellular metabolism in a subject, the method comprising:
orally administering a compound of formula (I)

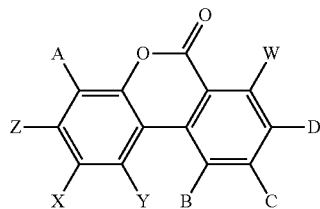

(I)

wherein:
A, B, C, D, W, X, Y and Z are each independently selected from H and OH; or a salt thereof;
to the subject in a daily amount of from 2.8 to 6.0 mmol per day, over a period of at least 21 days.

Improving mitochondrial function includes increasing mitochondrial biogenesis.

In a further embodiment, the compound of formula (I) is administered to the subject in a daily amount of from 2.8 to 6.6 mmol per day, over a period of at least 21 days.

The present disclosure also provides a method of increasing mitophagy and/or autophagy, improving mitochondrial function and/or improving cellular metabolism in a subject, the method comprising: orally administering a compound of formula (I) wherein: A, B, C, D, W, X, Y and Z are each independently selected from H and OH; or a salt thereof; wherein the compound or salt is orally administered at a dose sufficient to achieve peak plasma levels of a compound of formula (I) and/or metabolites thereof, of 900-1350 ng/ml.

The present disclosure also provides a method of increasing mitophagy and/or autophagy, improving mitochondrial function and/or improving cellular metabolism in a subject, the method comprising: orally administering a compound of formula (I) wherein: A, B, C, D, W, X, Y and Z are each independently selected from H and OH; or a salt thereof; wherein the compound or salt is orally administered at a dose sufficient to achieve steady state plasma levels of a compound of formula (I) and/or metabolites thereof, of 260-960 ng/ml.

The present disclosure also provides a compound of formula (I) wherein: A, B, C, D, W, X, Y and Z are each independently selected from H and OH;
or a salt thereof; for use in increasing mitophagy and/or autophagy, improving mitochondrial function and/or improving cellular metabolism in a subject, wherein the compound or salt is orally administered to a subject in a daily amount of from 2.8 to 6.0 mmol per day, over a period of at least 21 days.

In a further embodiment, the compound of formula (I) is administered to the subject in a daily amount of from 2.8 to 6.6 mmol per day, over a period of at least 21 days.

The present disclosure also provides a compound of formula (I) wherein: A, B, C, D, W, X, Y and Z are each independently selected from H and OH:
or a salt thereof;
for use in increasing mitophagy and/or autophagy, improving mitochondrial function and/or improving cellular metabolism in a subject, wherein the compound or salt is orally administered at a dose sufficient to achieve peak plasma levels of a compound of formula (I) and/or metabolites thereof, of 900-1350 ng/ml.

The present disclosure also provides a compound of formula (I) wherein: A, B, C, D, W, X, Y and Z are each independently selected from H and OH;
or a salt thereof; for use in increasing mitophagy and/or autophagy, improving mitochondrial function and/or improving cellular metabolism in a subject, wherein the compound or salt is orally administered at a dose sufficient to achieve steady state plasma levels of a compound of formula (I) and/or metabolites thereof, of 260-960 ng/ml.

The present disclosure also provides use of a compound of formula (I) wherein: A, B, C, D, W, X, Y and Z are each independently selected from H and OH;
or a salt thereof; in the manufacture of a medicament for increasing mitophagy and/or autophagy, improving mitochondrial function and/or improving cellular metabolism in a subject wherein the compound or salt is orally administered in a daily amount in the range of from 2.8 to 6.0 mmol per day, over a period of at least 21 days.

In a further embodiment, the compound of formula (I) is administered to the subject in a daily amount of from 2.8 to 6.6 mmol per day, over a period of at least 21 days.

The present disclosure also provides use of a compound of formula (I) wherein: A, B, C, D, W, X, Y and Z are each independently selected from H and OH;
or a salt thereof; for the manufacture of a medicament for increasing mitophagy and/or autophagy, improving mitochondrial function and/or improving cellular metabolism in a subject, wherein the compound or salt is orally administered at a dose sufficient to achieve peak plasma levels of a compound of formula (I) and/or metabolites thereof, of 900-1350 ng/ml.

The present disclosure also provides use of a compound of formula (I) wherein: A, B, C, D, W, X, Y and Z are each independently selected from H and OH;

or a salt thereof; for the manufacture of a medicament for increasing mitophagy and/or autophagy, improving mitochondrial function and/or improving cellular metabolism in a subject, wherein the compound or salt is orally administered at a dose sufficient to achieve steady state plasma levels of a compound of formula (I) and/or metabolites thereof, of 260-960 ng/ml.

A compound of formula (I)

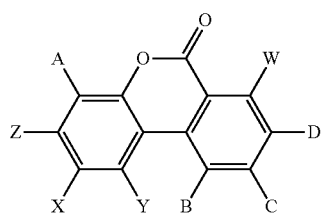

(I)

wherein:
A, B, C, D, W, X, Y and Z are each independently selected from H and OH; or a salt thereof;
for use in increasing mitochondrial biogenesis in a subject wherein the compound or salt is orally administered to a subject; either
(i) in a daily amount of from 2.8 to 6.6 mmol per day, over a period of at least 21 days.
(ii) at a dose sufficient to achieve peak plasma levels of a compound of formula (I), and/or metabolites thereof, of 900-1350 ng/ml; or
(iii) at a dose sufficient to achieve steady state plasma levels of a compound of formula (I) and/or metabolites thereof, of 260-960 ng/ml.

The present disclosure also provides a method for increasing mitochondrial biosynthesis in a subject, the method comprising: orally administering a compound of formula (I) wherein: A, B, C, D, W, X, Y and Z are each independently selected from H and OH;

or a salt thereof; wherein the compound or salt is orally administered to a subject either:
(i) in a daily amount of from 2.8 to 6.6 mmol per day, over a period of at least 21 days.
(ii) at a dose sufficient to achieve peak plasma levels of a compound of formula (I), and/or metabolites thereof, of 900-1350 ng/ml; or
(iii) at a dose sufficient to achieve steady state plasma levels of a compound of formula (I) and/or metabolites thereof, of 260-960 ng/ml.

The present disclosure also provides use of a compound of formula (I) wherein: A, B, C, D, W, X, Y and Z are each independently selected from H and OH;

or a salt thereof; for the manufacture of a medicament for increasing mitochondrial biosynthesis in a subject, wherein the compound or salt is orally administered to a subject either;
(i) in a daily amount of from 2.8 to 6.6 mmol per day, over a period of at least 21 days.
(ii) at a dose sufficient to achieve peak plasma levels of a compound of formula (I), and/or metabolites thereof, of 900-1350 ng/ml; or
(iii) at a dose sufficient to achieve steady state plasma levels of a compound of formula (I) and/or metabolites thereof, of 260-960 ng/ml.

The present disclosure also provides a method of maintaining and/or improving muscle function and/or performance, body health, fitness, $ATP^{max}$, muscle ATP use, oxygen consumption, muscle bioenergetics, muscle endurance, tolerance to exercise, recovery from exercise and/or endurance in a subject, the method comprising:
orally administering a compound of formula (I)

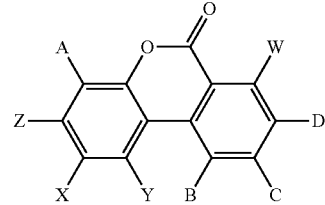

(I)

wherein:
A, B, C, D, W, X, Y and Z are each independently selected from H and OH; or a salt thereof;
to the subject in a daily amount of from 2.8 to 6.0 mmol per day, over a period of at least 21 days.

In a further embodiment, the compound of formula (I) is administered to the subject in a daily amount of from 2.8 to 6.6 mmol per day, over a period of at least 21 days.

In one embodiment, the present disclosure provides maintaining and/or improving tissue and/or muscle $ATP^{max}$.

The present disclosure also provides a method of maintaining and/or improving muscle function and/or performance, body health, fitness, $ATP^{max}$, including tissue and/or muscle $ATP^{max}$, muscle ATP use, oxygen consumption, muscle bioenergetics, muscle endurance, tolerance to exercise, recovery from exercise and/or endurance in a subject, the method comprising: orally administering a compound of formula (I) wherein: A, B, C, D, W, X, Y and Z are each independently selected from H and OH; or a salt thereof; wherein the compound or salt is orally administered at a dose sufficient to achieve peak plasma levels of a compound of formula (I) and/or metabolites thereof, of 900-1350 ng/ml.

The present disclosure also provides a method of maintaining and/or improving muscle function and/or performance, body health, fitness, $ATP^{max}$, including tissue and/or muscle $ATP^{max}$, muscle ATP use, oxygen consumption, muscle bioenergetics, muscle endurance, tolerance to exercise, recovery from exercise and/or endurance in a subject, the method comprising: orally administering a compound of formula (I) wherein: A, B, C, D, W, X, Y and Z are each independently selected from H and OH; or a salt thereof; wherein the compound or salt is orally administered at a dose sufficient to achieve steady state plasma levels of a compound of formula (I) and/or metabolites thereof, of 260-960 ng/ml.

The present disclosure also provides a compound of formula (I) wherein: A, B, C, D, W, X, Y and Z are each independently selected from H and OH;

or a salt thereof; for use in maintaining and/or improving muscle function and/or performance, body health, fitness, $ATP^{max}$, including tissue and/or muscle $ATP^{max}$, muscle ATP use, oxygen consumption, muscle bioenergetics, muscle endurance, tolerance to exercise, recovery from exercise and/or endurance in a subject, wherein the compound or salt is orally administered to a subject in a daily amount of from 2.6 to 6.0 mmol per day, over a period of at least 21 days.

In a further embodiment, the compound of formula (I) is administered to the subject in a daily amount of from 2.8 to 6.6 mmol per day, over a period of at least 21 days.

The present disclosure also provides a compound of formula (I) wherein: A, B, C, D, W, X, Y and Z are each independently selected from H and OH;

or a salt thereof; for maintaining and/or improving muscle function and/or performance, body health, fitness, ATP$^{max}$, including tissue and/or muscle ATP$^{max}$, muscle ATP use, oxygen consumption, muscle bioenergetics, muscle endurance, tolerance to exercise, recovery from exercise and/or endurance in a subject, wherein the compound or salt is orally administered at a dose sufficient to achieve peak plasma levels of a compound of formula (I) and/or metabolites thereof, of 900-1350 ng/ml.

The present disclosure also provides a compound of formula (I) wherein: A, B, C, D, W, X, Y and Z are each independently selected from H and OH:

or a salt thereof; for use in maintaining and/or improving muscle function and/or performance, body health, fitness, ATP$^{max}$, including tissue and/or muscle ATP$^{max}$, muscle ATP use, oxygen consumption, muscle bioenergetics, muscle endurance, tolerance to exercise, recovery from exercise and/or endurance in a subject, wherein the compound or salt is orally administered at a dose sufficient to achieve steady state plasma levels of a compound of formula (I) and/or metabolites thereof, of 260-960 ng/ml.

The present disclosure also provides use of a compound of formula (I) wherein: A, B, C, D, W, X, Y and Z are each independently selected from H and OH;

or a salt thereof; for the manufacture of a medicament for maintaining and/or improving muscle function and/or performance, body health, fitness, ATP$^{max}$, including tissue and/or muscle ATP$^{max}$, muscle ATP use, oxygen consumption, muscle bioenergetics, muscle endurance, tolerance to exercise, recovery from exercise and/or endurance in a subject, wherein the compound of formula (I) or salt thereof is administered to the subject orally in a daily amount in the range of from 2.8 to 6.0 mmol per day, over a period of at least 21 days.

In a further embodiment, the compound of formula (I) is administered to the subject in a daily amount of from 2.8 to 6.6 mmol per day, over a period of at least 21 days.

The present disclosure also provides use of a compound of formula (I) wherein: A, B, C, D, W, X, Y and Z are each independently selected from H and OH;

or a salt thereof; for the manufacture of a medicament for maintaining and/or improving muscle function and/or performance, body health, fitness, ATP$^{max}$, including tissue and/or muscle ATP$^{max}$, muscle ATP use, oxygen consumption, muscle bioenergetics, muscle endurance, tolerance to exercise, recovery from exercise and/or endurance in a subject, wherein the compound or salt is orally administered at a dose sufficient to achieve peak plasma levels of a compound of formula (I) and/or metabolites thereof, of 900-1350 ng/ml.

The present disclosure also provides use of a compound of formula (I) wherein: A, B, C, D, W, X, Y and Z are each independently selected from H and OH; or a salt thereof; in the manufacture of a medicament for maintaining and/or improving muscle function and/or performance, body health, fitness, ATP$^{max}$, including tissue and/or muscle ATP$^{max}$, muscle ATP use, oxygen consumption, muscle bioenergetics, muscle endurance, tolerance to exercise, recovery from exercise and/or endurance in a subject, wherein the compound or salt is orally administered at a dose sufficient to achieve steady state plasma levels of a compound of formula (I) and/or metabolites thereof, of 260-960 ng/ml.

The present disclosure also provides a method of helping maintain healthy muscle function, providing nutritional support for muscle health, supporting mitochondrial biogenesis in muscle and/or supporting mitochondrial health in muscle in a subject, the method comprising:

orally administering a compound of formula (I)

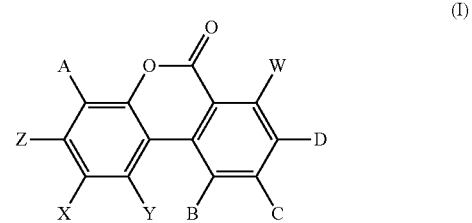

(I)

wherein:
A, B, C, D, W, X, Y and Z are each independently selected from H and OH; or a salt thereof;
to the subject in a daily amount of from 2.8 to 6.0 mmol per day, over a period of at least 21 days.

In a further embodiment, the compound of formula (I) is administered to the subject in a daily amount of from 2.8 to 6.6 mmol per day, over a period of at least 21 days.

The present disclosure also provides a method of helping maintain healthy muscle function, providing nutritional support for muscle health, supporting mitochondrial biogenesis in muscle and/or supporting mitochondrial health in muscle in a subject, the method comprising: orally administering a compound of formula (I) wherein: A, B, C, D, W, X, Y and Z are each independently selected from H and OH;

or a salt thereof; wherein the compound or salt is orally administered at a dose sufficient to achieve peak plasma levels of a compound of formula (I) and/or metabolites thereof, of 900-1350 ng/ml.

The present disclosure also provides a method of helping maintain healthy muscle function, providing nutritional support for muscle health, supporting mitochondrial biogenesis in muscle and/or supporting mitochondrial health in muscle in a subject, the method comprising: orally administering a compound of formula (I) wherein: A, B, C, D, W, X, Y and Z are each independently selected from H and OH;

or a salt thereof; wherein the compound or salt is orally administered at a dose sufficient to achieve steady state plasma levels of a compound of formula (I) and/or metabolites thereof, of 260-960 ng/ml.

The present disclosure also provides a compound of formula (I)

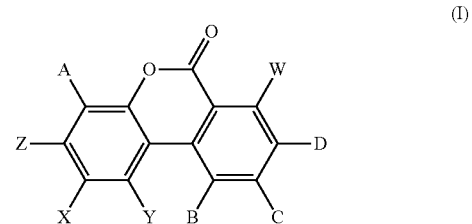

(I)

wherein:

A, B, C, D, W, X, Y and Z are each independently selected from H and OH; or a salt thereof;

for use in helping maintain healthy muscle function, providing nutritional support for muscle health, supporting mitochondrial biogenesis in muscle and/or supporting mitochondrial health in muscle in a subject, wherein the compound of formula (I) is administered to the subject in a daily amount of from 2.8 to 6.0 mmol per day, over a period of at least 21 days.

In a further embodiment, the compound of formula (I) is administered to the subject in a daily amount of from 2.8 to 6.6 mmol per day, over a period of at least 21 days.

The present disclosure also provides a compound of formula (I) wherein: A, B, C, D, W, X, Y and Z are each independently selected from H and OH;

or a salt thereof;

for use in helping maintain healthy muscle function, providing nutritional support for muscle health, supporting mitochondrial biogenesis in muscle and/or supporting mitochondrial health in muscle in a subject, wherein the compound or salt is orally administered at a dose sufficient to achieve peak plasma levels of a compound of formula (I) and/or metabolites thereof, of 900-1350 ng/ml.

The present disclosure also provides a compound of formula (I) wherein: A, B, C, D, W, X, Y and Z are each independently selected from H and OH;

or a salt thereof;

for use in helping maintain healthy muscle function, providing nutritional support for muscle health, supporting mitochondrial biogenesis in muscle and/or supporting mitochondrial health in muscle in a subject, wherein the compound or salt is orally administered at a dose sufficient to achieve steady state plasma levels of a compound of formula (I) and/or metabolites thereof, of 260-960 ng/ml.

The present disclosure also provides use of a compound of formula (I) wherein: A, B, C, D, W, X, Y and Z are each independently selected from H and OH;

or a salt thereof; for the manufacture of a medicament for helping maintain healthy muscle function, providing nutritional support for muscle health, supporting mitochondrial biogenesis in muscle and/or supporting mitochondrial health in muscle in a subject, wherein the compound of formula (I) or salt thereof is administered to the subject orally in a daily amount in the range of from 2.8 to 6.0 mmol per day, over a period of at least 21 days.

In a further embodiment, the compound of formula (I) is administered to the subject in a daily amount of from 2.8 to 6.6 mmol per day, over a period of at least 21 days.

The present disclosure also provides use of a compound of formula (I) wherein: A, B, C, D, W, X, Y and Z are each independently selected from H and OH;

or a salt thereof; for the manufacture of a medicament for helping maintain healthy muscle function, providing nutritional support for muscle health, supporting mitochondrial biogenesis in muscle and/or supporting mitochondrial health in muscle in a subject, wherein the compound or salt is orally administered at a dose sufficient to achieve peak plasma levels of a compound of formula (I) and/or metabolites thereof, of 900-1350 ng/ml.

The present disclosure also provides use of a compound of formula (I) wherein: A, B, C, D, W, X, Y and Z are each independently selected from H and OH;

or a salt thereof; in the manufacture of a medicament for helping maintain healthy muscle function, providing nutritional support for muscle health, supporting mitochondrial biogenesis in muscle and/or supporting mitochondrial health in muscle in a subject, wherein the compound or salt is orally administered at a dose sufficient to achieve steady state plasma levels of a compound of formula (I) and/or metabolites thereof, of 260-960 ng/ml.

The present disclosure also provides a method of helping maintain healthy muscle function, providing nutritional support for muscle health, supporting mitochondrial biogenesis in muscle and/or supporting mitochondrial health in muscle in a subject, the method comprising:

orally administering a compound of formula (I)

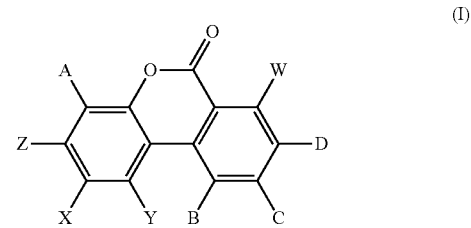

wherein:

A, B, C, D, W, X, Y and Z are each independently selected from H and OH; or a salt thereof;

to the subject in a daily amount of from 2.8 to 6.0 mmol per day, over a period of at least 21 days.

In a further embodiment, the compound of formula (I) is administered to the subject in a daily amount of from 2.8 to 6.6 mmol per day, over a period of at least 21 days.

The present disclosure also provides a method of helping maintain healthy muscle function, providing nutritional support for muscle health, supporting mitochondrial biogenesis in muscle and/or supporting mitochondrial health in muscle in a subject, the method comprising: orally administering a compound of formula (I) wherein: A, B, C, D, W, X, Y and Z are each independently selected from H and OH;

or a salt thereof; wherein the compound or salt is orally administered at a dose sufficient to achieve peak plasma levels of a compound of formula (I) and/or metabolites thereof, of 900-1350 ng/ml.

The present disclosure also provides a method of helping maintain healthy muscle function, providing nutritional support for muscle health, supporting mitochondrial biogenesis in muscle and/or supporting mitochondrial health in muscle in a subject, the method comprising: orally administering a compound of formula (I) wherein: A, B, C, D, W, X, Y and Z are each independently selected from H and OH;

or a salt thereof; wherein the compound or salt is orally administered at a dose sufficient to achieve steady state plasma levels of a compound of formula (I) and/or metabolites thereof, of 260-960 ng/ml.

The present disclosure also provides a method of treatment and/or prophylaxis of a condition, disease or disorder in a subject, the method comprising: orally administering a compound of formula (I)

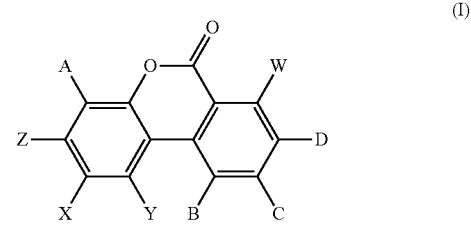

wherein:

A, B, C, D, W, X, Y and Z are each independently selected from H and OH; or a salt thereof;

to the subject in a daily amount of from 2.8 to 6.0 mmol per day, over a period of at least 21 days.

In a further embodiment, the compound of formula (I) is administered to the subject in a daily amount of from 2.8 to 6.6 mmol per day, over a period of at least 21 days.

The present disclosure also provides a method of treatment and/or prophylaxis of a condition, disease or disorder in a subject, the method comprising:

orally administering a compound of formula (I) wherein: A, B, C, D, W, X, Y and Z are each independently selected from H and OH; or a salt thereof; to the subject, wherein the compound or salt is orally administered at a dose sufficient to achieve peak plasma levels of a compound of formula (I) and/or metabolites thereof, of 900-1350 ng/ml.

The present disclosure also provides a method of treatment and/or prophylaxis of a condition, disease or disorder in a subject, the method comprising:

orally administering a compound of formula (I) wherein: A, B, C, D, W, X, Y and Z are each independently selected from H and OH;

or a salt thereof; to the subject wherein the compound or salt is orally administered at a dose sufficient to achieve steady state plasma levels of a compound of formula (I) and/or metabolites thereof, of 260-960 ng/ml.

The present disclosure also provides a compound of formula (I)

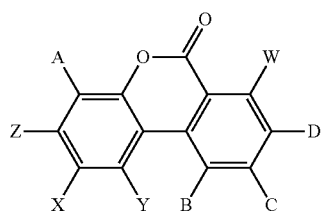

wherein:

A, B, C, D, W, X, Y and Z are each independently selected from H and OH; or a salt thereof;

for use in the treatment or prophylaxis of a condition, disease or disorder in a subject, wherein the compound of formula (I) or salt thereof is administered orally to the subject in a daily amount in the range of from 2.8 to 6.0 mmol per day, over a period of at least 21 days.

In a further embodiment, the compound of formula (I) is administered to the subject in a daily amount of from 2.8 to 6.6 mmol per day, over a period of at least 21 days.

The present disclosure also provides a compound of formula (I) wherein: A, B, C, D, W, X, Y and Z are each independently selected from H and OH;

or a salt thereof; for use in the treatment or prophylaxis of a condition, disease or to disorder in a subject; wherein the compound or salt is orally administered at a dose sufficient to achieve peak plasma levels of a compound of formula (I) and/or metabolites thereof, of 900-1350 ng/ml.

The present disclosure also provides a compound of formula (I) wherein: A, B, C, D, W, X, Y and Z are each independently selected from H and OH;

or a salt thereof; for use in the treatment of and/or prophylaxis of a condition, disease or disorder in a subject, wherein the compound or salt is orally administered at a dose sufficient to achieve steady state plasma levels of a compound of formula (I) and/or metabolites thereof, of 260.960 ng/ml.

The present disclosure also provides use of a compound of formula (I)

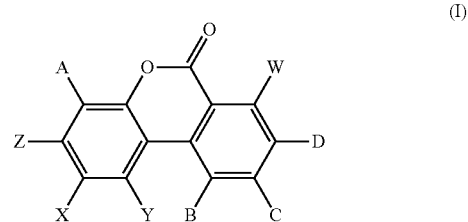

wherein:

A, B, C, D, W, X, Y and Z are each independently selected from H and OH;

or a salt thereof;

for the manufacture of a medicament for use in the treatment and/or prophylaxis of a condition in a subject, wherein the compound of formula (I) or salt thereof is administered to the subject orally in a daily amount in the range of from 2.8 to 6.0 mmol per day, over a period of at least 21 days.

In a further embodiment, the compound of formula (I) is administered to the subject in a daily amount of from 2.8 to 6.6 mmol per day, over a period of at least 21 days.

The present disclosure also provides use of a compound of formula (I) wherein: A, B, C, D, W, X, Y and Z are each independently selected from H and OH;

or a salt thereof; in the manufacture of a medicament for the treatment of and/or prophylaxis of a condition, disease or disorder in a subject, in a subject, wherein the compound or salt is orally administered at a dose sufficient to achieve peak plasma levels of a compound of formula (I) and/or metabolites thereof, of 900-1350 ng/ml.

The present disclosure also provides use of a compound of formula (I) wherein: A, B, C, D, W, X, Y and Z are each independently selected from H and OH;

or a salt thereof; in the manufacture of a medicament for the treatment of and/or prophylaxis of a condition, disease or disorder in a subject, in a subject, wherein the compound or salt is orally administered at a dose sufficient to achieve steady state plasma levels of a compound of formula (I) and/or metabolites thereof, of 260-960 ng/ml.

In a mode of implementation of the invention, the compound is administered as a metabolite of the compound of formula (I), for example a glucuronide or a sulphate. Urolithin B has a metabolite Urolthin B 3-O-glucuronide which has a molecular weight of 388 g/mol. If 4.4 mmol of that compound were administered per day, that would be 1,707.2 mg per day. Urolithin B also has a metabolite Urolthin B 3-O-sulfate which has a molecular weight of 292 g/mol. If 4.4 mmol of that compound were administered per day, that would be 1284.4 mg per day. Urolithin A has a metabolite Urolthin A 3-O-glucuronide which has a molecular weight of 404 g/mol. If 4.4 mmol of that compound were administered per day, that would be 1,777.6 mg per day. Urolithin A also has a metabolite Urolthin A 3-O-sulfate which has a molecular weight of 308 g/mol. If 4.4 mmol of that compound were administered per day, that would be 1,355.2 mg per day.

SUMMARY OF THE FIGURES

FIG. 1 shows a table summarising plasma pharmacokinetic variables for urolithin A in healthy elderly subjects after oral administration of a single dose of 250, 1000 or 2000 mg urolithin A.

FIG. 7 shows a table indicating the level of enrichment in expression levels of muscle-related gene sets at day 28 vs. day −1 (pre-dose) for a cohort of subjects administered 1000 mg/day urolithin A compared with placebo.

FIG. 8 shows a table indicating the level of enrichment in expression levels of mitochondrial-related gene sets at day 28 vs. day −1 (pre-dose) for a cohort of subjects administered 1000 mg/day urolithin A compared with placebo.

Figure 2:
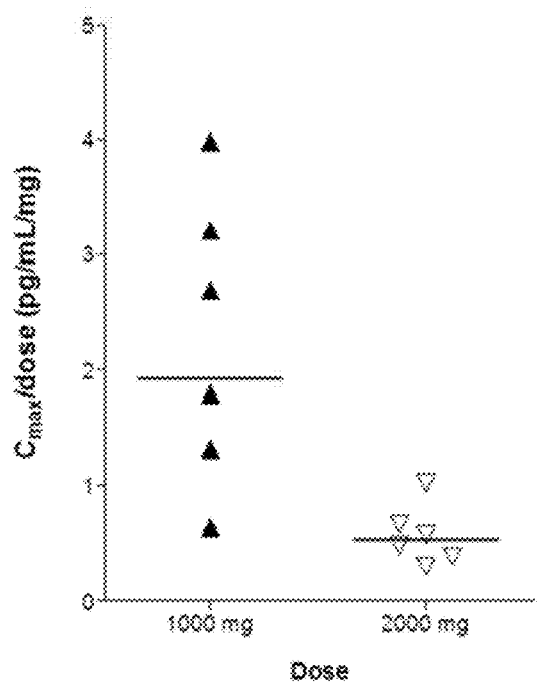
FIG. 2 shows a chart summarising dose-normalized individual and mean values for plasma $C_{max}$ of Urolithin A following oral administration of a single dose of 1000 mg or 2000 mg urolithin A to healthy elderly subjects.

Plasma data are from the time points of pre-dosing (Day 0), 7 days after dosing (Day 7), 14 days after dosing (Day 14), prior to the last dosing in Week 4 (Day 28), 24 hours after the last dosing on Day 28 (Day 29), 72 hours after the last dosing on Day 28 (Day 31) and finally 96 hours after the last dosing on Day 28 (Day 32).

DETAILED DESCRIPTION

The present disclosure provides methods involving oral administration of specific daily dosages of compounds of formula (I). i.e. urolithins, which provide beneficial health effects.

Compounds of Formula (I) and Salts Thereof

Urolithins are metabolites produced by the action of mammalian, including human, gut microbiota on ellagitannins and ellagic acid. Ellagitannins and ellagic acid are compounds commonly found in foods such as pomegranates, nuts and berries. Ellagitannins are minimally absorbed in the gut themselves. Urolithins are a class of compounds with the representative structure (I) shown above. The structures of some particularly common urolithins are described in Table 1 below, with reference to structure (I).

| | Substituent of structure (I) | | | | | |
|---|---|---|---|---|---|---|
| | A | B | C | D | W, X and Y | Z |
| Urolithin A | H | H | H | OH | H | OH |
| Urolithin B | H | H | H | H | H | OH |
| Urolithin C | H | H | OH | OH | H | OH |
| Urolithin D | OH | H | OH | OH | H | OH |
| Urolithin E | OH | OH | H | OH | H | OH |
| Isourolithin A | H | H | OH | H | H | OH |
| Isourolithin B | H | H | OH | H | H | H |
| Urolithin M-5 | OH | OH | OH | OH | H | OH |
| Urolithin M-6 | H | OH | OH | OH | H | OH |
| Urolithin M-7 | H | OH | H | OH | H | OH |

In practice, for commercial scale products, it is convenient to synthesise the urolithins. Routes of synthesis are described, for example, in WO2014/004902. Urolithins of any structure according to structure (I) may be used in the methods of the present disclosure.

In one aspect of the uses and methods of the present disclosure, a suitable compound is a compound of formula (I) wherein A, C, D and Z are independently selected from H and OH and B, W, X and Y are all H.

Particularly suitable compounds are the naturally-occurring urolithins. Thus, Z is preferably OH and W, X and Y are preferably all H. When W, X and Y are all H, and A, and B are both H, and C, D and Z are all OH, then the compound is Urolithin C. When W, X and Y are all H, and A, B, C and D are all H, and Z is OH, then the compound is urolithin B. When W, X and Y are all H, and A, B and C are all H, and D and Z are both OH, then the compound is urolithin A. Preferably, the urolithin used in the methods of the present disclosure is urolithin A, urolithin B, urolithin C or urolithin D. Most preferably, the urolithin used is urolithin A.

Urolithin A

The present invention also encompasses use of suitable salts of compounds of formula (I), e.g. pharmaceutically acceptable salts. Suitable salts according to the invention include those formed with organic or inorganic bases. Pharmaceutically acceptable base salts include ammonium salts, alkali metal salts, for example those of potassium and sodium, alkaline earth metal salts, for example those of calcium and magnesium, and salts with organic bases, for example dicyclohexylamine, N-methyl-D-glucomine, morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyl-propylamine, or a mono-, di- or trihydroxy lower alkylamine, for example mono-, di- or triethanolamine.

In a further disclosure of the invention there is provided use of a compound of formula (I)

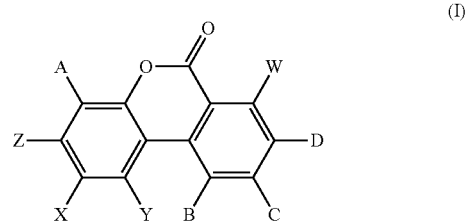

(I)

wherein:
A, B, C, D, W, X, Y and Z are each independently selected from H and OH; or a salt thereof;
wherein said compound of formula (I) is combined with at least one pharmaceutically acceptable carrier to form an oral solid dosage form, administered, preferably, once a day, wherein the compound is orally administered to a subject in a daily amount of from 2.8 to 6.0 mmol per day, over a period of at least 21 days.

In a further disclosure of the invention there is provided use of a compound of formula (I)

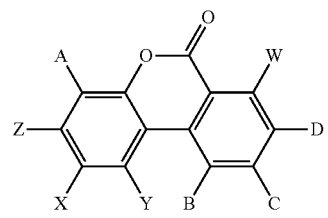

(I)

wherein:
A, B, C, D, W, X, Y and Z are each independently selected from H and OH; or a salt thereof;

wherein said compound of formula (I) is combined with at least one pharmaceutically acceptable carrier to form an oral solid dosage form, administered, wherein the compound or salt is orally administered at a dose sufficient to achieve steady state plasma levels of a compound of formula (I), and/or metabolites thereof, of 900-1350 ng/ml.

In a further disclosure of the invention there is provided use of a compound of formula (I) wherein: A, B, C, D, W, X, Y and Z are each independently selected from H and OH; or a salt thereof; wherein said compound of formula (I) is combined with at least one pharmaceutically acceptable carrier to form an oral solid dosage form, administered, wherein the compound or salt is orally administered at a dose sufficient to achieve steady state plasma levels of a compound of formula (I) and/or metabolites thereof, of 260-960 ng/ml.

Those skilled in the art of organic chemistry will appreciate that many organic compounds can form complexes with solvents in which they are reacted or from which they are precipitated or crystallized. These complexes are known as "solvates". It will be understood by the skilled person that the invention also encompasses solvates of the compounds of formula (I), as well as solvates of salts thereof. Solvates include those where the associated solvent is pharmaceutically acceptable. A hydrate (in which the associated solvent is water) is an example of a solvate.

Administration/Dosage Regimes

The methods of the present disclosure involve oral administration of a compound of formula (I) or salt thereof to a subject in a daily amount in the range of from 2.8 to 6.0 mmol per day, for at least 21 days. As discussed below, administration of 1000 mg urolithin A (which corresponds to about 4.4 mmol) results in a surprisingly good pharmacokinetic profile, compared with a much higher dosage of 2000 mg. It has also been found that repeated administration of a daily dosage of 1000 mg urolithin A over a number of weeks has surprisingly positive effects on biomarkers associated with mitophagy and muscle function.

The methods of the present disclosure involve daily administration of the compound of formula (I) or salt thereof, or of a composition containing the compound or salt. In some embodiments the compound or composition is administered once per day, i.e. the compound or composition is to be administered at least once per 24 hour period. In other embodiments the compound, or composition comprising the compound, is administered multiple times per day, for example twice per day, or three or four times per day. In such cases, the daily dosage is divided between those multiple doses. In one embodiment administration is once a day, in a second embodiment administration is twice a day, in a third embodiment administration is three times a day.

The methods of the present disclosure require daily administration of the compound of formula (I) or salt thereof, or of a composition containing the compound or salt, for at least 21 days. In some embodiments the method involves daily administration for a longer period of time, for example at least 28 days. As discussed below, daily administration of urolithin A to human subjects for 28 days has been shown to result in significant changes in biomarkers associated with improved mitochondrial function. In some embodiments, the methods may involve administration of the compound of formula (I), or salt thereof, over a still longer period of time, for example daily for at least 2 weeks, 3 weeks, 4 weeks, 5 weeks, 6 weeks, 8 weeks, 12 weeks, 4 months, 6 months, or for at least a year. In some embodiments, the method comprises administering the compound or salt thereof daily for a period of up to 3 months, up to 6 months, up to 1 year, up to 2 years or up to 5 years. In some embodiments, the method comprises administering the compound or salt daily for a period in the range of from 21 days to 5 years, from 21 days to 2 years, from 21 days to 1 year, from 21 days to 6 months, from 21 days to 12 weeks, from 28 days to 5 years, from 28 days to 2 years, from 28 days to 1 year, from 28 days to 6 months, from 28 days to 4 months, from 28 days to 12 weeks, 6 weeks to 2 years, from 6 weeks to 1 year, from 8 weeks to 1 year, or from 8 weeks to 6 months.

The methods of the present disclosure require daily administration of an amount of compound of formula (I) or salt thereof, of from 2.8 mmol per day up to 6.0 mmol per day thereof. In some embodiments, the daily amount administered is in the range of from 4.0 to 4.8 mmol. In some embodiments, the daily amount administered is approximately, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 mmol. In some preferred embodiments the method involves administration of approximately 4.4 mmol per day of the compound of formula (I) or salt thereof (e.g. of urolithin A). The exact weight of compound that is administered depends on the molecular weight of the compound that is used. For example, urolithin A has a molecular weight of 228 g/mol (such that 4.40 mmol is 1003.2 mg) and urolithin B has a molecular weight of 212 g/mol (such that 4.40 mmol is 932.8 mg).

In some embodiments the methods involve administration of urolithin A in an amount in the range of from 700 to 1300 mg/day, or in the range of from 750 to 1250 mg/day, or in the range of from 800 to 1200 mg/day, or in the range of from 850 to 1150 mg/day, or in the range of from 900 to 1100 mg/day. In a preferred embodiment the method involves administration of urolithin A in an amount in the range of from 950 to 1150 mg/day, more preferably approximately 1000 mg/day.

In some preferred embodiments, the methods involve administering urolithin A to the subject in an amount in the range of from 9 to 18 mg/kg/day such as 9 to 17 mg/kg/day. In another embodiment, the methods involve administering urolithin A to the subject in an amount in the range of from 10 to 17 mg/kg/day. In another embodiment, the methods involve administering urolithin A to the subject in an amount in the range of from 11 to 16 mg/kg/day.

The compound of formula (I) or salt thereof, or composition containing the compound of salt, may be administered at any suitable time, for example it may be administered in the morning after sleep or in the evening. In some embodiments it may be preferable for the method to be performed at approximately the same time(s) each day, for example within 15, 30, 60 or 120 minutes of a given time point.

In other embodiments, for example in the case of methods for improving muscle function and/or performance, body health, fitness, etc. in a subject, administration of the compound of formula (I) or salt thereof may for example be carried out shortly before or after exercise, e.g. within 15, 30 or 60 minutes before taking exercise, or after completing exercise.

In some embodiments, administration of the compound of formula (I) or the salt thereof to the subject results in a plasma pharmacokinetic profile comprising a $C_{max}$ of at least 1500 pg/mL. In some embodiments, administration of the compound of formula (I) or the salt thereof to the subject results in a plasma pharmacokinetic profile comprising a $C_{max}$ of at least 1550 pg/mL. In some embodiments, administration of the compound of formula (I) or the salt thereof to the subject results in a plasma pharmacokinetic profile comprising a $C_{max}$ of at least 1600 pg/mL. In some embodiments, administration of the compound of formula (I) or the salt thereof to the subject results in a plasma pharmacokinetic profile comprising a $C_{max}$ of at least 1650 pg/mL. In some embodiments, administration of the compound of formula (I) or the salt thereof to the subject results in a plasma pharmacokinetic profile comprising a $C_{max}$ of at least 1700 pg/mL, in some embodiments, administration of the compound of formula (I) or the salt thereof to the subject results in a plasma pharmacokinetic profile comprising a $C_{max}$ of at least 1750 pg/mL. In some embodiments, administration of the compound of formula (I) or the salt thereof to the subject results in a plasma pharmacokinetic profile comprising a $C_{max}$ of at least 1800 pg/mL. In some embodiments, administration of the compound of formula (I) or the salt thereof to the subject results in a plasma pharmacokinetic profile comprising a $C_{max}$ of at least 1850 pg/mL. In some embodiments, administration of the compound of formula (I) or the salt thereof to the subject results in a plasma pharmacokinetic profile comprising a $C_{max}$ of at least 1900 pg/mL. In one embodiment $C_{max}$ is in the range 2000 to 2500 pg/ml for a dose of 1000 mg. $C_{max}$ values in this section relate to the compound of formula (i) excluding its metabolites. In a further embodiment $C_{max}$ is in the range 1000 to 3000 pg/ml, such as 1500 to 2500 pg/ml, for example about 2000 pg/ml.

The term $C_{max}$ refers the maximum (or peak) concentration that a compound achieves after the compound has been administrated and before the administration of a second dose.

The term $T_{max}$ refers to the time between compound administration and the time $C_{max}$ is observed.

In some embodiments, administration of the compound of formula (I) or the salt thereof to the subject results in plasma 'steady state' levels of a compound of formula (I) excluding metabolites in the range 350 to 600 pg/ml, such as 400 to 550, such as 450 to 550 pg/ml, for example, 300 to 500 pg/ml. In one embodiment plasma 'steady state' levels of a compound of formula (I) excluding metabolites of about 480 pg/ml.

Most commonly, the compound or composition containing the compound will be self-administered, particularly where the subject is healthy. Administration by a doctor, nurse, or another individual such as a care-giver, is also contemplated.

On one embodiment, the compound of formula (I) is administered with food. In another embodiment of the invention the compound of formula (I) is administered without food.

Uses

As discussed below, daily oral of administration of urolithin A for 28 days at the indicated dosage levels to human subjects has been found to result in changes in expression levels of genes associated with autophagy & mitophagy, and fatty acid oxidation. Effects were also observed on acylcarnitines. These changes are associated with positive effects in improving mitochondrial function, improving cellular metabolism, and body function, especially muscle function.

Accordingly, the present disclosure is directed to uses of the compound of formula (I) or a salt thereof as a dietary supplement; to methods of increasing mitophagy and/or autophagy, improving mitochondrial function and/or improving cellular metabolism in a subject comprising administration of the compound of formula (I) or salt thereof; to methods of maintaining and/or improving muscle function and/or performance, body health, fitness, $ATP^{max}$, muscle ATP use, oxygen consumption, muscle bioenergetics, tolerance to exercise, recovery from exercise and/or endurance in a subject comprising administration of the compound of formula (I) or a salt thereof; and to methods of treatment and/or prophylaxis of a condition, disease or disorder in a subject comprising administration of the compound of formula (I) or a salt thereof.

In some embodiments the subject is a mammal, for example a non-human mammal, but more preferably the subject is a human. In some embodiments the subject is male. In some embodiments the subject is female. Whilst in certain embodiments the subject may be a child, in other more preferred embodiments the subject is an adult. In some embodiments, for example in the case of methods for treating conditions, diseases or disorders associated with old age, the subject may be at least 40, at least 45, at least 50, at least 55, at least 60, at least 65, at least 70, at least 75, at least 80, at least 85, or at least 90 years of age, for example in the range of from 40 to 90, from 45 to 90, from 50 to 90, from 55 to 90, from 60 to 90, from 50 to 80, or from 55 to 75 years of age. In other embodiments, for example where the method is for enhancing muscle performance (e.g. in an athlete), the subject may be for example in the range of from 18 to 50, from 18 to 40, or from 18 to 30 years of age.

In some embodiments the methods of the present disclosure are for treatment and/or prevention of medical conditions, i.e. where the subject is an individual that has a disease state or a medical condition or disorder, such as sarcopenia or sporadic inclusion body myositis. In some other embodiments the subject may have a pre-disease, pre-disorder or pre-condition state, for example they may not have symptoms which would result in being a classified as having a particular condition, but which would be indicative of the subject being likely to develop such a condition in the future. As referred to herein, a subject that has a disease, condition or disorder, is a subject that has symptoms and has either been diagnosed by a medical practitioner as having a disease, disorder or condition, or, if presented to a medical practitioner, would be diagnosed as having a disease, disorder, or condition.

However, in other embodiments, it is envisaged that the compound of formula (I) or salt thereof will be ingested by subjects who are not suffering from a particular disease or disorder. For example, the subject may be a healthy individual that wishes to ingest the compound of formula (I) as a dietary supplement to boost wellbeing, metabolism, and body health generally for example, increasing mitochondrial health and function and mitochondrial biogenesis. The subject may also be a healthy individual that wishes to ingest the compound of formula (I) to improve fitness levels, e.g. to supplement an exercise regime. Accordingly, in some embodiments the subject is healthy. As referred to herein, a healthy subject is a subject that does not have symptoms which, if presented to a medical practitioner, would be diagnosed as having a disease, disorder or condition.

In some embodiments, the present disclosure relates to the use of the compound of formula (I) or a salt thereof as a food ingredient, an active ingredient used in food, a dietary supplement, a nutritional supplement, and/or a health supplement.

In some embodiments, the present disclosure relates to methods for increasing mitophagy and/or autophagy, improving mitochondrial function, and/or improving cellular metabolism in a subject. The mitochondrion is a central organelle that can drive both cellular life, i.e. by producing energy in the respiratory chain, and death, i.e. by initiating apoptosis. More recently, it was demonstrated that dysfunctional mitochondria can be specifically targeted for elimination by autophagy, a process that has been termed mitophagy. Increasing mitophagy (the removal of dysfunctional mitochondria) is understood to lead to rejuvenation of mitochondria, and improvement in mitochondrial function.

In some embodiments the methods involve administration of the compound of formula (I) or salt thereof for decreasing the plasma level of one or more acylcarnitines in a subject.

As discussed above, in some embodiments the subject is not a subject that is suffering from a specific health condition. Instead, the subject may be a subject who wishes to remain healthy, or a subject who wishes to improve their fitness levels, e.g. with regard to improving muscle function/performance, exercise tolerance and/or endurance levels. Improved muscle performance is of particular interest to athletes. Thus in some embodiments the methods involve administration of a compound of formula (I) or a salt thereof for maintaining and/or improving muscle function and/or performance, body health, fitness, $ATP^{max}$, muscle ATP use, oxygen consumption, muscle bioenergetics, tolerance to exercise, recovery from exercise and/or endurance in a subject, for example, by improving skeletal mitochondrial health, function and biogenesis. The enhanced muscle performance may be one or more of improved muscle function, improved muscle strength, improved muscle endurance and improved muscle recovery.

Muscle performance may be sports performance, which is to say the ability of an athlete's muscles to perform when participating in sports activities. Enhanced sports performance, strength, speed, and endurance are measured by an increase in muscular contraction strength, increase in amplitude of muscle contraction, or shortening of muscle reaction time between stimulation and contraction. The term "athlete" refers to an individual who participates in sports at any level and who seeks to achieve an improved level of strength, speed, or endurance in their performance, such as, for example, body builders, bicyclists, long distance runners, and short distance runners. Enhanced sports performance is manifested by the ability to overcome muscle fatigue, ability to maintain activity for longer periods of time, and have a more effective workout.

The term $ATP^{max}$ refers to the phosphorylation capacity per unit volume of a tissue or organ of the body, such as tissue or muscle volume, and is a measure of mitochondrial function. Other indicators of muscle bioenergetics include muscle ATP use and oxygen consumption. Capacity for ATP generation ($ATP^{max}$) may for example be determined using $^{31}P$ magnetic resonance spectroscopy (MRS). Human subjects with low muscle strength or endurance have been shown to have low mitochondrial function using MRS. In some embodiments, the subject is a subject who, prior to commencement of administration of the compound of formula (I) or salt thereof, has low mitochondrial function, for example their $ATP^{max}$ level may be at least 5%, at least 10%, at least 15%, or at least 20% lower than the mean level in the population of subjects within the same age and sex group (e.g. within an age range of from 40-65, from 50 to 55, from more than 55 to 60, from more than 60 to 65, from more than 65, from more than 65 to 70, from more than 70 to 75, from more than 75 to 80, from more than 80 to 85, from more than 85 to 90 years of age and from more than 90 years of age).

Optical spectroscopy (OS) may for example be used to determine muscle oxygen consumption. In some embodiments, a light sensitive probe may be attached to a subject's hand or leg and measurements taken.

In some embodiments, the methods may be for improving physical endurance (e.g., ability to perform a physical task such as exercise, physical labor, sports activities), inhibiting or retarding physical fatigue, enhancing working capacity and endurance, reducing muscle fatigue, enhancing cardiac and cardiovascular function.

Muscle performance may, for example, be evaluated by measuring changes from baseline (e.g. values measured prior to commencement of administration of the compound of formula (I) or salt thereof) in muscle strength (maximum voluntary contraction) and/or endurance (duration of force production) determined from the results of exercise testing. A treadmill test, in which the time for a subject to reach a predetermined percentage of their maximum heart rate (e.g. 85%) may be used. A hand grip ergometer may be used to measure arm strength, e.g. as a measure of sarcopenia. A fatigue test, in which a subject is requested to pull against a force transducer to a predetermined percentage of their maximum voluntary contraction (e.g. 70%) at a predetermined rate, and in which the exercise rate is increased until the subject can no longer exercise, may be used.

In some embodiments, physical performance, and changes in physical performance, may be measured using the Short Physical Performance Battery test (SPPB). The SPPB is a tool designed to quantify physical performance. Measurements include balance, gait, ability to stand with feet together side-by-side, semitandem, and tandem positions, time to walk a pre-set distance (e.g. 8 feet), time to rise from a chair and return to the seated position a predetermined number of time (e.g. 5 times), hand grip, and distance covered in 6 minutes in a walk (see Guralnik et al, Journal of Gerontology, 1994, 49, No. 2, M85-M94).

In some embodiments, the methods are for treating, preventing and/or reducing the severity of a condition, disease or disorder. Age-related diseases pose a burden for both the elderly and society as a whole. In recent years, evidence has shown that dysfunction of mitochondria plays an important role in age related diseases, such as Alzheimer's and Parkinson's diseases, diabetes mellitus type 2, SIBM, intensive care-unit acquired muscle weakness (IC-UAW) and sarcopenia. During aging, there is a progressive decline in the cell capacity to eliminate its dysfunctional elements by autophagy, as evidenced by mutations in mitochondria and the decrease in autophagic flux.

In some embodiments, the methods are for the treatment and/or prophylaxis of a disease, disorder or condition associated with inadequate mitochondrial activity. In some embodiments, the methods are for the treatment and/or prophylaxis of a muscle-related disease, disorder or condition. In some embodiments, the methods are for the treatment and/or prevention of a disease, disorder or condition associated with old age.

Examples of relevant diseases, disorders and conditions associated with inadequate mitochondrial activity include obesity, reduced metabolic rate, metabolic syndrome, metabolic stress, diabetes mellitus (e.g. type II diabetes mellitus), cardiovascular disease, hyperlipidemia, memory decline, neurodegenerative diseases, cognitive disorder, mood disorder, stress, and anxiety disorder, fatty liver disease (for example NAFLD and NASH), for improving liver function and for weight management.

Further examples of relevant diseases, disorders and conditions include muscle-related pathological conditions include musculoskeletal diseases and disorders, musclewasting, muscle degenerative disease, myopathies, agerelated decline in muscle function, frailty, pre-frailty, neuromuscular diseases, such as Duchenne muscular dystrophy, sarcopenia (for example acute sarcopenia), inclusion body myositis (e.g. sporadic inclusion body myositis, SIBM). ICUAW, muscle atrophy and/or cachexia, for example associated with burns, bed rest, limb immobilization, or major thoracic, abdominal, neck and/or orthopedic surgery. Age-related muscle-loss is an especially prevalent condition. Cachexia due to prolonged immobilization or to other diseases, for example cancer, are other conditions that are often characterised by poor muscle performance. In one embodiment relevant diseases, disorders and conditions includes sarcopenia, cachexia, frailty and other muscle diseases.

Decreased mitochondrial function is associated with various health conditions associated with aging, e.g. joint health, muscle function, muscle loss, memory loss, vision loss and hearing loss. Examples of age-related diseases, disorders and conditions include a joint disorder, a muscle function disorder, memory loss, vision loss and/or hearing loss. In some embodiments, the subject may be suffering from age-related decline in muscle function, age-related sarcopenia, age-related muscle-wasting, physical fatigue, muscle fatigue, and/or is frail or pre-frail.

Further examples of diseases, disorders and conditions in which the methods of the present disclosure find utility in treating and/or preventing include inclusion body myositis (for example sporadic inclusion body myositis. SIBM), alcoholic liver disease, non-alcoholic fatty liver disease, drug-induced liver injury, acute and chronic diseases of the kidney and liver, such as acute or chronic kidney failure, acute or chronic toxicity induced by chemotherapy, such as cytotoxic chemotherapy e.g. cisplatin, (for example Nephrotoxicity, Neurotoxicity, Ototoxicity), drug-induced cravings, anaemia disorders, α1-antitrypsin deficiency, ischemia/reperfusion injury, inflammation, inflammatory bowel disease, Crohn's disease, osteoarthritis, Alzheimer's disease, Parkinson's disease, ulceration, amyotrophic lateral sclerosis, cancer, cognitive disorder, stress, mood disorder, improving cognitive function, weight management and/or increasing muscle and/or mental performance.

Further examples of disease include neurodegenerative diseases such as Alzheimer's disease, amyotrophic lateral sclerosis, Huntington's disease, and Parkinson's disease.

Good muscle performance is important for effective living at all stages of life, in healthy individuals as well as in those individuals suffering from a disease, especially the elderly. While it is natural to have a gradual decline in muscle mass and strength with aging (>60 years), a variety of environmental factors (diet, exercise, chronic diseases, polymedication) dictate whether with aging, elderly fall into healthy, pre-frail (i.e. decline in either muscle mass or function) or frailty (sarcopenia, i.e. >2 standard deviations decline in both muscle mass and function) groups. Amongst the elderly, more than 50 percent males and 25 percent females fall into pre-frail category. Around 10-20 percent of the pre-frail elderly population subsequently transitions into frail category as this population advances into the next decades of their lifetime. The health economic costs of maintaining pre-frail and frail syndrome amount to over 20 billion USD in costs to the society and healthcare systems In some embodiments, the methods are for improving, maintaining or reducing loss of muscle function. Without being bound by any particular theory, it is the understanding of the inventors that improved mitochondrial function is associated with improved muscle quality and hence improved functionality. Methods of the present disclosure may for example improve, maintain or reduce the loss of muscle function and endurance in individuals with a disease, including young and elderly individuals. Methods of the present disclosure may for example improve, maintain or reduce the loss of muscle function and endurance in healthy individuals, including athletes, non-athletic individuals, sedentary individuals and the elderly. For example, methods of the present disclosure may increase muscle strength as evidenced by the improvement of performing a physical activity, such as an exercise, for example, increased ability to lift weights or increased hand grip strength. Also, methods of the present disclosure may improve muscle structure, for example by increasing or maintaining muscle mass in conditions of normal muscle function, declining muscle function or impaired muscle function.

Improved muscle function can be particularly beneficial in elderly subjects with reduced muscle function as a result of an age-related condition. For example, a subject who may benefit from improved muscle function may experience a decline in muscle function which then leads to pre-frailty and frailty. Such subjects may not necessarily experience muscle wastage in addition to their decline in muscle function. Some subjects do experience both muscle wasting and a decline in muscle function, for example subjects with sarcopenia. The methods of the present disclosure may for example be used in enhancing muscle performance by administering the compound of formula (I) or salt thereof to a subject who is frail or to pre-frail.

The present disclosure further provides methods to improve the physical performance or endurance capacity as perceived by the subject, for example by the reduction of in perceived exertion or effort during exercise or an activity as determined using a self-reported questionnaire.

In some embodiments the methods involve administration of the compound of formula (I) or salt thereof for improving and/or maintaining skeletal muscle function and/or cardiac muscle function. In some embodiments the methods involve administration of the compound of formula (I) or salt thereof for improving and/or maintaining joint health. In some embodiments the methods involve administration of the compound of formula (I) or salt thereof for improving and/or maintaining mobility.

The subject may be a subject that wishes to feel more active/wakeful and less tired. Mitochondria assists in providing more ATP (energy) to cells). Accordingly, in some embodiments the methods involve administration of a compound of formula (I) or a salt thereof for improving wakefulness and/or decreasing tiredness/fatigue in a subject.

The methods also find use in the management of normal physiological function in healthy individuals of conditions characterised by poor physical performance, impaired endurance capacity, and impaired muscle function. The methods may improve physical performance in individuals with a disease, including young and elderly individuals. Methods of the present disclosure may improve physical performance, for example, short-term performance or long-term performance in healthy individuals, including athletes, non-athletic individuals, sedentary individuals and the elderly. This improvement of performance may be measured by the time spent to walk or run a certain distance (for example, an improved performance during the 6 minute walk test (MWT)), an improved time to run a certain distance, an improved IPAQ score on the international physical activity questionnaire, an increased number of chair-stands in a certain time, or another test designed to measure physical performance.

Methods of the present disclosure further provide for the improvement of endurance capacity. The endurance capacity refers to the time to fatigue when exercising at a constant workload, generally at an intensity <80% VO$_2$max. Methods of the present disclosure may improve endurance capacity in individuals with a disease, including young and elderly individuals. Methods of the present disclosure may improve endurance capacity in healthy individuals, including athletes, non-athletic individuals, sedentary individuals and the elderly. The present disclosure provides for a method of increasing the time to fatigue while performing a specific activity, for example, fitness training, walking, running, swimming, or cycling. This improvement of endurance capacity may be assessed with objective measurements (for example, speed, oxygen consumption or heart rate) or it can be self-reported measurements (for example, using a validated questionnaire).

Further Active Ingredients/Supplements

Whilst in some embodiments, the compound of formula (I) or salt thereof, may be administered as the sole active ingredient or dietary/nutritional/health supplement, in other embodiments the compound of formula (I) or salt thereof may be administered in combination with a further active ingredient or supplement. The compound of formula (I) or salt thereof and the further active ingredient or supplement may for example be administered simultaneously (either as part of the same composition, or in separate compositions, e.g. multiple tablets), sequentially, or separately (e.g. at different times during the day). The further above ingredient or supplement may for example be one which is suitable for use as a dietary, nutritional and/or health supplement; for increasing mitophagy and/or autophagy, for improving mitochondrial function and/or improving cellular metabolism; for maintaining and/or improving muscle function and/or performance, body health, fitness, muscle ATP$^{max}$, muscle mitochondrial function, oxygen consumption, muscle bioenergetics, muscle endurance, tolerance to exercise, recovery from exercise and/or endurance; or for treating or preventing a disease, disorder or condition associated with inadequate mitochondrial activity, for treating or preventing decline in muscle function during aging, frailty and/or sarcopenia. As another example, the further active ingredient or supplement may be one which is a suitable for improving muscle function and endurance when performing different athletic activities (e.g. running).

In some preferred embodiments, the compound of formula (I) is administered with a carnitine or a salt thereof. The term carnitine encompasses L-carnitine and derivatives thereof, including acetyl-L-carnitine (ALCAR) and propionyl L-carnitine. Salts of carnitines include tartrate salts, for example in the case of L-Carnitine L-tartrate (LCLT), and glycine salts, e.g. glycine propionyl-L-carnitine (GPLC). When used, carnitines may be administered by any suitable means or dosage form, but commonly carnitines are administered orally, and are dosed daily. Thus in some embodiments, the carnitine or salt thereof is administered daily to the subject by oral dosing, e.g. over a period of at least 21 days, or over a period of at least 28 days. In some embodiments the daily dosage of carnitine or salt thereof administered to the subject (e.g. orally) is in the range of from 0.5 to 50 mmol per day, or in the range of from 1 to 25 mmol per day, or in the range of from 2.5 to 15 mmol per day, or about 2, about 3, about 4, about 5, about 8, about 7, about 8, about 9, about 10, about 11, about 12, about 13, about 14, or about 15 mmol per day. For example, where the carnitine is L-carnitine, the daily dosage may for example be in the range of from 100 to 2000 mg per day, 100 to 250 mg per day, 250 to 500 mg per day, 250 to 1000 mg per day, 500 to 1000 mg per day, or 500 to 2000 mg per day. As another example, where the carnitine salt L-carnitine-L-tartrate is used, the daily dosage may for example be in the range of from 500 to 4000 mg per day, 1000 to 4000 mg per day, or 500 to 1000 mg per day. As a further example, where the carnitine is acetyl-L-carnitine, the daily dosage may for example be in the range of from 500 to 2500 mg per day. As yet another example, where the carnitine salt glycine propionyl-L-carnitine is used, the daily dosage may for example be in the range of from 500 to 4000 mg per day, 1000 to 4000 mg per day, or 500 to 1000 mg per day. The carnitine or salt thereof may be administered to the subject as a single daily dose, or alternatively it may be administered as multiple doses (e.g. two, three or four times daily), in which case the daily dose is divided between those multiple doses.

Compositions

The methods of the present disclosure involve oral administration of the compound of formula (I) or a salt thereof. Any suitable oral composition containing the compound of formula (I) or salt thereof may be used. The present methods encompass a variety of uses of the compound as, for example, a dietary, nutritional and/or health supplement; to maintain or improve muscle function and/or performance, fitness, tolerance to exercise and/or endurance; and as new therapies for treating or preventing muscle-related medical conditions and disorders. Accordingly, the use of a range of compositions which contain the compound of formula (I), and which are suitable for oral administration, is envisaged. Thus in some embodiments, the compound of formula (I), or salt thereof, is administered in the form of an oral composition containing the compound of formula (I) or salt thereof and one or more excipients suitable for oral administration. In some embodiments, the compound of formula (I) (e.g. urolithin A) may be included in a functional food, for example a health bar, or an energy bar for consumption post-exercise. It may for example be incorporated in a yoghurt. Alternatively, the compound may be included in a drink such as a milkshake, in a sports drink (e.g. providing electrolytes and/or sugars), or be present in a concentrate or powder form for making up into a drink. For example, it may for example be included in a complete nutrition product, e.g. which is shelf-stable. Examples of complete nutrition products include those sold under the trade names Boost® and Ensure®. In cases where the compound is intended for use as a dietary supplement or medicament, it may for example be present in a composition having the form of a pill, tablet, capsule, caplet, lozenge, pastille, granules, powder for suspension, oral solution, oral suspension, oral emulsion, syrup, or the like. In some embodiments, the compound may be included in a composition for enteral/tube feeding, for example in the case of subjects who are unable to feed themselves and/or having compromised of impaired gastrointestinal function. Enteral feeding refers to the delivery of a nutritionally complete feed, e.g. containing protein, carbohydrate, fat, water, vitamins and minerals to the stomach. Examples of types of enteral feeding products include those fed by nasogastric and J-tubes. Examples of enteral feeding products include Peptamen® (Nestle Health) and Vital 1.5® (Abbott). Conventional ingredients/excipients used in the production of such compositions (e.g. functional foods, snack bars, drinks, medicinal dosage forms, enteral feeding compositions etc.) may be used.

Compositions containing the compound of formula (I) may take any physical form suitable for the intended application, for example, they may be in the form of a solid (for example a bar), a semi-solid (for example a softgel), or a liquid (including to emulsions). In some instances, the composition may be in the form of a viscous fluid or a paste. Where the composition is a bar, for example, it may be of any suitable type and it may contain ingredients conventionally used for the preparation of snack bars. Semi-solid forms may likewise contain excipients conventional in the art. The excipients can, for example, provide a desired hardness, shelf-life and flavour such that the composition has an acceptable taste, an attractive appearance and good storage stability. Semi-solid forms can be in the form of a paste. Where the composition is a softgel, it may for example be provided in a capsule having a shell. The shell may be of a conventional type, for example it may be a soft gelatin-based shell. By way of example, the composition may also be provided inside a hard capsule type of shell. Liquid compositions may be in the form of a medicine, a dietary supplement, or a beverage, each for oral consumption. Liquid formulations may be solutions, emulsions, slurries or other semi-liquids. Excipients in a liquid composition can, for example, provide a shelf-life, visual appearance, flavour and mouthfeel such that the composition has an acceptable taste, an attractive appearance and good storage stability. At certain levels of dilution, a drink may need to be shaken before the subject drinks it, so as to maintain an even suspension of the active ingredient.

In some preferred embodiments, the method comprises administration of a compound of formula (I) or salt thereof (e.g. urolithin A), in micronized form. Micronization enables the compound of formula (I) to disperse or dissolve more rapidly. Micronisation can be achieved by methods established in the art, for example compressive force milling, hamermilling, universal or pin milling, or jet milling (for example spiral jet milling or fluidised-bed jet milling) may be used. Jet milling is especially suitable. If micronized compound is used, then preferably the compound has a $D_{50}$ size of under 100 µm—that is to say that 50% of the compound by mass has a particle diameter size of under 100 µm. More preferably, the compound has a $D_{50}$ size of under 75 µm, for example under 50 µm, for example under 25 µm, for example under 20 µm, for example under 10 µm. More preferably, the compound has a $D_{50}$ in the range 0.5-50 µm, for example 0.5 to 20 µm, for example 0.5 to 10 µm, for example 1.0 to 10 µm, for example 1.5 to 7.5 µm, for example 2.8 to 5.5 µm. Preferably, the compound has a $D_{90}$ size of under 100 µm. More preferably, the compound has a $D_{90}$ size of under 75 µm, for example under 50 µm, for example under 25 µm, for example under 20 µm, for example under 15 µm. The compound preferably has a $D_{90}$ in the range 5 to 100 µm, for example 5 to 50 µm, for example 5 to 20 µm, for example 7.5 to 15 µm, for example 8.2 to 16.0 µm. Preferably, the compound has a $D_{10}$ in the range 0.5-1.0 µm. Preferably, the compound of formula (I) or salt thereof (e.g. urolithin A) has a $D_{90}$ in the range 8.2 to 16.0 µm, a $D_{50}$ in the range 2.8 to 5.5 µm and a $D_{10}$ in the range 0.5 to 1.0 µm.

Compositions Comprising the Compound of Formula (I) or Salt Thereof, and a Medium Chain Triglyceride In some preferred embodiments, the compound of formula (I) or salt thereof (e.g. urolithin A) is administered in the form of a composition comprising: a) a medium-chain triglyceride; and b) the compound of formula (I) or salt thereof. Within those embodiments, preferably the compound of formula (I) (e.g. urolithin A) is in micronized form.

By selecting suitable medium chain triglycerides and excipients, the physical form of the composition can be tailored to the requirements of the product in question. For example, in some embodiments the compositions may be pharmaceutical compositions. In some embodiments the compositions may be nutritional compositions.

Compositions containing a compound of formula (I) or salt thereof (e.g. urolithin A) and a medium chain triglyceride advantageously exhibit a single peak in terms of their plasma pharmacokinetic profile following oral dosing, compared with simple saline suspensions which display a delayed second increase in blood level some time after the initial peak. When administering bioactive compounds orally, it is preferable that the plasma concentration of the compound presents as a single peak rather than as a multiple peak profile.

In many cases, compositions containing a compound of formula (I) and a medium chain triglyceride have the consistency of a viscous liquid or paste, and can be provided as a single serving supplement to a subject's general diet (for example in a bar, gel, or a softgel capsule, hard capsule, or diluted in a drink); alternatively, it can be provided as a part of or the whole of a meal.

Where the methods of the disclosure involve use of a composition comprising a medium-chain triglyceride, the medium-chain triglyceride typically makes up at least 1% w/w of the composition, for example at least 5% w/w, for example at least 10% w/w, for example at least 15% w/w. The medium-chain triglyceride preferably makes up 20% w/w or more of the composition, for example 25% w/w or more by weight, for example 30% w/w or more by weight of the composition. For example the medium-chain triglyceride may make up 1-40% w/w of the composition, 2-40% w/w of the composition, 5-40% w/w of the composition; 10-40% w/w of the composition; 1-99% w/w of the composition, 5-99% w/w of the composition, 10-99% w/w of the composition, 20-99% w/w of the composition, 5-90% w/w of the composition, 10-90% w/w of the composition, for example 20-90% w/w of the composition, 20-80% w/w of the composition for example, 30-80% w/w of the composition, for example 30-70% w/w of the composition, for example 30-60% w/w of the composition, for example 30-50% w/w of the composition, for example 30-40% w/w of the composition, for example 30-35% w/w of the composition. For example the medium-chain triglyceride may make up 40-70% w/w of the composition, for example 50-70% w/w of the composition, for example, 55-65% w/w of the composition.

In such compositions, the compound of formula (I) typically makes up from 0.1 to 80% w/w of the composition, for example 0.1 to 60% w/w, for example 0.25 to 50% w/w. For example the compound of formula (I) may make up 0.5-50% w/w of the composition. If the composition is provided as a part or the whole of a meal then the compound of formula (I) may for example make up 0.25-5% w/w of the composition, for example, 0.3-3% w/w of the composition. If the composition is provided as a single serving supplement to a subject's general diet, then the urolithin typically makes up from 20 to 80% w/w of the composition, for example 20 to 40% w/w, for example 25 to 35% w/w of the composition. For example the urolithin may make up 26-34% w/w of the composition, for example, 28-33% w/w of the composition; for example, 29-32% w/w of the composition, for example 29-31% w/w of the composition.

In such compositions, the weight ratio of the medium-chain triglyceride component to the compound of formula (I) is generally in the range 0.01:1 to 100:1, for example 0.5:1 to 100:1, for example 0.5:1 to 50:1, for example 0.5:1 to 5:1; or, for example, 1:1 to 75:1, for example 1:1 to 50:1, for example 1:1 to 20:1, for example 1:1 to 10:1, for example 1:1 to 2.5:1, for example 1:1 to 2:1, for example 1:1 to 1.5:1. The weight ratio may be in the ratio 0.01:1 to 10:1, for example 0.1:1 to 10:1 or 0.01:1 to 5:1, for example 0.01:1 to 0.1:1.

In some preferred embodiments, the method of the present disclosure involves administration of a softgel capsule comprising a filling, which filling comprises the compound of formula (I) or salt thereof (e.g. urolithin A) and one or more medium-chain triglycerides. Within those embodiments, preferably the compound of formula (I) or salt thereof (e.g. urolithin A) is micronized. In embodiments where a softgel capsule is used, the shell component may be produced using conventional ingredients.

Medium-chain triglycerides are compounds of formula $CH_2(OR^1)$—$CH(OR^2)$—$CH_2(OR^3)$ where $R^1$, $R^2$ and $R^3$ are medium chain fatty acid groups, generally of formula —$C(=O)(CH_2)_n CH_3$ where n is in the range 4 to 10, for example 6 to 8. Medium-chain fatty acids are fatty acids which have an aliphatic tail of 6-12 carbon atoms. The aliphatic tail is predominantly saturated. Particular medium-chain fatty acids include caproic acid (hexanoic acid, C6:0), caprylic acid (octanoic acid, C8:0), capric acid (decanoic acid, C10:0) and lauric acid (dodecanoic acid, C12:0). Myristic acid (tetradecanoic acid, C14:0) can also be present in minor amounts. Medium-chain triglycerides most commonly used generally have a mixture of triglycerides of caprylic acid and capric acid, and contain 95% or greater of saturated fatty acids.

The medium chain triglyceride component present in preferred compositions used in the methods of the present disclosure may consist of a homogeneous, single medium chain triglyceride compound type; more commonly, the medium chain triglyceride component is a mixture of two or more different medium chain triglyceride compounds.

The European Pharmacopoeia describes medium-chain triglycerides as the fixed oil extracted from the hard, dried fraction of the endosperm of *Cocos nucifera* L. (coconut) or from the dried endosperm of *Elaeis guineenis* Jacq. (African oil palm). The European Pharmacopoeia and the USPNF both have specifications for medium-chain triglycerides that require the presence of particular fatty acids is as follows: caproic acid (C6) 52.0%; caprylic acid (C8) 50.0-80.0%; capric acid (C10) 20.0-50.0%; lauric acid (C12)≤3.0%; and myristic acid (C14)≤1%.

Medium-chain triglycerides for use in preferred compositions comprise a mixture of triglycerides with fatty acid chains present in the following proportions: C6≤5%; C8 50-70%; C10 30-50%; and C12≤12%, for example C6≤0.5%; C8 55-65%; C10 35-45%; and C12≤1.5%.

Medium-chain triglycerides used in the preferred compositions may be derived from any known or otherwise suitable source.

Compositions used in the methods of the present disclosure may, advantageously, comprise one or more phospholipids. A particularly preferred phospholipid is phosphatidylcholine. The advantages brought about by phosphatidylcholine may be due, at least in part, to their amphipathic nature, e.g. due to properties as an emulsifier.

A particularly useful source of phospholipids, in particular phosphatidylcholine, is lecithin, and compositions used in the methods of the present disclosure advantageously comprise lecithin. Lecithin, when present in compositions, typically makes up at least 0.5% w/w of the composition, preferably at least 1% w/w of the composition. The lecithin preferably makes up 10% w/w or more of the composition, for example 20% w/w or more by weight, for example 30% w/w or more by weight of the composition. For example the lecithin may make up 0.5-80% w/w of the composition, for example 1-80% w/w, for example 20-80% w/w, for example 40-80% w/w, alternatively for example 0.5-75% w/w of the composition, for example, 1-40% w/w of the composition, for example 30-40% w/w of the composition, for example 30-35% w/w of the composition, for example, 30-75% w/w of the composition. Alternatively, the lecithin may make up 0.5-5% w/w of the composition, for example 1-5% w/w of the composition, for example 1-3% w/w of the composition, for example, 0.5-2% w/w of the composition, for example, 1-2% w/w of the composition. The weight ratio between the lecithin, when present, and the urolithin is generally in the range 0.02:1 to 3:1, for example, 0.03:1 to 1.2:1, for example 1:1 to 1.2:1, for example 1.1:1 to 1.2:1.

'Lecithin' designates any group of fatty substances occurring in animal and plant tissues including phosphoric acid, choline, fatty acids, glycerol, glycolipids, triglycerides, and phospholipids (e.g., phosphatidylcholine, phosphatidylethanolamine, and phosphatidylinositol). Commercial lecithin obtained from soya and sunflower comprises the phospholipids phosphatidyl choline, phosphatidyl inositol, phosphatidyl ethanolamine, and phosphatidic acid. Lecithin may be obtained by chemical extraction from its source in a non-polar solvent such as hexane, ethanol, acetone, petroleum ether or benzene, or by mechanical extraction. In particular, lecithin may be obtained by extraction from sources including soybeans, eggs, milk, rapeseed, cottonseed and sunflower. Commercial lecithin for use in edible formulations may be readily purchased.

Commercially produced lecithin, which may be used in compositions described herein, typically contains the following major components: 33-35% soybean oil, 20-21% inositol phosphatides, 19-21% phosphatidylcholine, 8-20% phosphatidylethanolamine, 5-11% other phosphatides, 5% free carbohydrates, 2-5% sterols and 1% moisture.

Commercially produced lecithin, which may be used in compositions described herein, may for example be enriched with phosphatidylcholine, having a minimum of 5% w/w phosphatidylcholine in the lecithin, for example, having a minimum of 10% w/w phosphatidylcholine in the lecithin, for example, having a minimum of 15% w/w phosphatidylcholine in the lecithin, for example, having a minimum of 20% w/w phosphatidylcholine in the lecithin, for example, having a minimum of 25% w/w phosphatidylcholine in the lecithin, for example, having a minimum of 30% w/w phosphatidylcholine in the lecithin, for example, having a minimum of 32% w/w phosphatidylcholine in the lecithin, for example, having a minimum of 40% w/w phosphatidylcholine in the lecithin.

Lecithins may also be modified by one or more of the following processes to tailor their properties: alcohol extraction of particular phospholipids to produce a lecithin with a modified ratio of differing phospholipids; acetone extraction to remove oil, resulting in a powdered or granulated phospholipid blend; spray drying onto proteins as carriers; spray cooling with synthetic emulsifiers such as high melting mono- and di-glycerides to produce flaked or powdered products; modification by enzyme action (phospholipases, commonly in particular phospholipase A2), in particular partial hydrolysis to produce lecithins with pronounced emulsifying behaviour; hydrolysis of fatty acid groups by acids and alkali; acetylation; and hydroxylation of fatty acid chains and amino groups.

In some embodiments, the methods comprise administration of a composition comprising a compound of formula (I) or salt thereof, a medium chain triglyceride, and an emulsifier (e.g. lecithin).

Where the method of the present disclosure involves administration of a composition comprising the compound of formula (I) and a medium chain triglyceride (and optionally an emulsifier such as lecithin), the composition may for example contain additional components. The additional components may for example be compounds that provide health benefits, for example selected from vitamins, minerals, proteins, polyunsaturated fatty acids, and other compounds.

Amongst vitamins, there may specifically be mentioned Vitamin A, Vitamin C, Vitamin D, Vitamin E, Vitamin B12 and Vitamin K2. As used herein, "vitamin D" refers, to any of known form of vitamin D, and specifically includes vitamin D2 (ergocalciferol), vitamin D3 (cholecalciferol), vitamin D precursors, metabolites and another analogues, and combinations thereof, as well as the various active and inactive forms of vitamin D. For example, vitamin D3 may be provided in its unhydroxylated inactive form as cholecalciferol, or may be provided in its hydroxylated active form as calcitriol.

Creatine has been described as having beneficial effects in the treatment of muscle disorders. It can be included in composition of the invention. β-hydroxyl-β-methylbutyrate (HMB) has been described as having beneficial effects in the treatment of muscle disorders. It can be included in compositions.

Polyunsaturated fatty acids are fatty acids that contain more than one double bond in the backbone. This class includes many important compounds, such as essential fatty acids, e.g., omega-3 and omega-6 fatty acids. Long chain polyunsaturated fatty acids are suitable, and preferably those having at least 20 carbon atoms in the molecule. Such long chain omega-3 fatty acids include cis-11, 14, 17-eicosatrienoic acid (ETE) C20:3, cis-8, 11, 14, 17-eicosatetraenoic acid (ETA) C20:4, cis-5,8, 11, 14, 17-eicosapentaenoic acid (EPA) C20:5, cis-7, 10, 13, 16, 19-docosapentaenoic acid (DPA, Clupanodonic acid) C22:5, cis-4, 7, 10, 13, 16, 19-docosahexaenoic acid (DHA) C22:6, cis-9, 12, 15, 18,21-tetracosapentaenoic acid C24:5; cis-6,9, 12, 15, 18,21-tetracosahexaenoic acid (Nisinic acid) C24:6. Long chain omega-6 fatty acids having at least 20 carbon atoms include cis-11, 14-eicosadienoic acid C20:2, cis-8, 11, 14-eicosatrienoic acid (Dihomo-gamma-linolenic acid) (DGLA) C20:3, cis-5,8, 11, 14-eicosatetraenoic acid (Arachidonic acid) (AA) C20:4, cis-13, 16-docosadienoic acid C22:2, cis-7, 10, 13, 16-docosatetraenoic acid (Adrenic acid) C22:4, cis-4, 7, 10, 13, 16-docosapentaenoic acid (Osbond acid) C22:5. The composition according to the invention preferably contains EPA, DHA or a combination of them, for example in an amount from 10 to 1,000 mg per serving; for example in an amount from 25 to 250 mg per serving.

Pharmaceutical compositions containing the compound of formula (I) or salt thereof may for example include additional pharmaceutically active compounds.

In some exemplary embodiments, the compositions of the present invention may comprise, in addition to medium-chain triglycerides and a compound of formula (I), one or more additional macronutrients, e.g. fat and/or carbohydrate. Non-limiting examples of suitable fats or sources thereof for use in the compositions described herein include coconut oil; fractionated coconut oil; soy oil; corn oil; olive oil; safflower oil; high oleic safflower oil; sunflower oil; high oleic sunflower oil; palm and palm kernel oils; palm olein; canola oil; marine oils; cottonseed oils; polyunsaturated fatty acids such as docosahexaenoic acid (DHA), arachidonic acid (ARA), eicosapentaenoic acid (EPA); and combinations thereof. Non-limiting examples of suitable carbohydrates or sources thereof for use in the compositions described herein may include maltodextrin, hydrolyzed or modified starch or cornstarch, glucose polymers, corn syrup, corn syrup solids, rice-derived carbohydrates, glucose, fructose, lactose, high fructose corn syrup, tapioca dextrin, isomaltulose, sucromalt, maltitol powder, glycerin, fructooligosaccharides, soy fiber, con fiber, guar gum, konjac flour, polydextrose, honey, sugar alcohols (e.g., maltitol, erythritol, sorbitol), and combinations thereof. Maltodextrin, sucrose and fructose are especially preferred.

Additional components in a composition may be compounds that do not provide health benefits to the subject, but instead improve the composition in some other way, for example its taste, texture or shelf-life as mentioned above. The composition may thus further contain one or more compounds selected from emulsifiers, colorants, preservatives, gums, setting agents, thickeners, sweeteners and flavourings.

Suitable emulsifiers, stabilisers, colorants, preservatives, gums, setting agents and thickeners are well known in the art of manufacture of emulsions and other semi-liquids. Emulsifiers may include one or more of phosphatidylcholine, lecithin, polysorbates such as polysorbate 60 or polysorbate 80 (Tween-60 and Tween-80), and glycerol monostearate (GMS). Glycerol monostearate is also known as glyceryl monostearate.

Stabilisers may be used in a composition described herein. Many compositions are stable suspensions without the need for an added stabiliser. A stable suspension is one that does not undergo a phase separation over time. For certain compositions, the stability can be improved by inclusion of an added stabiliser. Suitable stabilisers for use in compositions of the invention include glycerol monostearate (GMS), silicon dioxide and vegetable shortening. An exemplary stabiliser is GMS and preferred compositions of the invention contain GMS. Its properties also make GMS a good solvent for phospholipids, such as found in lecithin for example. GMS exists in two polymorphs: the α-form is dispersible and foamy, useful as an emulsifying agent or preservative. The α-form is suitable for wax matrices. The α-form is converted to the β-form when heated at 50° C.

GMS falls into two distinct grades: 40-55 percent monoglycerides, and 90 percent monoglycerides, 40-55 percent monoglycerides as defined by the European Pharmacopoeia describes GMS as a mixture of monoacylglycerols, mostly monostearoylglycerol, together with a quantity of di- and tri-glycerols. In particular, the 40-55 grade contains 40-55% monoacylglycerols, 30-45% diacylglycerols, and 5-15% of triacylglycerols. The 99 percent grade contains not less than 90% of monoglycerides. The monoglycerides in commercial GMS products are mixtures of variable proportions of glyceryl monostearate and glyceryl monopalmitate. The European Pharmacopoeia further divides glyceryl monostearate 40-55 into three types according to the proportion of stearic ester in the mixture. Type 1 contains 40.0-60.0% stearic acid, and the sum of palmitic and stearic acids is ≤90%. Type 2 contains 60.0-80.0% stearic acid, and the sum of palmitic and stearic acids is ≤90%. Type 3 contains 90.0-99.0% stearic acid, and the sum of palmitic and stearic acids is ≤96%. Any form of GMS may be used in the compositions.

In some embodiments, the method comprises administration of a composition comprising a medium chain triglyceride, the compound of formula (I) or a salt thereof (e.g. urolithin A), and a stabiliser, for example glycerol monostearate. In some embodiments the method involves administration of a composition comprising an emulsifier and a stabiliser.

Metal chelators or sequestrants such as sodium calcium salts of ethylenediamine tetra acetic acid (EDTA) may also be used. Other components that may be included in formulations of the invention include polyethylene glycols, silicon dioxide, vegetable shortening and beeswax.

A flavouring may be beneficial in compositions used in the methods described herein. In a liquid or semi-liquid composition, fruit flavour can be provided for example by inclusion of a fruit sauce or puree. Typical flavorings include strawberry, raspberry, blueberry, apricot, pomegranate, peach, pineapple, lemon, orange and apple. Generally, fruit flavorings include fruit extract, fruit preserve or fruit puree, with any of a combination of sweeteners, starch, stabilizer, natural and/or artificial flavors, colorings, preservatives, water and citric acid or other suitable acid to control the pH.

A unit dose composition used in the methods described herein preferably contains 250 mg or 500 mg of the compound of formula (I), for example 250 mg or 500 mg of urolithin A. A unit dose may for example be in the form of a snack bar, e.g. of weight in the range of from 25 g to 150 g, in the form of a drink provided in a container such as a bottle or pouch sufficient to hold a single dose (e.g. 50 to 500 ml, 100 to 300 ml, for example, 250 ml or 500 ml). In a further alternative example, which is preferred, the unit dose is in the form of a softgel capsule, e.g. containing 250 mg of urolithin A.

A representative composition is shown in the Table below:
Representative Composition A:

| Composition | Per 100 g |
| --- | --- |
| Medium Chain Triglycerides | 10-85 g |
| Urolithin A | 10-50 g |
| Lecithin (comprising minimum phosphatidylcholine content of 32% w/w) | 10-50 g |
| Glycerol Monostearate | 0-5 g |

A further representative composition is shown in the Tables below:
Representative Composition B:
Soft Gel Capsule Containing Gelatin Shell and Fill Containing Urolithin A

| Fill | | |
| --- | --- | --- |
| Ingredients | Amount (mg)/Cap | % Total |
| Urolithin A | 250 | 22.73% |
| Lecithin NF (35% Total PC) (Epikuron 135 F IP)-E322 | 284.25 | 25.84% |
| Medium Chain Triglycerides (MCT) | 284.25 | 25.84% |
| Glycerol Monostearate (40-55) EP, Mono- and Diglycerides NF | 11.5 | 1.06% |
| Fill Weight | 830 mg | 75.47% |

| Shell | | |
| --- | --- | --- |
| Ingredients | Amount (mg)/Cap | % Total |
| Gelatin EP, NF | 165.97 | 15.09% |
| Glycerol-E422 | 80.01 | 7.27% |
| Water | 21.62 | 1.96% |
| Titanium Dioxide EP-E171 | 1.96 | 0.18% |
| DualDustmaster FD&C Blue #1 (Brilliant Blue FCF-E133) | 0.234 | 0.021% |

| Shell | | |
|---|---|---|
| Ingredients | Amount (mg)/Cap | % Total |
| Sodium Copper Chlorophyllin Powder (min 95%)-E141 | 0.196 | 0.018% |
| Shell Weight | 270 mg | 24.539% |
| Total Capsule Weight | 1100 mg | 100% |

The present disclosure provides uses of the compound of formula (I) or a salt thereof, methods involving administration of the compound of formula (I) or salt thereof, a compound of formula (I) or salt thereof for use as a medicament, and use of a compound of formula (I) or salt thereof for the manufacture of a medicament for treating a condition in a subject. The above discussion, and the embodiments described therein (e.g. in relation to the nature of the compounds of formula (I), dosage regimes, applications, and compositions) has been made in the context of discussing methods of the present disclosure but applies equally to all aspects of the present disclosure, including those aspects relating to uses of the compound of formula (I) or a salt thereof, the compound of formula (I) or salt thereof for use as a medicament, and use of the compound of formula (I) or salt thereof for the manufacture of a medicament for treating a condition in a subject.

EXAMPLES

The following Examples illustrate the invention.

Example 1: Preparation of Urolithin A

Urolithin A (4) was prepared in two steps starting from 2-bromo-5-methoxybenzoic acid 1 and resorcinol 2. The pure compound was obtained as a pale yellow powder.

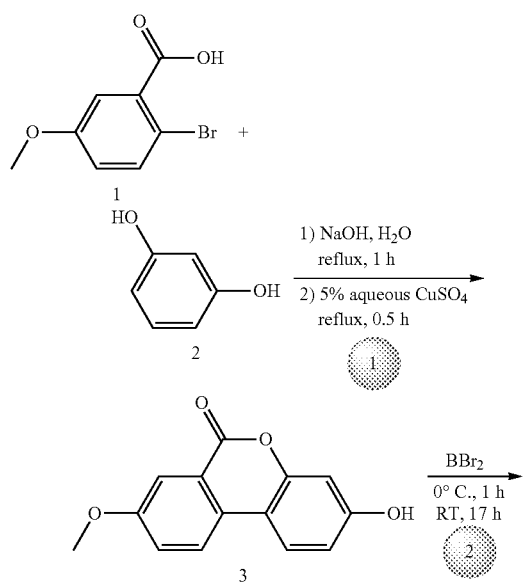

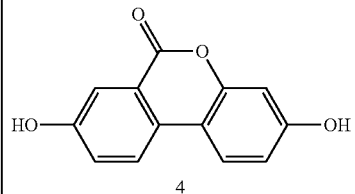

Step 1:

A mixture of 2-bromo-5-methoxybenzoic acid 1 (27.6 g; 119 mmol; 1.0 eq.), resorcinol 2 (26.3 g; 239 mmol; 2.0 eq.) and sodium hydroxide (10.5 g; 263 mmol; 2.2 eq.) in water (120 mL) was heated under reflux for 1 hour. A 5% aqueous solution of copper sulphate (3.88 g of $CuSO_4 \cdot 5H_2O$ in 50 mL water; 15.5 mmol; 0.1 eq.) was then added and the mixture was refluxed for additional 30 minutes. The mixture was allowed to cool to room temperature and the solid was filtered on a Büchner filter. The residue was washed with cold water to give a pale red solid which was triturated in hot MeOH. The suspension was left overnight at 4° C. The resultant precipitate was filtered and washed with cold MeOH to yield the title compound 3 as a pale brown solid.

Step 2:

To a suspension of 3 (10.0 g; 41 mmol; 1.0 eq.) in dry dichloromethane (100 mL) was added dropwise at 0° C. a 1 M solution of boron tribromide in dry dichloromethane (11.93 mL of pure $BBr_3$ in 110 mL of anhydrous dichloromethane; 124 mmol; 3.0 eq.). The mixture was left at 0° C. for 1 hour and was then allowed to warm up to room temperature. The solution was stirred at that temperature for 17 hours. Then ice was added thoroughly to the mixture. The yellow precipitate was filtered and washed with cold water to give a yellow solid which was heated to reflux in acetic acid for 3 hours. The hot solution was filtered quickly and the precipitate was washed with acetic acid, then with diethyl ether to yield the title compound 4 as a yellow solid. $^1H$ and SC NMR were in accordance with the structure of 4.

Example 2: Urolithin A Dosage Form

Urolithin A was formulated into a soft gel capsule containing the following components:

| Fill | | |
|---|---|---|
| Ingredients | Amount (mg)/Cap | % Total |
| Urolithin A | 250 | 22.73% |
| Lecithin NF (35% Total PC) (Epikuron 135 F IP)-E322 | 284.25 | 25.84% |
| Medium Chain Triglycerides (MCT) | 284.25 | 25.84% |
| Glycerol Monostearate (40-55) EP, Mono- and Diglycerides NF | 11.5 | 1.06% |
| Fill Weight | 830 mg | 75.47% |

| Shell | | |
|---|---|---|
| Ingredients | Amount (mg)/Cap | % Total |
| Gelatin EP, NF | 165.97 | 15.09% |
| Glycerol-E422 | 80.01 | 7.27% |
| Water | 21.62 | 1.96% |
| Titanium Dioxide EP-E171 | 1.96 | 0.18% |
| DualDustmaster FD&C Blue #1 (Brilliant Blue FCF-E133) | 0.234 | 0.021% |
| Sodium Copper Chlorophyllin Powder (min 95%)-E141 | 0.196 | 0.018% |
| Shell Weight | 270 mg | 24.539% |
| Total Capsule Weight | 1100 mg | 100% |

Example 3: Clinical Study

A single (Part A) and multiple (Part B) dose study of urolithin A was conducted to evaluate the safety, tolerability, pharmacokinetics and pharmacodynamics profile in healthy elderly subjects.

Study Design

Part A: The study was a double-blind, randomized, single ascending doses, study in 24 healthy elderly male and female volunteers. Each subject was randomized for two subsequent doses in three cohorts.

Part B: The study was a double-blinded, randomized, multiple ascending dose study in 36 healthy elderly male and female volunteers. Each subject was randomised to receive study product or placebo for 28 days.

Study Objectives:

To determine the safety and tolerability of urolithin A in healthy elderly subjects following multiple 28 days dosing.

To determine the pharmacokinetic profiles of urolithin A following a single and a multiple dose.

To compare the pharmacokinetic profiles of urolithin A delivered as soft gel formulation in a single 250 mg dose to ascending single higher doses administration at doses: 500 mg, 1000 mg and 2000 mg.

To compare the pharmacokinetic profiles of urolithin A delivered as a softgel formulation in repeated multiple 28 days 250 mg dose to ascending repeat multiple 28 days administration at doses: 500 mg and 1000 mg.

To determine dose-dependent pharmacodynamics modulation of gene and protein expression for autophagy and mitophagy biomarkers in muscle tissue (vastus lateralis) compared to baseline, following multiple dose 28 days oral administration of urolithin A (250 mg, 500 mg, 1000 mg doses).

Investigational Product:

1100 mg soft gel capsule containing 250 mg of urolithin A (as described in Example 2 above). Soft gel capsules were blister-packed in bulk, Labelling was in accordance with local regulatory specifications and requirements.

Dose Per Intake:

Part A: 250 mg, 500 mg, 1000 mg or 2000 mg (1, 2, 4 or 8 capsules)

Part B: 250 mg per day, 500 mg per day or 1000 mg per day (1, 2, or 4 capsules per day)

Placebo:

Soft gel capsule containing lecithin, triglycerides, diglycerides

Timing for Intake:

Part A: Single oral dose administration on D1 of each period according to the randomisation. The administration took place around 8:00 am with around 200 mL tap water, in sitting position, and under fasting conditions.

Part B: Repeated oral dose administration from day 1 to day 28 according to the randomization. The administration took place around 8:00 am with around 200 mL tap water, in a sitting position, and under fasting conditions.

Subjects:

Part A:

24 healthy elderly male and female subjects were included in the study, within the age range 61 to 85 years.

Cohort 1 (8 subjects): 250 mg urolithin A (6 subjects) or placebo (2 subjects) capsule soft gel formulation then 2000 mg urolithin A or placebo capsule soft gel formulation.

Cohort 2 (8 subjects): 500 mg urolithin A (6 subjects) or placebo (2 subjects) capsule soft gel formulation.

Cohort 3 (8 subjects): 1000 mg urolithin A (6 subjects) or placebo (2 subjects) capsule soft gel formulation.

Part B:

36 healthy elderly male and female subjects were included in the study, within the age range 61 to 85 years.

Cohort 1 (12 subjects): 250 mg urolithin A (9 subjects) or placebo (3 subjects) soft gel capsule formulation for 28 days.

Cohort 2 (12 subjects): 500 mg urolithin A (9 subjects) or placebo (3 subjects) soft gel capsule formulation for 28 days.

Cohort 3 (12 subjects): 1000 mg urolithin A (9 subjects) or placebo (3 subjects) soft gel capsule formulation for 28 days.

Pharmacokinetics Parameters:

After single dosing: $C_{max}$, $t_{max}$, $AUC_{0-t}$, $AUC_{0-\infty}$, $t_{1/2}$ After multiple dosing: $C_{max}$, $t_{max}$, $AUC_{0-24h}$, $t_{1/2}$ From the plasma concentration-time data, the following pharmacokinetic parameters will be determined, as data permit using non-compartmental methods: maximum observed plasma concentration ($C_{max}$) (ng/mL), time at which maximum observed plasma concentration ($t_{max}$) (h), area under the plasma concentration-time curve $AUC_{(0-24h)}$ (ng/mL*h) and $AUC_{(0-\infty)}$ (ng/mL*h), and apparent terminal phase half-life ($t_{1/2}$) (h).

Study Duration

Part A:

Screening within 21 days prior to the first administration.

Hospitalization for 48 h (D-1 evening to D2 evening) for each period.

Ambulatory visit at D4 and D5 for each period

Wash-out: at least 21 days between each administration

End of study visit: P2D5.

Follow up phone call at P2D7 (±2).

Expected duration: approximately 8 weeks for each participating subject

Part B:

Screening within 21 days prior to the first administration

Ambulatory visits at day −1 (V1), day 7 (V2), day 14 (V3).

Hospitalisation from day 27 (V4) (around 4 pm) to day 29 (V6) (around 10 am)

Ambulatory visit at day 31 and day 32 for each period

Follow up phone call at day 35 (+/−2)

Expected duration: approximately 8 weeks for each participating subject.

During the last visit, subjects underwent a complete clinical biological examination, identical to an examination at the start of the study. Any (AEs) were recorded, and if they were ongoing a further follow-up was arranged. Follow up continued until the event was resolved or the condition was unlikely to change or the subject was lost to follow-up.

Randomization

A randomisation list was provided by the sponsor's representative. The product was allocated at P1D1 for part A and on D-1 (V1) on part B.

Blinding

The following measures were taken to avoid bias:
double-blind study; and
soft-gel capsules containing active product and placebo were indistinguishable in appearance.

The analytical centre as well as the Investigator and the team and the subject were in blind conditions. For each subject, a coding list containing the identification of the product (emergency envelopes) was supplied by the sponsor's representative and kept in a safe place during the whole clinical study period. In the case of a pharmaceutical preparation being required, the decoding system used was a sealed coding list to be given to the representative's pharmacist. The sealed coding list was kept in a safe place and was accessible to any person authorised to unblind.

Statistics

Laboratory Parameters (Biochemistry/Haematology/Urinalysis)

Values, position according to laboratory range and clinical assessment were described at screening, study baseline (D-1), and at the end of study (D28) by dose group and overall. Change between the value at study baseline and the value at the end of study visit was described for each parameter by dose group and overall. All quantitative and qualitative urinary test results were listed, sorted by dose group, subject and visit.

Methods and Timing for Assessing, Recording, and Analysing Pharmacokinetic Parameters Collection, Treatment and Storage of Blood Samples Blood sampling was performed for urolithin A concentration measurements at the exact timepoints with an authorised time window described in the table below:

Part A:

| Day | Sampling time | Sample N° | Time window(min) |
|---|---|---|---|
| 1 | T0 (predose) | P00 | |
| | T1 h 00 | P01 | +/−2 |
| | T2 h | P02 | +/−2 |
| | T4 h | P03 | +/−4 |
| | T6 h | P04 | +/−5 |
| | T8 h | P05 | +/−5 |
| | T12 h | P06 | +/−5 |
| 2 | T24 h | P07 | +/−5 |
| | T36 h | P08 | +/−5 |
| 4 | T72 h | P09 | +/−15 |
| 5 | T96 h | P10 | +/−15 |

Part B:

| Day | Sampling time | Sample N° | Time window(min) |
|---|---|---|---|
| D-1 | T0 h (predose) | P00 | |
| D7 | T0 h (predose) | P01 | |
| D14 | T0 h (predose) | P02 | |
| 28 | T0 (predose) | P03 | |
| | T1 h | P04 | +/−2 |
| | T2 h | P05 | +/−2 |
| | T4 h | P06 | +/−3 |
| | T6 h | P07 | +/−5 |
| | T8 h | P08 | +/−5 |
| | T12 h | P00 | +/−5 |
| 29 | T24 h | P10 | +/−5 |
| 31 | T72 h | P11 | +/−5 |
| 32 | T96 h | P12 | +/−5 |

Blood Handling Procedures:

At each time point indicated in the table, a 6 mL blood sample was drawn into K2-EDTA coated tube. The blood samples were gently inverted a few times for complete mixing with the anticoagulant. The exact time of sample collection was recorded on the eCRF. Within 30 minutes following blood collection, each blood sample was centrifuged at 1500 g for 10 minutes at 4° C.

Within 30 minutes after the centrifugation, the top layer of human plasma will be transferred into two pre-labelled polypropylene tubes, containing approximately 1500 μL of plasma each (2 aliquots per time point).

Blood cells were not transferred. All sample tubes were clearly and appropriately labelled. Tubes were capped immediately from each time point and the plasma were frozen in an upright position at approximately −80° C. for storage. The samples were shipped on dry ice.

Plasma Samples Transport:

Samples were sent to laboratory for analysis of pharmacokinetic parameters. The shipment was done in dry ice by a specialized carrier. Temperatures were monitored using data logger during all transport.

Methods and Timing for Assessing, Recording, and Analysing Muscle Biopsy

Muscle biopsies were collected before the meal from the vastus lateralis muscle of the right leg in order to perform ex vivo measurements.

Part B:

| Day | Sampling time | Sample N° |
|---|---|---|
| −1 | Pre-dose (before the meal) | VL00 |
| 28 | Pre-dose (before the meal) | VL01 |

Muscle biopsies were collected on Day −1 and Day 28 at pre-dose under fasted state using the Bergström biopsy needle technique. The minimal amount of each muscle tissue sample was approximately 50 mg. One third of the tissue was used for gene expression (≈50 mg), and was further divided into two equal portions: one portion for RNA analysis (≈25 mg) and one portion for DNA analysis (≈25 mg), both in a Safe-lock Tubes 2.0 ml, Eppendorf (part no. 0030.120.094). Muscle tissue was snap frozen using liquid nitrogen immediately after collection and further, long term storage will be in a −80° C. freezer. The mRNA was analysed by microarray. Quantification of mtDNA over nuclear DNA provided another measure of mitochondrial abundance. The shipment was done in dry ice by specialized carrier. Temperatures were monitored using data logger during all transport.

Measurement of Metabolites and Markers of Muscle Function in Plasma

Collection, Treatment and Storage of Blood Samples

Blood sampling was performed for analysis on plasma at the exact time-points described in the table below:

Part B:

| Day | Sampling time | Sample No. |
| --- | --- | --- |
| −1 | T0 (predose) | IL00 |
| 28 | T0 (predose) | IL01 |

Blood handling procedures: at each time point indicated in the table, a 6 mL blood sample was drawn into K2-EDTA coated tube. The blood samples were gently inverted a few times for complete mixing with the anticoagulant. The exact time of sample collection was recorded on the eCRF. Within 30 minutes following blood collection, each blood sample was centrifuged at 1500 g for 10 minutes at 4° C. 30 minutes after the centrifugation, the top layer of human plasma was transferred into 2 pre-labelled polypropylene tubes, containing approximately 1500 μL of plasma. Blood cells were not transferred. All sample tubes were clearly and appropriately labelled. Tubes were capped immediately from each time point and the plasma was be frozen in an upright position at approximately −80° C. for storage.

Blood Samples Transport: Samples were sent to Indivumed GmbH for analysis of muscle-related markers and to Metabolon Inc for the measurement of metabolites. The shipment was done using dry ice by a specialized carrier. Temperatures were monitored using data logger during all transport.

Measurement of markers of muscle function: Markers of muscle function, including myostatin and follistatin, were measured using an ELISA based method.

Myostatin is a plasma growth factor which inhibits muscle growth and differentiation. Higher plasma myostatin levels are indicative of muscle atrophy and poor function. Follistatin is a plasma growth factor that regulates muscle growth and differentiation by antagonizing myostatin. Higher plasma follistatin levels are indicative of improved muscle mass and function. Thus the balance or ratio between myostatin and follistatin is a key biomarker of muscle mass and function, with lower myostatin/follistatin ratios being indicative of better muscle mass and function, and higher myostatin/follistatin ratios being indicative of worse muscle mass and function.

Measurement of metabolites: Samples were extracted and split into equal parts for analysis on the LC/MS/MS and Polar LC platforms. Proprietary software was used to match ions to an in-house library of standards for metabolite identification and for metabolite quantitation by peak area integration. A total of 781 metabolites were quantified.

Diet and Study Restriction(s)

For part A, on Day 1 of each period, and on Day 28 for part B, the subjects were allowed to eat at the following times relative to study product administration: —T5 h standardized lunch; —T12 h standardized dinner.

Meals were taken after the PK sampling, if any. On the other hospitalization days, a standardized breakfast was served. Water supply was between 1.5 and 2 L for each 24-hour period. During the hospitalization, the subject was restricted to indoor activities (no exercise), rest and did not leave the Clinical Pharmacology Unit. Outside the hospitalization times, the subject was requested to follow a stable lifestyle throughout the duration of the trial with no sport activity. Throughout the duration of the study, the consumption of nicotine was prohibited. The consumption of the following supplements: resveratrol, nicotinamide riboside, whey protein, leucine, iso-leucine, L-carnitine, creatinine, Q10, vitamin A, niacin, folic acids, vitamin C, vitamin E, botanical extracts (including pomegranate and fruits extract) and probiotic-foods and supplements was stopped at least two weeks before inclusion.

Sampled Blood Volume

The total amount of blood collected during the study will be approximately:

Part A:

Total volume: 223 mL

Part B:

Total volume: 161 mL

Statistics

Description of the Statistical Methods

The statistical analysis consisted of individual data listings and descriptive statistics performed by the Sponsor's representative, using the SAS® computer program (release 9.3). In each part, all placebo subjects of 3 cohorts were pooled together in a placebo dose group.

Part A 4 dose groups were considered:

1—placebo,
2—250-2000 mg (250 mg at P1 and 2000 mg at P2),
3—500 mg,
4—1000 mg.

Part B:

4 dose groups were considered:

1—placebo,
2—250 mg,
3—500 mg,
4—1000 mg.

Descriptive Statistics

Descriptive statistics for quantitative parameters were provided using mean, Standard Deviation (SD), Standard Error of the Mean (SEM), minimum, median, maximum, and number of observations, and descriptive statistics for qualitative parameters will be provided using frequencies (n) and percent frequencies (%).

Subject Demographic Characteristics, Medical History and Diagnoses

Continuous variables (age, height, weight, BMI and qualitative variables (race) were summarized in descriptive statistics on the included subjects and/or pharmacokinetic population, if relevant. Subjects' consumption habits (smoking, alcohol, dietary habits) will be listed. Results of laboratory screen (drug abuse), serology and alcohol breath test, IPAQ were summarized by dose group and overall. Medical history will be listed and summarized by system organ class and preferred term, if relevant (Medical Dictionary for Regulatory Activity (MedDRA)). Abnormal physical findings at baseline were listed.

Previous Medications

Previous medications were coded according to the World Health Organization-Drug Reference List (WHO-DRL).

Baseline Safety Parameters

Individual safety data (clinical laboratory, vital signs, ECG) measured before the first product administration were checked for validity of entrance criteria, and abnormalities documented. Individual abnormalities before dosing were flagged in data listings and presented along with post-dose measurements in the statistical appendices.

Study Product and Concomitant Therapy

Study product dispensing information and details of product dosing (actual products/treatment received, actual dose received, date and time of product intake) for each subject were listed by dose group, period and subject. Concomitant treatments were coded according to the World Health Organization-Drug Dictionary (WHO-DD). Subjects who received concomitant treatments along with the dose group were listed by dose group, period and subject. If relevant, concomitant medications were also summarized by anatomic class and therapeutic class for dose group and period subjects, presenting the frequency of subjects (n) taking a given medication and the number of occurrence of each medication.

Analysis of Pharmacokinetics Parameters

From the plasma concentration-time data, the following pharmacokinetic parameters were determined, as data permit using non-compartmental methods: maximum observed plasma concentration ($C_{max}$), time at which maximum observed plasma concentration ($t_{max}$), area under the plasma concentration-time curve $AUC_{(0-24h)}$ and $AUC_{(0-\infty)}$, and apparent terminal phase half-life ($t_{1/2}$).

Analysis of Pharmacodynamics Parameters

Analysis of mRNA and RNA by Microarray

The method used has been validated according to good clinical laboratory practices (GCLP) and ICH guideline Q2(R1) (Validation of analytical procedures) by the corresponding service provider. Every sample was analysed in at least technical duplicates for housekeeping and target genes. A Ct value (threshold cycle), corresponding to the cycle at which the fluorescence signal reaches the amplification phase, was determined for every technical replicate and gene. The method of the $2^{-\Delta\Delta Ct}$ (Livak, K., J., and Schmittgen, T. D., Methods, 2001) was then applied to determine the relative expression of each target gene.

Gene expression on available remaining muscle tissues samples was performed by microarrays. Microarray data was analyzed running a Gene Set Enrichment type of Analysis (GSEA), which tells which biological processes are up or downregulated at the scale entire gene-sets, rather than gene by gene.

Analysis of Markers of Muscle Function

Every sample was analysed in technical duplicates together with a standard curve made with each isolated analyte. The amount of each marker was expressed as an absolute concentration in plasma (pg to µg/ml of plasma, depending on the analyte).

Quality Control and Assurance

Quality Assurance

The study was carried out in conformity with legal conditions and French regulations, and with respect to GCP (ICH E6). The Quality Assurance system in force at the Sponsor's Representative was applied, except for any specific clauses added to the protocol or specified in writing by the Sponsor before the start of the study.

Quality Control

The main study stages (coherence between source and CRF for eligibility criteria, main evaluation criteria, AEs) underwent a quality control process.

Sponsor Audits and Inspections by Regulatory Agencies

The study was subject to possible on-site audit visit by the Sponsor and inspection by applicable Regulatory Authorities in order to verify the study was conducted in compliance with the principles of GCP and with the study protocol. The auditor/inspectors would have had direct access to medical records, source documents, and all documents and facilities relevant to the clinical trial. The Investigator agreed to allow the auditors/inspectors to have direct access to study records for review, being understood that these personnel were bound by professional secrecy, and as such would not disclose any personal identity or personal medical information. The confidentiality of the data verified and the anonymity of the subjects should be respected during these inspections.

Ethical Considerations:

The study was carried out in accordance with the Declaration of Helsinki as modified in Fortaleza (2013), the recommendation on Good Clinical Practice (GCP) (ICH E6) and any applicable local regulatory requirement(s). The clinical study was started following receipt of the approval of both the Ethics Committee "Comite de Protection des Personnes" (CPP) and the French/National Health Authorities "Agence Nationale de securite du medicament et des produits de sante" (ANSM).

Example 4: Clinical Study Results

A Phase I clinical trial to determine pharmacokinetic and pharmacodynamics properties of urolithin A when dosed to human subjects was carried out as described in Example 3 above. The pharmacokinetic parameters of the compound when administered at different doses were investigated, as were the effects of urolithin A on muscle and plasma biomarkers.

In Part A of the study, human subjects were administered placebo or urolithin A orally as a single dose, at various dosage amounts. In Part B, human subjects were administered placebo or urolithin A orally, daily for 28 days, at various dosage amounts. In Part B skeletal muscle biopsies and plasma samples were taken and analysed using a range of techniques to determine effects on biomarkers.

a) Pharmacokinetics—Single Dose

FIG. 1 summarises certain plasma pharmacokinetic parameters of urolithin A following single dose oral administration at 250 mg, 1000 mg, and 2000 mg urolithin A dosages. As can be seen from the Table of FIG. 1, the 1000 mg dosage achieved the best pharmacokinetic profile of those three dosages, having a $C_{max}$ of 1920 pg/mL, and an AUC out to 36 hours of 15800 pg·h/mL. Surprisingly, the plasma levels of urolithin A when dosed at 2000 mg were lower than those achieved at the 1000 mg dosage, with a recorded $C_{max}$ of 1040 pg/mL and $AUC_{0-36h}$ of 12400.

Figure 3:
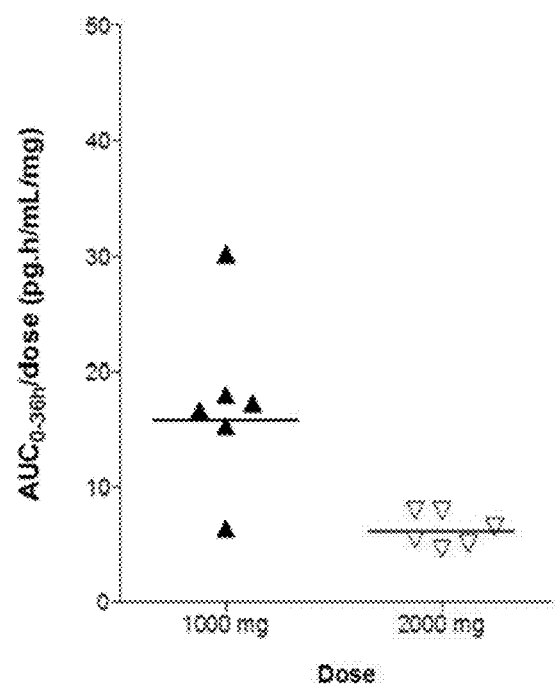
FIG. 3 shows a chart summarising dose-normalized individual and mean values for plasma $AUC_{0-36h}$ of Urolithin A following oral administration of a single dose of 1000 mg or 2000 mg urolithin A to healthy elderly subjects.

FIGS. 2 and 3 respectively present the individual and mean Cm and AUC se data for the 1000 mg and 2000 mg cohorts with the values normalised relative to the dosage amount. As can be seen, higher plasma levels of urolithin A were observed per mg dosed for the 1000 mg dosage compared with the 2000 mg dosage.

b) Pharmacokinetics—28 Day Dosing

Figures 4, 5:
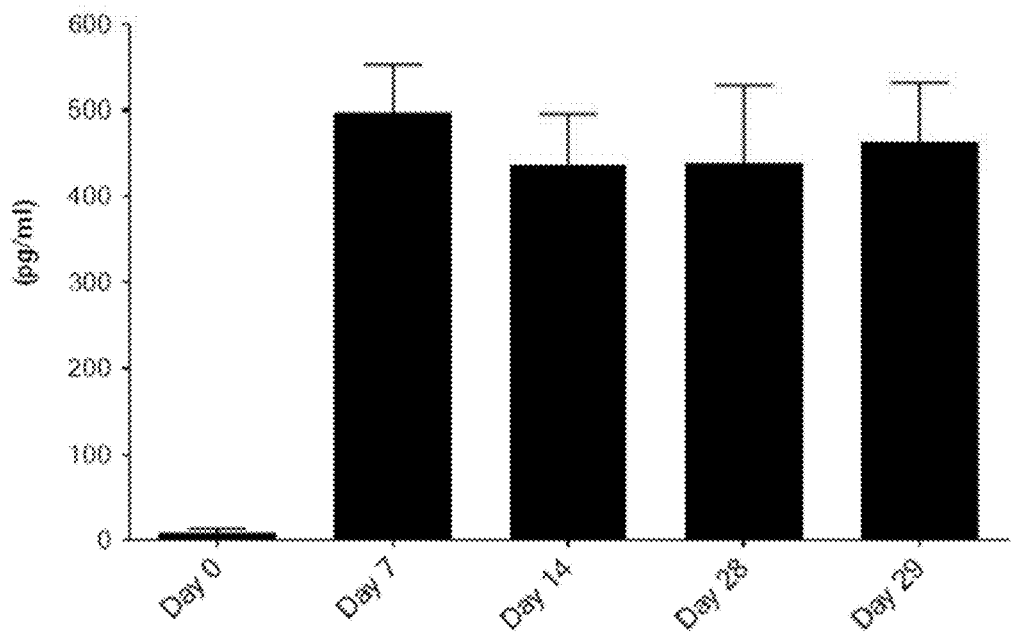
FIG. 4 shows a table summarising plasma pharmacokinetic variables for urolithin A in healthy elderly subjects at day 28 following daily oral administration of 1000 mg urolithin A for 28 days.
FIG. 5 shows a chart summarising mean plasma concentrations of urolithin A in healthy elderly subjects dosed with 1000 mg urolithin daily for 28 days art particular timepoints, i.e. 0, 7, 14, 28, 29 days. The day 0 measurement was pre-dose. The remaining measurements were taken 24 hours after administration of the previous day's dose (i.e. shortly before administration of the next daily dosage for days 7, 14 and 28).

FIG. 4 summarises certain plasma pharmacokinetic parameters of urolithin A at day 28, following oral administration for 28 days of a daily dosage of 1000 mg urolithin A. As can be seen from the Table, the mean values are comparable to those obtained following single dose administration of the compound, with a mean $C_{max}$ of 1970 pg/mL being obtained, and an AUC out to 24 hours of 17500 pg·h/mL.

Figure 6:
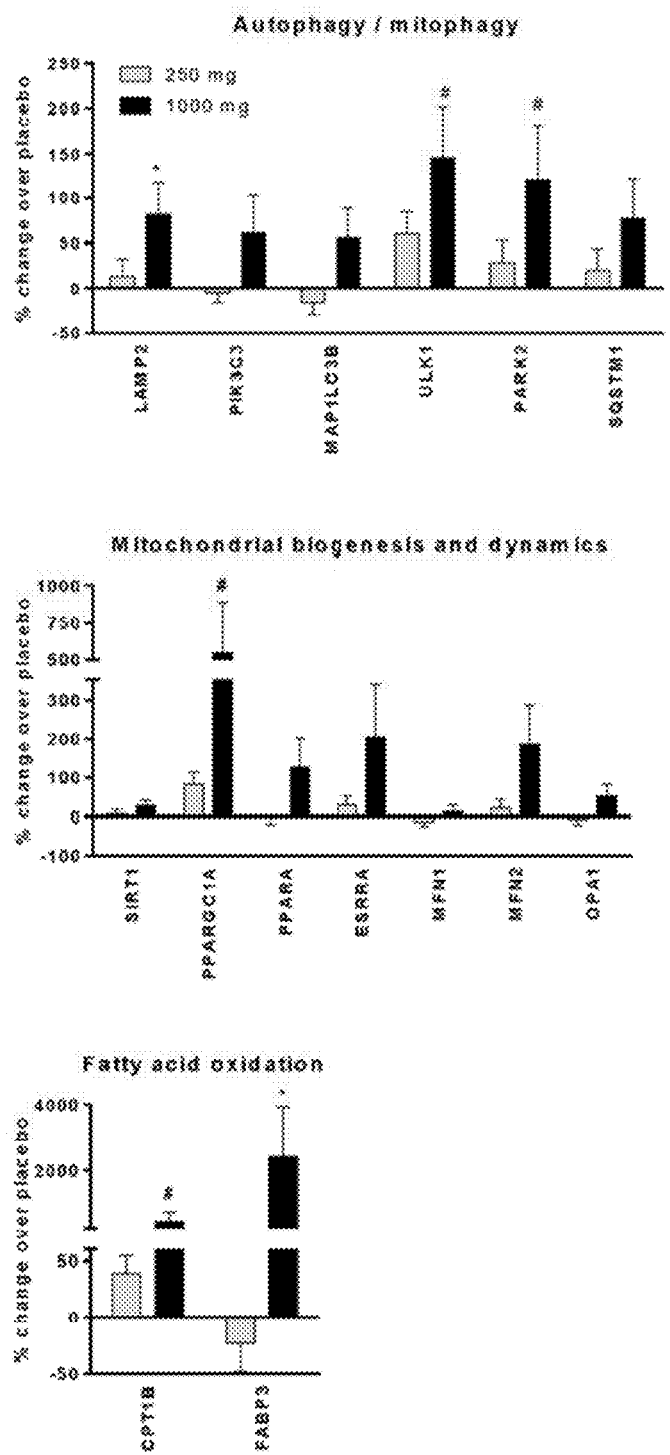
FIG. 6 shows bar charts showing fold-change in gene expression levels at day 28 over day −1 for specific genes associated with autophagy & microphagy, mitochondrial biogenesis and dynamics, and fatty acid oxidation for cohorts of subject administered 250 mg/day or 1000 mg/day urolithin A. The results are reported as % change over placebo.

FIG. 5 shows mean plasma concentrations of urolithin A in healthy elderly subjects dosed 500 mg/day urolithin A for 28 days, with plasma concentrations being measured at day 0, 7, 14, 28 and 29. The day 0 measurements were taken before the subject was dosed urolithin A. The other measurements were taken 24 hours after the previous dose of urolithin A was administered. The data in FIG. 5 demonstrates that the pharmacokinetic profile of the 500 mg daily dosage of urolithin A was stable over the 28 day period.

c) rtPCR Analysis of Gene Expression Levels in Skeletal Muscle Biopsies rtPCR analysis was carried out on skeletal muscle biopsies of human subjects administered urolithin A or placebo daily for 28 days to determine the expression levels of specific genes associated with autophagy and mitophagy (LAMP2, ULK1, PIK3C3, MAP1LC3B, SQSTM1, PARK2), mitochondrial biogenesis and dynamics (SIRT1, PPARGC1A, PPARA, ESRRA, MFN1, MFN2, OPA1), and fatty acid oxidation (CPT1B, FABP3). FIG. 6 provides bar graphs showing the fold-change in gene expression levels from day −1 to day 28 for each gene for patients administered 250 mg/day or 1000 mg/day urolithin A, over placebo.

The bar graphs represent gene expression data, expressed as a percentage of change over placebo, i.e. a value of 0% means that there is no difference between the dose and the placebo group while a value of 100% means that there is an increase in 100% over placebo value. Treatment with 1000 mg/day urolithin A resulted in upregulation of genes associated with autophagy, mitochondrial function, and/or fatty acid oxidation.

\* represents $P<0.05$ after a Dunnett post-hoc test, subsequent to an ANOVA test. As can be seen, there was significant upregulation of the autophagy/mitophagy-related gene LAMP2 and the fatty acid oxidation-related gene FABP3.

\# is used for values that are close to significant. For Ulk1, ANOVA p value=0.0524; Dunnett post-hoc p value=0.0180 for comparison of 1000 mg vs placebo. For Park2, ANOVA p value=0.2504; Dunnett post-hoc p value=0.1500 for comparison of 1000 mg vs placebo. For Ppargc1a, ANOVA p value=0.1026; Dunnett post-hoc p value=0.0673 for comparison of 1000 mg vs placebo. For Cpt1b, ANOVA p value=0.1362; Dunnett post-hoc p value=0.0805 for comparison of 1000 mg vs placebo.

d) Microarray Analysis of Gene Expression in Skeletal Muscle Biopsies of Human Subjects Administered Urolithin A.

Microarray analysis was carried out on skeletal muscle biopsies of human subjects administered urolithin A or placebo daily for 28 days. Approximately 30,000 gene transcripts were quantified by microarray in muscle biopsies and compared (day 28 vs. day −1). Gene Set Enrichment Analysis was conducted on 6166 gene sets.

FIGS. 7 and 8 show the level of enrichment in expression level of muscle and mitochondrial gene sets in vastus lateralis of subjects respectively at day 28 vs. day −1 (pre-dose) for the 1000 mg urolithin A cohort compared with placebo, for subjects treated for 28 days with urolithin A. The data represent the normalized enrichment score (NES) of 9 subjects in the group. A threshold of False Discovery Rate (FDR)<0.25 was applied to filter the genesets. Mitochondrial and muscle gene sets were significantly upregulated in the muscle tissue following administration of urolithin A.

Figure 9:
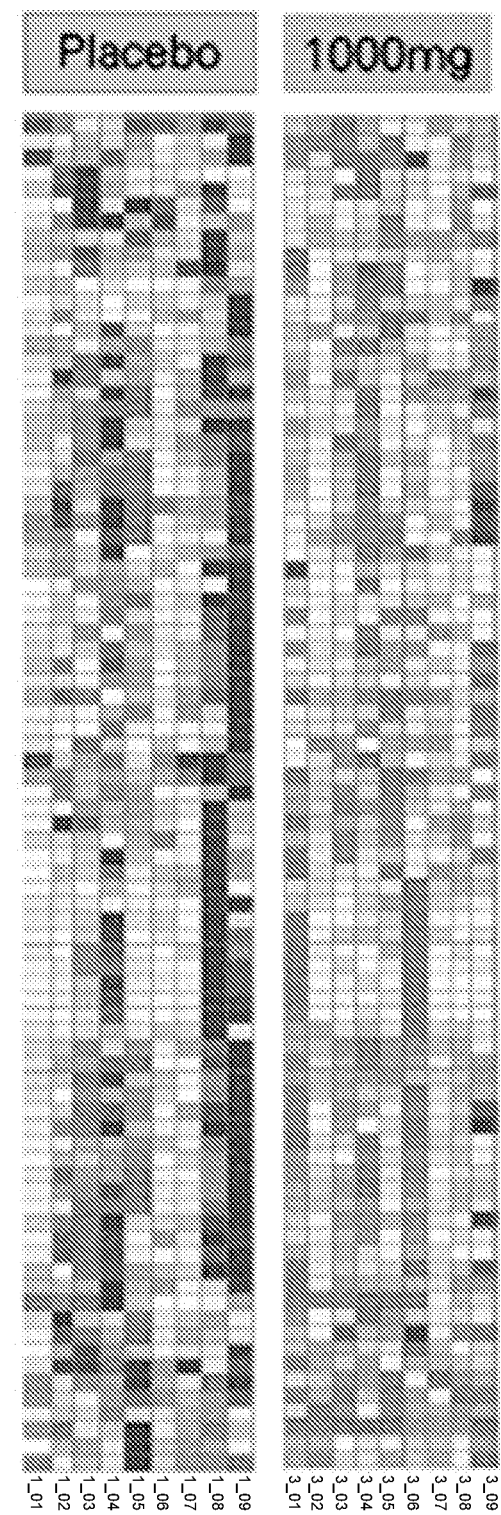
FIG. 9 shows heatmap representations of the change in expression level of genes in the geneset GO_MITOCHONDRION for groups of subjects administered either 1000 mg urolithin A or placebo per day for 28 days, after 28 day treatment.

Heatmap representations of the change in expression level of genes in the geneset GO_MITOCHONDRION for the groups of subjects administered 1000 mg urolithin A or placebo per day for 28 days, after 28 day treatment, are shown in FIG. 9. GO_MITOCHONDRION is the sixth geneset referred to in the table of FIG. 8. In FIG. 9, the heatmaps represent the same mitochondrial genes (in rows) across the different studies and groups of subjects (in columns). The enrichment in GO_MITOCHONDRION genes expression is significant in the 1000 mg urolithin A group vs the placebo group.

Figure 10:
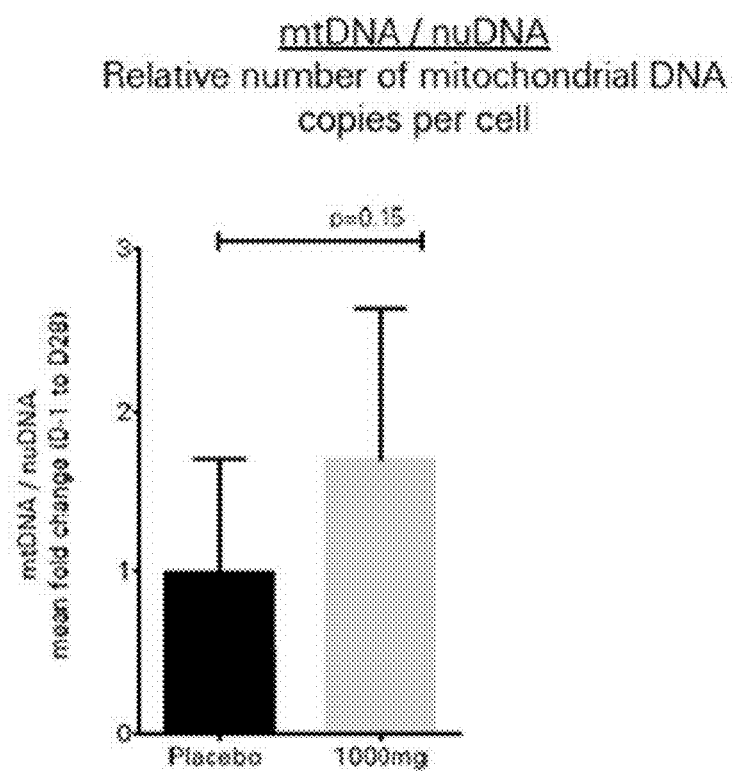
FIG. 10 shows the mean fold change between day −1 (pre-dose) and day 28 in relative numbers of mitochondrial DNA per cell, for a cohort of subjects administered 1000 mg/day urolithin A compared with a cohort of subjects administered placebo.

Increasing mitochondrial content per cell in muscle tissue was also observed following dosage of 1000 mg urolithin A per day for 28 days compared with placebo. FIG. 10 shows the mean fold change between day −1 and day 28 in relative numbers of mitochondrial DNA copies per cell.

e) Acylcarnitine Plasma Levels

Metabolomics is the study of known measurable metabolites in a sample. Metabolomics allows visualisation of in vivo effects at the whole organism level on relevant cellular pathways to demonstrate the effects of interventional trials. The technique made use of HPLC-MS-MS analysis of plasma samples of subjects administered either placebo or urolithin A to characterise metabolites. 781 plasma metabolites which cover all of the biochemical processes of the body were investigated.

Figure 11:
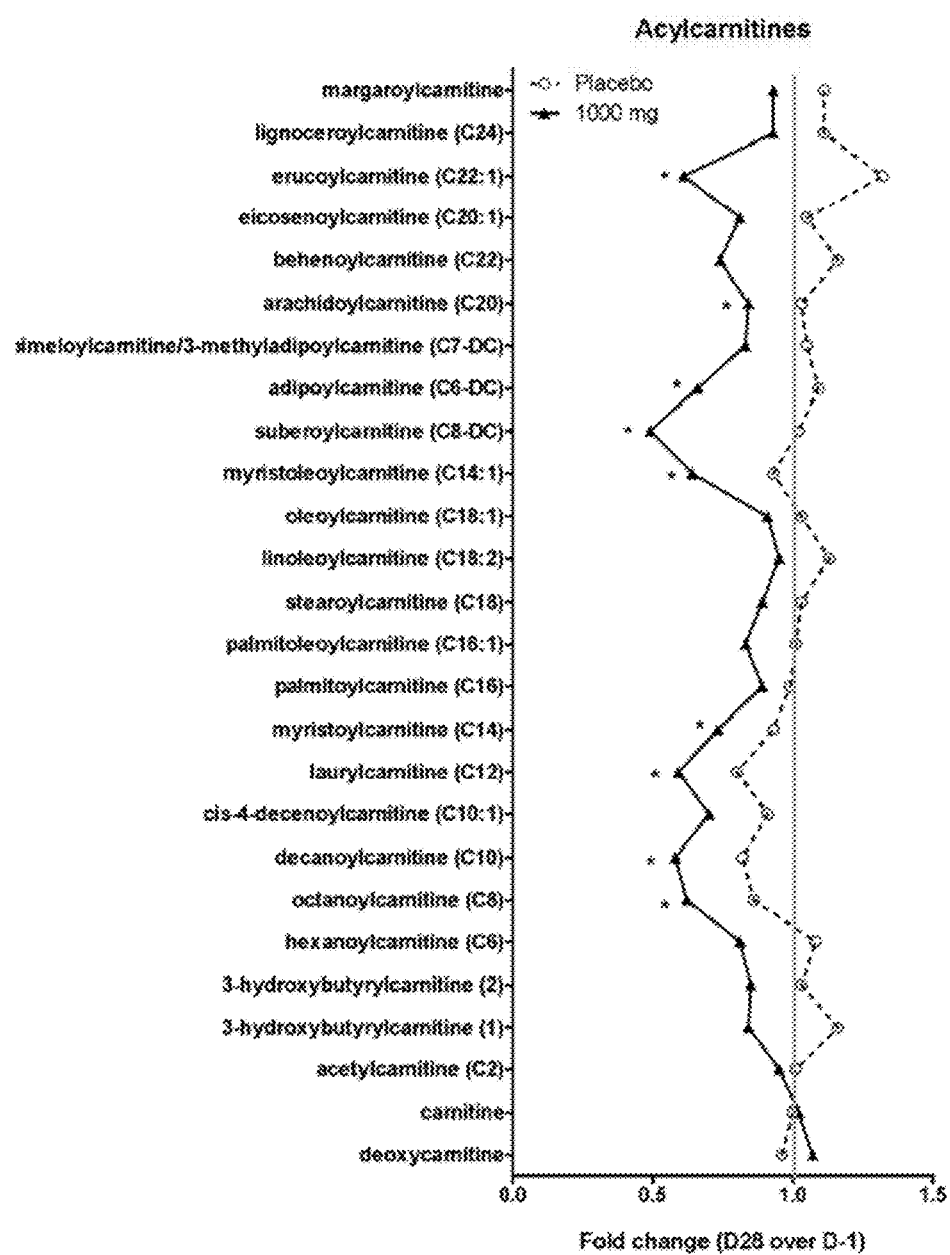
FIG. 11 shows the fold change in levels of various acylcarnitines between day −1 and day 28 for cohorts of subjects administered placebo or 1000 mg/day urolithin A.

FIG. 11 shows the fold change in levels of various acylcarnitines between day −1 (pre-dose) and day 28 for the placebo and 1000 mg urolithin A cohorts. The grey line in FIG. 11 corresponds to a fold change of 1, i.e. absence of effect. $*P<0.05$ correspond to a significant effect from D-1 (pre-dose) to D28, calculated after a repeated measures ANOVA. N=9 per group. Values represent the arithmetic mean of the fold changes. These results show that there is an overall decrease in plasma short chain (e.g. (hexanoylcarnitine C6) up to long chain (e.g. ximenoylcarnitine C26:1) acylcarnitines after 28 days treatment with urolithin A at 1000 mg.

Acylcarnitines can be considered as plasma markers for mitochondrial dysfunction and fatty acid disorder. Decrease in acylcarnitines is indicative of induction of fatty acid oxidation, which is a measure of mitochondrial function. Importantly, carnitine levels did not change, meaning that there was no impairment of the entry of carnitine inside the cells (Longo et al, Am J Med Genet C Semin Med Genet, 2006, 142C(2), p 77-85). Elevated levels of acylcarnitines are used as a diagnostics for fatty acid oxidation deficiencies (Van Hove et al, Am J Hum Genet. 1993, 52(5), p 958-966) and have been associated with mitochondrial dysfunction (Haas et al, Mol Genet Metab, 2008, 94(1), p 18-37; Frye et al, Translational Psychiatry, 2013, 3, e220). Higher acylcarnitine factor scores have also been associated with lower levels of objectively measured physical performance in a group of older men (Lum et al, J Gerontol A Biol Sci Med Sci, 2011, 66(5), p 548-53). On the other hand, a 10-week exercise intervention in a cohort of obese subjects reduced plasma long-chain acylcarnitine (Rodriguez-Gutierrez et al, J Int Soc Sports Nut, 2012, 9(1), 22).

f) Pyruvate, Lactate, Glucose Plasma Levels

Figure 12:
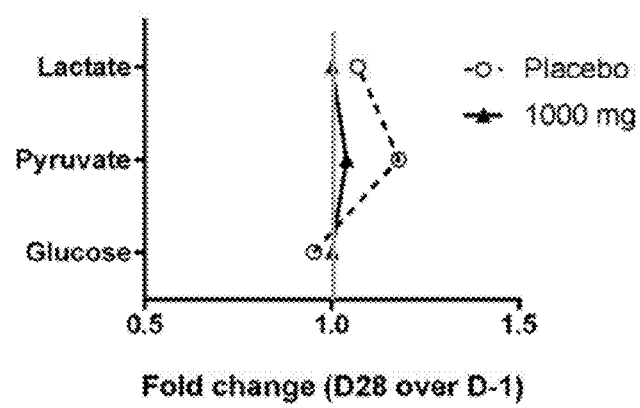
FIG. 12 shows the fold change in levels of lactate, pyruvate and glucose between day −1 (pre-dose) and day 28 for cohorts of subjects administered placebo or 1000 mg/day urolithin A.
Figure 13:
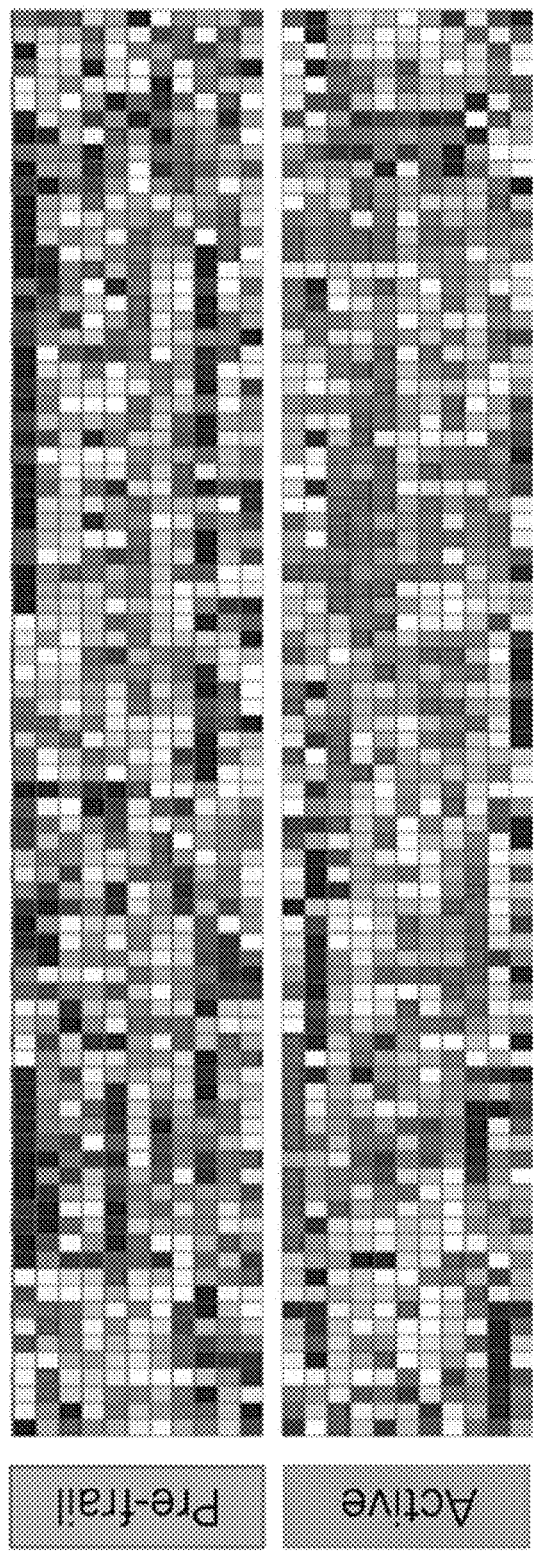
FIG. 13 shows heatmap representations of the change in expression level of genes in the geneset GO_MITOCHONDRION for groups of pre-frail elderly and active elderly subjects.

FIG. 12 shows the fold change in levels of pyruvate, lactate and glucose in plasma between day −1 and day 28 for the placebo and 1000 mg urolithin A cohorts. The data represent the fold change from D-1 to D28. The grey line corresponds to a fold change of 1, i.e. absence of effect. N=9 per group. Values represent the arithmetic mean of the fold changes.

Pyruvate and lactate are the end-products of glycolysis and are increased in case of mitochondrial dysfunction (REF). Overall there is no significant change in any of these parameters, meaning that the decrease in acylcarnitines is not due to mitochondrial dysfunction, but rather to an improvement in fatty acid oxidation efficiency.

Altogether, these data show that 28 days of treatment with Urolithin A at 1000 mg is able to improve mitochondrial function and fatty acid oxidation.

g) Comparison of Characteristics of a Group of Active Elderly Subjects and a Group of Pre-Frail Elderly Subjects Identification of a Group of Prefrail and Active Elderly Subjects In this study, characteristics of pre-frail elderly were compared to active elderly. Pre-frailty was defined as fulfilling at least two out three criteria for sarcopenia: low muscle mass (i.e. skeletal muscle mass index (SMI) assessed by Bio-impedance Analysis (BIA)), low muscle strength (handgrip strength, assessed by the Jamar dynamometer) and/or low physical performance (gait speed, assessed by the 4-meter walk test). A sedentary lifestyle was defined as having an activity category of 1 as assessed by the International Physical Activity Questionnaires (IPAQ), which means an activity level of <600 MET (metabolic equivalent unit)—minutes per week). Active elderly were defined as having a normal muscle mass, normal muscle strength, normal physical performance and an activity level of category 2 or 3 as assessed by the IPAQ (activity level ≥600 MET—minutes per week).

Demographics

In total, 11 pre-frail (6 males and 5 females) and 11 active (6 males and 5 females) subjects between the ages of 61 to 80 years old participated in this study. Data from 10 pre-frail (5 males and 5 females) and 11 active (6 males and 5 females) subjects were included for analysis, because one pre-frail male subject was excluded from the study due to a lack of compliance to study restrictions. In the end, pre-frail and active subjects were matched on age (70.2±5.8 vs 70.0±6.7 yrs) and BMI (25.7±4.2 vs 24.6±3.9 kg/m$^2$). Subjects were all Caucasian, except for one active subject, who was Afro-Dutch.

Physical Performance

Group means of the different physical performance outcomes are listed in the Table below. The pre-frail subjects were different from the active subjects in terms of physical performance. In terms of physical activity, the pre-frail subjects were all sedentary, defined by a daily energy expenditure of less than 600 MET minutes per week. A daily energy expenditure of 600 MET minutes per week corresponds to a maximum of 25 minutes of walking per day. The mean daily energy expenditure in the active group was 7926.5 MET minutes per week, which corresponds to 1 hour of vigorous exercise plus 2 hours of cycling per day. Eligibility for the pre-frail group included a low SMI, grip strength and walk speed, all of which were lower than the active group. Subjects were matched on BMI, so this was comparable between groups. The subjects in the pre-frail group were selected on a grip strength of below the threshold that is used to define frailty, whereas the pre-frail group produced a mean value of 39.3 kg (males and females combined). During the study days, the quadriceps strength was assessed and as expected the pre-frail group produced a lower mean quadriceps strength than the active group (139.5 Newton vs 221.3 Newton, respectively). When comparing the two groups for postural stability and the SPPB score, the mean scores were comparable. However, the pre-frail group was slower in walking 4 meters, than the active group (4.50 seconds vs. 2.90 seconds, respectively)

Table showing physical performance characteristics of the groups of subjects:

| Demographics | Pre-frail, sedentary (n = 10) | Healthy, active (n = 11) |
|---|---|---|
| Body Mass Index mean (SD), range, in kg/m$^2$ | 25.7 (4.2), 17.8-33.2 | 24.6 (3.9), 20.1-32.0 |
| Skeletal Muscle Index, mean (SD), range, in kg/m$^2$ | 10.90 (2.70), 4.94-13.61 | 12.10 (2.50), 8.82-16.00 |
| Physical activity, mean (SD), range, in MET minutes per week | 396.0 (109.2), 262.0-579.0 | 7926.5 (5258.5), 2555-19344 |
| 4 m walk time, mean (SD), range, in seconds | 4.50 (2.20), 3.28-10.69 | 2.90 (0.30), 2.40-3.19 |
| Short Physical Performance Battery, mean (SD), range, in total score | 9.7 (1.70), 7-12 | 10.5 (1.81), 8-12 |
| Postural stability, mean (SD), range, in mm sway | 397.26 (386.85), 202.5-488.0 | 449.03 (413.37), 196.3-970.1 |
| Grip strength, mean (SD), range, in kg | 17.7 (5.7), 12.4-31.2 | 39.3 (10.3), 23.9-52.3 |
| Quadriceps strength, mean (SD), range, in kg | 139.5 (55.97), 61-220 | 221.3 (51.93), 133-302 |

As can be seen, the pre-frail group performed worse in measurements of physical performance characteristics indicative of muscle strength/muscle performance.

Muscle Biopsy

Muscle biopsies were collected from the vastus lateralis muscle of the right leg of subjects using the Bergström biopsy needle technique in order to perform ex vivo measurements. The minimal amount of each muscle tissue sample was 150 mg. Muscle tissue was collected and processed for RNA and DNA analysis.

Muscle tissue were snap frozen using liquid nitrogen immediately after collection and further, long term storage was in a −80° C. freezer. Microarray was used to identify the gene sets influenced by the physical activity and muscle strength of the participants. Microarray data was analysed running a Gene Set Enrichment type of Analysis (GSEA), which tells which biological processes are up or down-regulated at the scale entire gene-sets, rather than gene by gene.

Gene expression data from muscle biopsies of the 22 subjects were obtained using the HTA 2.0 microarray chip from Affymetrix was used to measure mRNA expression levels of 42 935 reporters/probes associated to 33 804 annotated transcripts or genes (mRNA).

The mRNA expression profiles were generated for thousands of genes from the samples belonging to either Active or Pre-frail study participants.

The GSEA original algorithm implementation from the BROAD Institute was used to perform all the gene sets enrichment analysis.

The gene sets tested were extracted from the MSIGDB version 5.1 that contains pre-defined genes sets organized by collection categories and sub-categories. The ranked list of genes used in the analysis was obtained using the moderated T statistics from the limma linear model of the Active vs. Pre-frail A positive Enrichment Score indicates gene set enrichment at the top of the ranked list. A normalized enrichment score (NES) is calculated by accounting for differences in gene set size and for correlations between gene sets and the expression data set. This score is then used to compare analysis results across gene sets and it is the basis of the significance calculation for a given set to be enriched.

A multiple testing correction is also applied by GSEA to control the Type 1 error rate Classification of the genesets (mitochondria associated or not), demonstrates the overall biological trend of the results obtained by GSEA: a down regulation of mitochondria and its related sub-processes in pre-frail subjects. A further closer inspection of the inter-connection between sets informs about common and specific sub-processes.

The tables below focus on the 10 most negatively enriched gene sets, i.e with the lowest NES. These represent the gene sets which were most down-regulated in the pre-frail elderly group relative to the active elderly group. These 10 most down regulated gene sets are all related to the mitochondria or energy releasing molecular processes.

| Name | Es | Nes | Size | NomPVal | FwerPVal |
|---|---|---|---|---|---|
| HALLMARK_OXIDATIVE_PHOSPHORYLATION | −0.80 | −4.09 | 198.00 | <=0.001 | <=0.001 |
| WONG_MITOCHONDRIA_GENE_MODULE | −0.69 | −3.63 | 214.00 | <=0.001 | <=0.001 |
| MOOTHA_VOXPHOS | −0.79 | −3.57 | 85.00 | <=0.001 | <=0.001 |
| MITOCHONDRION | −0.65 | −3.57 | 330.00 | <=0.001 | <=0.001 |
| MOOTHA_HUMAN_MITODB_6_2002 | −0.63 | −3.49 | 421.00 | <=0.001 | <=0.001 |
| MOOTHA_MITOCHONDRIA | −0.62 | −3.49 | 438.00 | <=0.001 | <=0.001 |
| MITOCHONDRIAL_PART | −0.69 | −3.39 | 137.00 | <=0.001 | <=0.001 |
| KEGG_PARKINSONS_DISEASE | −0.70 | −3.34 | 111.00 | <=0.001 | <=0.001 |
| MITOCHONDRIAL_MEMBRANE_PART | −0.81 | −3.30 | 50.00 | <=0.001 | <=0.001 |
| MITOCHONDRIAL_INNER_MEMBRANE | −0.75 | −3.30 | 64.00 | <=0.001 | <=0.001 |

Top 10 Down Regulated Gene Sets (FDR<=0.1)

| Name | Description |
|---|---|
| HALLMARK OXIDATIVE PHOSPHORYLATION | Genes encoding proteins involved in oxidative phosphorylation. |
| WONG MITOCHONDIRA GENE MODULE | In human breast cancer, activation of a poor-prognosis "wound signature" is strong associated with induction of both a mitochondria gene module and a proteasome gene module. |
| MOOTHA VOXPHOS | Sets of genes involved in oxidative phosphorylation whose expression is coordinately decreased in human diabetic muscle. |
| MITOCHONDRION | Genes annotated by the GO term GO: 0005739 (cellular component mitochondria). |
| MOOTHA HUMAN MITODB 6 2002 | Sets of genes involved in oxidative phosphorylation whose expression is coordinately decreased in human diabetic muscle. |
| MOOTHA-MITOCHONDRIA | Sets of genes involved in oxidative phosphorylation whose expression is coordinately decreased in human diabetic muscle. |
| MITOCHONDRIAL_PART | Genes annotated by the GO term GO: 0044429 (mitochondrial subcomponent, mitochondrion component). |
| KEGG PARKINSONS DISEASE | Parkinson's disease, Mutations in parkin, DJ1, and PINK1 may after mitochondrial activity, potentially impairing proteasome function. |
| MITOCHONDRIAL MEMBRANE PART | Any constituent part of the mitochondrial membrane, either of the lipid bilayers that surround the mitochondrion and form the mitochondrial envelope. |
| MITOCHONDRIAL INNER MEMBRANE | The inner, i.e. lumen-facing, lipid bilayer of the mitochondrial envelope. |

Top 10 Down Regulated Gene Sets (FDR<=0.1)

Heatmap representations of the change in expression level of genes in the GO_MITOCHONDRION geneset (the fourth geneset in the table above) for the pre-frail elderly and active elderly subjects is shown in FIG. 11. Heatmnaps represent the same mitochondrial genes (in rows) across the different studies and groups of subjects (in columns). The enrichment in GO_MITOCHONDRION genes expression is significant in the active elderly group vs the pre-frail elderly group. In other words, the active elderly group has strong expression levels of mitochondria-related genesets compared with the pre-frail group.

Referring to d) above, the table of FIG. 8, and FIG. 9, it can also be seen that administration of urolithin A leads to increases in expression levels of mitochondrial genesets which are downregulated in pre-frail elderly subjects relative to active elderly subjects.

Summary

In summary, urolithin A shows results in impacting mitochondrial genes expression, metabolomics profile and muscle function biomarkers. Metabolomics showed that many metabolites were impacted by treatment. A significant impact on the acylcarnitine pathway (mitochondrial function) was observed on administration of 1000 mg/day urolithin A. Strong trends were observed with regard to upregulation of gene expression of genes associated with autophagy, mitochondrial function and fatty acid oxidation, with LAMP2 and FABP3 being significantly upregulated at 1000 mg. Trends to increased mitochondrial DNA were observed at 1000 mg. Finally, it was shown that mitochondrial genesets upregulated upon administration of urolithin A are also downregulated in pre-frail elderly compared to active elderly subjects.

Example 5: Bioavailability Following Single Oral Administration of Urolithin A at 1000 mg Dose (on Day 28)

A double-blind, randomized, placebo controlled clinical trial was conducted in healthy elderly to establish the steady state levels of Urolithin A in plasma. Elderly subjects (61-82 years) (n=9), participated in each group of dosing. The subjects met all the inclusion and exclusion criteria of the study and signed informed consent. The subjects were overnight fasted and the plasma was collected in the morning before breakfast to assess steady state levels. Subjects were given a dose of Urolithin or placebo each morning for the 28 day trial. The urolithin A was given as softgel capsules containing 250 mg of Urolithin A in each capsule.

Plasma samples were collected for assessment of Urolithin A steady state concentrations in the 4-week Urolithin A study at the following time points (Day 0, Day 7, Day 14, Day 28, Day 29, Day 31, and Day 32). were measured On day 28 the subjects were admitted to a Phase 1 clinical trial unit and the kinetics of Urolithin A absorption, and elimination following multiple 4-week dosing were followed until 96 hours following the last dosing on Day 28. Plasma was collected at the following time-points post last dosing with Urolithin A on Day 28: pre-dose, 1 hr, 2 hr, 4 hr, 6 hr, 8 hr, 12 hr, 24 hr, 72 hr and 96 hr. At each time point a 6 mL blood sample should was drawn into K2-EDTA coated tube. The blood samples were gently inverted a few times for complete mixing with the anticoagulant. The exact time of sample collection was recorded on the eCRF (electronic case report from). Within 30 minutes following blood collection, each blood sample was centrifuged at 1500 g for 10 minutes at 4° C. Within 30 minutes after the centrifugation, the top layer of human plasma was transferred into pre-labelled polypropylene tube. Tubes were capped immediately from each time point and the plasma frozen in an upright position at approximately −80° C. for storage. The samples were shipped on dry ice for bioavailability analysis.

Plasma concentrations of Urolithin A and its metabolites, Urolithin A glucuronide and Urolithin A sulfate, were analyzed in plasma to evaluate total levels of Urolithin A. The concentrations of Urolithin A and its metabolites in plasma were determined using validated LC MS/MS assays.

Figure 14:
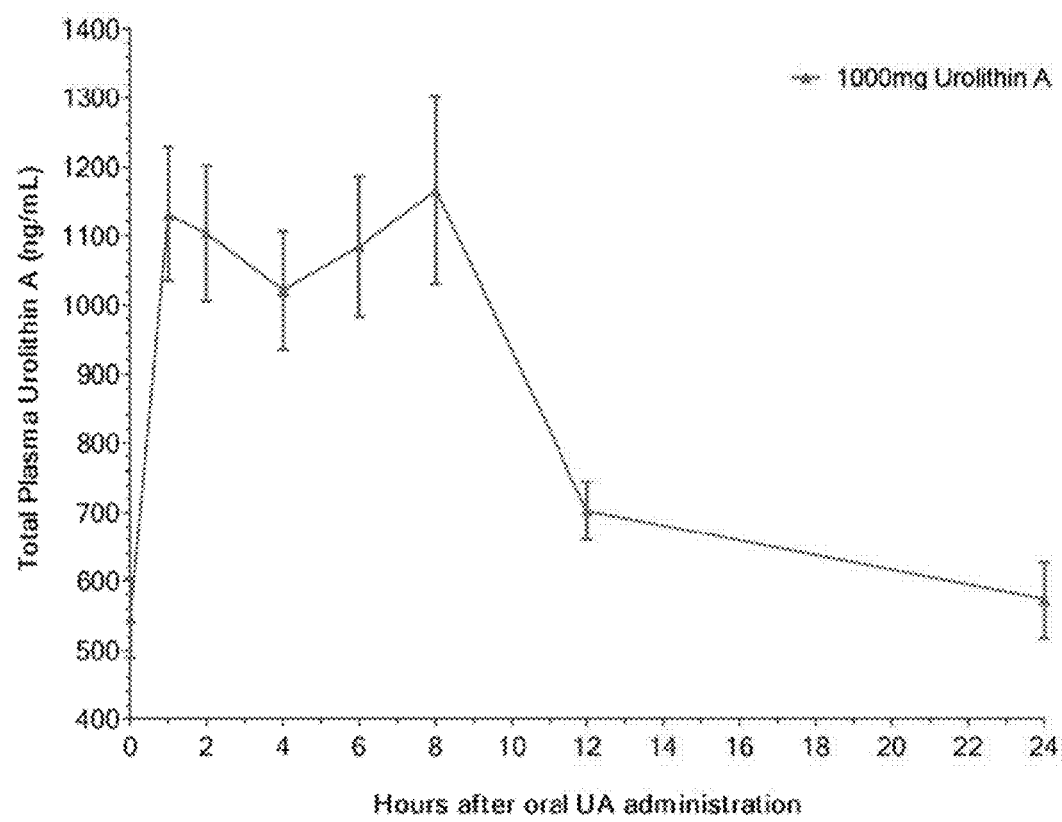
FIG. 14 shows the pharmacokinetic bioavailability profile of total Urolithin A (combination of Parent and Glucuronide and Sulfate metabolites) in plasma following single oral administration of Urolithin A at 1000 mg (at Day 28).

Total Plasma Urolithin A (parent+glucuronide and sulfate metabolites) is shown in the pharmacokinetic graphs in FIG. 14.

Figure 15:
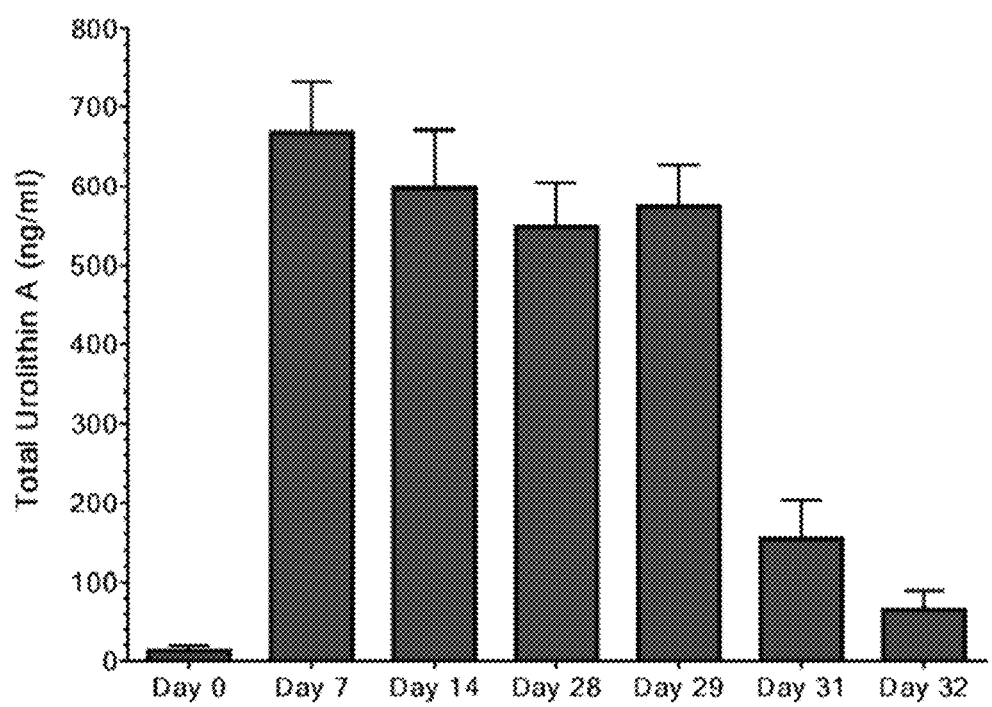
FIG. 15 shows total Urolithin A (combination of Parent and +Glucuronide and Sulfate metabolites) levels in plasma over the 4 week study with 1000 mg urolithin A oral administration.
Figure 16:
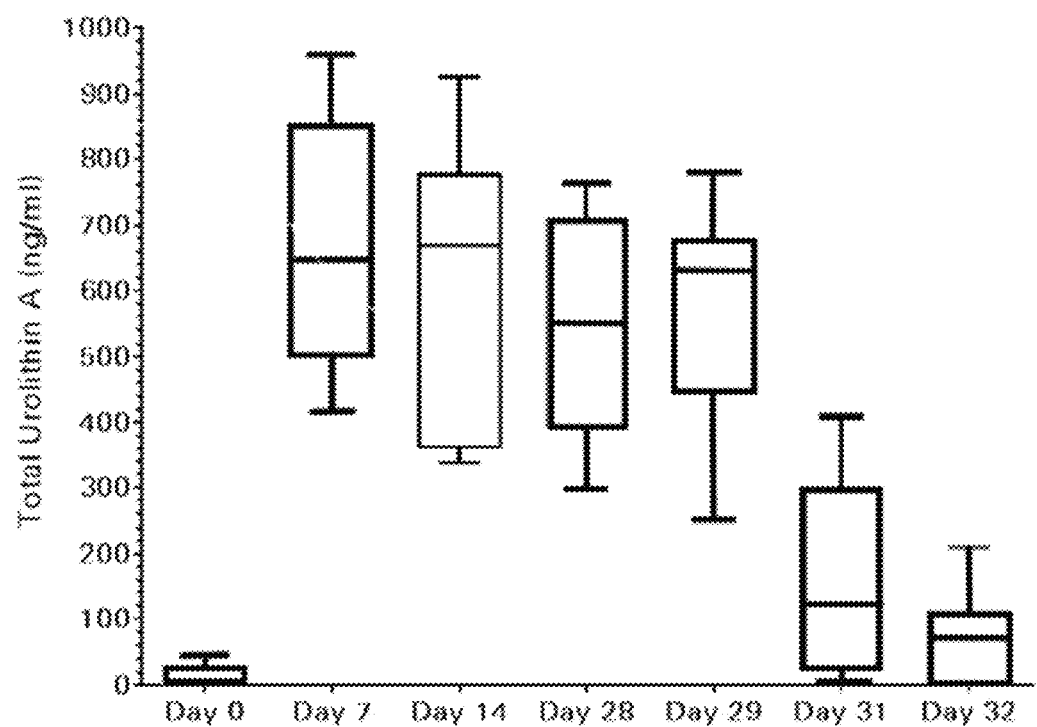
FIG. 16 shows total Urolithin A levels (parent and glucuronide and sulfate metabolites) in plasma are shown in a Box and Whiskers plot that shows the minimum level (edge of lower error bar), first quartile (lower edge of the box plot), median (solid line in the bar graph), 3rd quartile (upper edge of the box plot) and maximum plasma levels of Urolithin A (edge of upper error bar).

Example 6 Measurement of Steady State Levels after 1000 mg Multiple Dosing for 28 Days 9 healthy study participants were orally administered 500 mg of Urolithin A (UA) per day in the morning in softgels (250 mg capsules) or 28 days (4 weeks) in a randomized, placebo controlled, double-blind Phase 1 study. Study participants had negligible UA levels at the start of the study intervention. Steady state levels were measured 24 hours after a dose but before the subsequent dose (UA +Steady state UA levels were reached following 7 days of repeat dosing and were maintained through the study intervention period. Following the end of the 4-week UA administration, the steady state levels gradually declined (Day 31 and Day 32) (see FIGS. 15 and 16).

Example 7: Clinical Trial Investigating Effect on Muscle Function

A randomized, double-blind, placebo controlled study comprising 90 subjects (30 per group) is carried to investigate the efficacy of Urollithin A on muscle function in otherwise healthy middle aged, overweight, and inactive individuals between 40 to 65 years of age. The individuals are to be sedentary males and females in the age range of 40 to 65 years, who are above normal body weight (BMI between 25.0 and 34.9 kg/m²).

The study comprises 3 groups:

Group A—Low dose/Product A containing 500 mg Urolithin A

Group B—High dose/Product B containing 1000 mg Urolithin

Group C—Placebo

Inclusion criteria are as follows:

1. Healthy males and females 40 to 65 years of age, inclusive
2. Subjects who have not participated within the last 1 year in clinical trials focused on improving muscle function and physical performance
3. Female participant is not of child bearing potential, defined as females who have had a hysterectomy or oophorectomy, bilateral tubal ligation or are post-menopausal (natural or surgically with >1 year since last menstruation)

or,

Females of childbearing potential must agree to use a medically approved method of birth control and have a negative urine pregnancy test result. All hormonal birth control must have been in use for a minimum of three months. Acceptable methods of birth control include:

Hormonal contraceptives including oral contraceptives, hormone birth control patch (Ortho Evra), vaginal contraceptive ring (NuvaRing), injectable contraceptives (Depo-Provera, Lunelle), or hormone implant (Norplant System)

Double-barrier method

Intrauterine devices

Non-heterosexual lifestyle or agrees to use contraception if planning on changing to heterosexual partner(s)

Vasectomy of partner (shown successful as per appropriate follow-up)

4. Body mass index (BMI) between 25.0 and 34.9 kg/m², inclusive
5. Sedentary behaviour defined as having an activity category of 1 as assessed by the International Physical Activity Questionnaire (IPAQ; Appendix IV) where activity level is <600 MET (metabolic equivalent unit—minutes per week and limited to low-intensity activities, less than 30 min of moderate activity 5 days per week, or less than 20 min vigorous activity 3 days per week)
6. Agree to avoid exercising 24 hours prior to study visits and maintain low physical activity status for the duration of the trial
7. Agree to refrain from consumption of pomegranate juice and walnuts from 2 weeks prior to baseline and through the study period
8. Agree to limit consumption of raspberries, strawberries and cloudberries from 2 weeks prior to baseline and through the study period
9. Agree to refrain from using NSAIDs for 7-days prior to and following muscle sample collection
10. Good general health to perform exercise testing safely, as determined by the Qualified Investigator based on medical history, physical examination, ECG and laboratory results
11. Low $VO2_{max}$ defined as per Table 1 via the cycle ergometer prior to baseline.

TABLE 1

VO₂ Max criteria for Inclusion

| Age | Male VO₂ Max (ml/kg/min) | Female VO₂ Max (ml/kg/min) |
|---|---|---|
| 40-49 | <35.0 | <31.0 |
| 50-59 | <33.0 | <29.0 |
| 60-65 | <31.0 | <26.0 |

12. Comprehension of the nature and purpose of the study including possible risks and side effects, and ability to communicate in person and by telephone in a manner that allows all protocol procedures to be carried out safety and reliably in the opinion of the investigative site staff
13. Has given voluntary, written, informed consent to participate in the study.

Exclusion Criteria are as follows:
1. Women who are pregnant, breast feeding, or planning to become pregnant during the trial
2. Smokers or ex-smokers within the past 1 year from screening, including use of vaporizers or e-cigarettes
3. Participation in another clinical study or receipt of an investigational drug within 60 days of the screening visit
4. Blood donation within 1 month of baseline, as well as planned donation 1 month after end of study.
5. Recent history (within the last 2 years) of alcohol or other substance abuse
6. Use of medicinal marijuana.
7. Unable to swallow capsules
8. Regular participation in a structured exercise program with physical activity levels in Category 2 or higher defined as 20 min vigorous activity 3-times per week, moderate activity for 30 min 5 days per week or more
9. Inability to abstain from intensive muscular effort
10. Individuals who have engaged in 1 hour or more per week of resistance training in the past 3 months.
11. Currently experiencing any medical condition that interferes with the ability to undergo physical strength testing during the study
12. Recent participation in a weight loss diet, or loss >5% of total body weight within 3 months of randomization
13. Clinically significant abnormal laboratory results at screening
14. Allergy or sensitivity to test product ingredients (or closely related compounds)
15. Allergy to anesthetic (Xylocaine, lidocaine)
16. Soy allergy
17. Inability to abstain from the consumption of pomegranate juice or walnuts
18. Inability to abstain from frequent consumption of raspberries, strawberries or cloudberries
19. Excessive consumption of beverages containing xanthine bases (>4 cups per day) such as coffee, tea, and cola
20. Use of NHPs for the purposes of muscle building or function. Use of other NHPs must have been on a stable dosing regimen for at least a month prior to baseline and must maintain their current dosing regimen throughout the trial and must not begin taking any new NHPs throughout the trial; if the subject wishes to stop taking the NHP prior to beginning the trial they must do so at least 2 weeks prior to randomization.
21. History of or current diagnosis of bleeding/blood disorder
22. Use of oral anticoagulants (blood thinners), New Oral Anticoagulants (NOAC) or antiplatelet agents.
23. Use of NSAID medications within one week before or after the needle muscle biopsy procedures.
24. Use of steroid medications, current/recent (3 months) history of anabolic steroid, corticosteroid or estrogen use.
25. Use of statins
26. Use of thyroid medications.
27. Asthma that has not been controlled with a stable regimen for a minimum of a year, or Asthma requiring the use of certain medications.
28. Diagnosis of COPD
29. Chronic myalgia, fibromyalgia or conditions characterized by regular muscle pain
30. Metal fixation plates or screws from a previous surgery
31. Clinically significant underlying systemic illness that may preclude the participant's ability to complete the trial or that may confound the study outcomes (i.e. terminal illnesses)
32. Diagnosis of active cardiac or peripheral vascular disease
33. SBP/DBP≥150/95 mmHg without the use of hypertension medications, or SBP/DBP>140/90 mmHg with the use of hypertension medications.
34. Diagnosed hyperlipidemia
35. Renal or hepatic impairment or disease
36. Any major diseases of the gastrointestinal, pulmonary or endocrine systems
37. Type I and Type II diabetes
38. Autoimmune disease or immuno-compromised (i.e. HIV positive, use of anti-rejection medication, rheumatoid arthritis, Hepatitis B/C positive)
39. Diagnosis of chronic infectious disease
40. Diagnosis of phenylketonuria
41. Cancer, except skin cancers completely excised with no chemotherapy or radiation with a follow up that is negative. Participants with cancer in full remission for more than five years after diagnosis are acceptable if approved by QI.
42. Significant neurological or psychiatric illness, including, but not limited to, Parkinson's disease and bipolar disorder as assessed by QI.
43. History of seizures
44. Individuals who are cognitively impaired and/or who are unable to give informed consent
45. Any other condition which in the qualified investigators opinion may adversely affect the participant's ability to complete the study or its measures or which may pose significant risk to the participant Any other condition which in the qualified investigators opinion may adversely affect the participant's ability to complete the study or its measures or which may pose significant risk to the participant Study Design This is to be a randomized, double-blind, placebo controlled study on improving muscle function in middle aged, inactive, and overweight individuals (between 40 to 65 years of age). At screening (visit 1), fasting peripheral blood will be collected to determine CBC, electrolytes (Na, K, Cl), fasting blood glucose, creatinine, eGFR, AST, ALT, and bilirubin. Blood samples will also be collected to determine Hepatitis B, Hepatitis C and HIV status. Urine will also be collected for a urinalysis. Medical history and concomitant therapies will be reviewed; height, weight, heart rate and blood pressure will be measured and an ECG will be performed. Subjects will complete the International Physical Activity Questionnaire (IPAQ).

At baseline (visit 2—day 0), eligible subjects will return to the clinic. Weight, heart rate and blood pressure will be measured; concomitant therapies will be reviewed. A physical exam will be performed. Subjects will be randomized into a treatment group.

Subjects will undergo a 6-minute walk test to measure distance walked and gait speed. Chair Stand will also be measured. Hand grip muscle strength will be measured by Jamar dynamometer. Subject's quality of life will be measured by SF-36. An exercise tolerance test using a cycle ergometer will be performed. REE will be measured and the Borg Rating of Perceived Exertion Scale will be performed. Muscle extension isokinetic leg strength (both legs, flexion, and extension) will be measured at one speed with the Biodex. A DXA will be performed. Blood samples will be collected for Lipid Profile (total cholesterol, triglycerides, LDL, HDL), HbA1c and fasting insulin. Plasma will be collected for metabolomics analysis of plasma acylcarnitine metabolites. Muscle biopsy samples will be collected to measure in vive mitochondrial gene expression via microarray. 3-day food records using DietMaster Pro will be reviewed. Fecal sample will also be collected to establish baseline microbiome profile of study subjects. Investigational product and treatment diary will be dispensed and subjects will be instructed on use. The subject treatment diary will be used to record daily product use, changes in concomitant therapies, and any adverse events and symptoms throughout the study.

Subjects will return to the clinic at visit 3 (Month 2, Day 60). Weight, heart rate, and blood pressure will be measured; concomitant therapies and adverse events will be reviewed. An exercise tolerance test using a cycle ergometry will be performed. REE will be measured and the Borg Rating of Perceived Exertion Scale will be administered. 3-day food records will be reviewed. Subject's quality of life will be measured by SF-36. Plasma will be collected for metabolomics analysis of plasma acylcarnitine metabolites. Investigational product and treatment diary will be returned, re-dispensed and compliance will be calculated.

Subjects will return to the clinic at visit 4 (Month 4, Day 120-end of study). Weight, heart rate, and blood pressure will be measured; concomitant therapies and adverse events will be reviewed. Investigational product and treatment diary will be returned and compliance will be calculated. Subjects will undergo a 6-minute walk test to measure distance walked. Gait Speed and Chair Stand will also be measured. Hand grip muscle strength will be measured by Jamar dynamometer. Subject's quality of life will be measured by SF-36. 3-day food records will be reviewed. An exercise tolerance test using a cycle ergometry will be performed. REE will be measured and the Borg Rating of Perceived Exertion Scale will be administered. Muscle extension isokinetic leg strength (both legs, flexion and extension) will be measured at one speed with the Biodex. A DXA will be performed. Blood samples will be collected for Lipid Profile (total cholesterol, triglycerides, LDL, HDL), HbA1c and fasting insulin. Plasma will be collected for metabolomics analysis of plasma acylcarnitine metabolites. Fecal sample will also be collected to study changes in microbiome following the intervention. Muscle biopsy samples will be collected to measure in vive mitochondrial gene expression. Blood samples will also be collected to determine CBC, electrolytes (Na, K, Cl), creatinine, AST, ALT, and bilirubin.

Primary Endpoint:

The change in exercise tolerance as assessed by power output on the cycle ergometer from baseline to day 120 between Urolithin A 500 mg/d and 1000 mg/d and placebo.

Secondary Endpoints:
1. The change in exercise tolerance as assessed by power output on the cycle ergometer from baseline to day 60 between Urolithin A 500 mg/d and 1000 mg/d and placebo.
2. The change in exercise tolerance as assessed by time-to-fatigue (and cycling distance) on the cycle ergometer from baseline to day 60 and from baseline to day 120 between Urolithin A 500 mg/d and 1000 mg/d and placebo.
3. The change in handgrip strength of the non-dominant hand as assessed by Jamar dynamometry from baseline to day 120 between Urolithin A 500 mg/d and 1,000 mg/d and placebo
4. The change in isokinetic lower body muscle strength as assessed by the isokinetic cycle ergometer and a Biodex isokinetic dynamometer from baseline to day 120 between Urolithin A 500 mg/d and 1,000 mg/d and placebo
5. The change in physical performance on the cycle ergometry defined as the time to reach 85% of maximum heart rate (based on Karvonen Formula) and peakVO2 from baseline to days 60 and from baseline to day 120 between Urolithin A 500 mg/d and 1,000 mg/d and placebo
6. The change in distance walked in the 6-minute walk test as a measure of aerobic endurance from baseline to day 120 between Urolithin A 500 mg/d and 1,000 mg/d and placebo
7. The change in gait speed from baseline to day 120 between Urolithin A 500 mg/d and 1,000 mg/d and placebo as derived from the 6-minute walk test
8. The change in the 30-second chair stand test from baseline to day 120 between Urolithin A 500 mg/d and 1,000 mg/d and placebo (Appendix I)
9. The change from baseline to days 60 and from baseline to day 120 between Urolithin A 500 mg/d and 1,000 mg/d and placebo in participant's quality of life as assessed by the SF-36 questionnaire (Appendix II)
10. The change from baseline to days 60 and from baseline to day 120 between Urolithin A 500 mg/d and 1,000 mg/d and placebo in participant' perceived exertion relative to their physical fitness as assessed by the Borg Rating of Perceived Exertion Scale (Appendix III)
11. The change from baseline to days 60 and 120 between Urolithin A 500 mg/d and 1,000 mg/d and placebo in participant' resting energy expenditure (REE) as assessed by Cardiocoach CO2 system.
12. 3-day food records to track calorie consumption (from protein, carbohydrates, fat, and micronutrient intake) reviewed at baseline and days 60 and 120.
13. The change from baseline to day 60 and from baseline to day 120 in serum lipid profile, insulin, and HbA1C between Urolithin A 500 mg/d and 1,000 mg/d and placebo
14. Change in lean body mass as assessed by dual X-ray absorptiometry (DXA) from baseline to day 120 between Urolithin A 500 mg/d and 1,000 mg/d and placebo
15. Change in acylcarnitine profile in plasma via Metabolomics assessments from baseline to day 60, and from baseline to day 120
16. Change in plasma muscle function biomarkers (myostatin, follistatin, inflammatory cytokines and mitokines) from baseline to day 60 and from baseline to day 120

17. The change in in vivo mitochondrial gene expression from baseline to day 120 between Urolithin A 500 mg/d and 1,000 mg/d and placebo as assessed via microarray performed on muscle biopsy
18. Fecal Sample to assess the impact of Urolithin A on the microbiome at baseline and at day 120.

Schedule of Assessments: (N=90)

| | Visit 1 Screening | Visit 2 Baseline Day 0 | Visit 3 Month 2 Day 60 | Visit 4 Month 4 Day 120 |
|---|---|---|---|---|
| Informed consent | X | | | |
| Review inclusion/exclusion criteria | X | X | | |
| Review medical history | X | | | |
| Review concomitant therapies | X | X | X | X |
| Height*, weight, heart rate, blood pressure | X | X | X | X |
| *Height will only be measured at visit 1 | | | | |
| Urine pregnancy test | X | X | | |
| ECG Test | X | | | |
| Randomization | | X | | |
| Physical examination | | X | | |
| Laboratory test: CBC, electrolytes (Na, K, Cl), fasting blood glucose*, creatinine, AST, ALT, eGFR*, bilirubin | X | | | X |
| *Will only be measured at visit 1 | | | | |
| Urinalysis | X | | | |
| Hepatitis B, C and HIV | X | | | |
| 6-Minute Walk Test | | X | | X |
| Chair Stand | | X | | X |
| Hand grip muscle strength | | X | | X |
| Muscle extension isokinetic leg strength (both legs, flexion, and extension) measured at one speed by Biodex | | X | | X |
| Questionnaires: SF-36 | | X | X | X |
| International Physical Activity Questionnaire (IPAQ) | X | | | |
| Exercise Tolerance Test (Maximal VO2 calculated) | X | | | |
| Submaximal Exercise Tolerance Test | | X | X | X |
| REE | | X | X | X |
| Borg Rating of Perceived Exertion Scale | | X | X | X |
| Lipid Profile (total cholesterol, triglycerides, LDL, HDL), HbA1c, and fasting insulin | | X | X | X |
| DXA | | X | | X |
| Plasma Collection for Metabolomics for acylcarnitine metabolites and muscle function biomarkers (myostatin, follistatin, cytokines and mitokines) | | X | X | X |
| Fecal Sample kits dispensed | X | | X | |
| Fecal Sample kits collected | | X | | X |
| DietMaster Pro instructions dispensed | X | X | X | |
| 3-Day Food record reviewed | | X | X | X |
| Fasting Muscle biopsy samples to measure in vivo mitochondrial gene expression | | X | | X |
| IP dispensed | | X | X | |
| IP returned | | | X | X |
| Treatment diary dispensed | | X | X | |
| Treatment diary returned | | | X | X |
| Compliance calculated | | | X | X |
| Adverse vents assessed | | | X | X |

Example 8: Phase 2 Clinical Trial—Impact of a Daily Dose of Urolithin A, on Skeletal Muscle Energetics and Function in Elderly Patients A 4 month Randomized, Double-Blind, Placebo-Controlled Phase 2 Trial is carried out to evaluate the impact of a daily dose of Urolithin A, on Skeletal Muscle Energetics and Function in Elderly comprising 60 subjects. The trial is a randomized, double-blind, single-center, placebo-controlled trial enrolling 60 healthy elderly subjects (30 placebo and 30 Urolithin A administration) who are ≥65 and ≤90 years of age with evidence of low mitochondrial function.

Study Objectives:

Primary Objective:

To evaluate the effect of an oral nutritional supplementation with Urolithin A, a food derived ingredient, compared to placebo for 4 months in healthy elderly subjects on:
  Maximum mitochondrial ATP production (ATPmax) measured via Magnetic Resonance Spectroscopy
  Muscle function measured via the single muscle fatigue test The two primary objectives will be assessed on a hand muscle (FDI—first dorsal interosseus)

Secondary Objectives

To evaluate the effect of 4 month oral administration of Urolithin A on:
  Maximum mitochondrial ATP production (ATPmax) measured via Magnetic Resonance Spectroscopy (on the Tibialis Anterior leg muscle)
  Muscle function measured via the single muscle fatigue test ((on the Tibialis Anterior leg muscle)
  Exercise Performance (Leg power, exercise efficiency, time to fatigue. Borg perceived exertion scale and VO2) measured by cycle ergometry
  Short Physical performance Battery (SPPB)
  Hand grip strength
  Leg muscle strength (via Cybex one-repetition max and ten-repetition max testing)
  6 minute walking distance (6MWD)
  Muscle size (cross-sectional area of the muscles via MRI)
  Mitochondrial function on muscle biopsy (via high resolution respirometry)
  Mitochondrial gene and protein expression in skeletal muscle tissue (microarray and protein array)
  Acylcarnitine levels in plasma (via metabolomics)
  Quality of life via SF36 questionnaire
  Plasma lipid profile (Total Cholesterol, LDL, HDL and Triglycerides)
  Plasma circulating biomarkers (myostatin, follistatin, proteomics, metabolomics)
  Safety Investigational Product, Dosage, and Mode of Administration or Intervention:
  Urolithin A provided as a softgel
  Name of the compound: Urolithin A
  Form: Softgel containing 250 mg of Urolithin A
  Dose per intake: 4 softgels a day
  Dosing's: 1000 mg Urolithin A
  Timing for intake: Repeated oral dose administration from day 1 to day 120 according to the randomization. The administration will take place in the morning with around 200 ml of tap water in sitting position and in fasting conditions of 6-8 hours.

Reference Product, Dose, and Mode of Administration or Comparative Intervention: Placebo Given as Oral Soft-Gel
  Name of the compound: Placebo
  Form: Soft gel capsule containing lecithin, triglycerides, diglycerides.
  Dose per intake: 4 softgels a day
  Timing for intake: Repeated oral dose administration from day 1 to day 120 according to the randomization. The administration will take place in the morning with around 200 ml of tap water in sitting position and in fasting conditions of 6-8 hours.
Primary Endpoints
  Percent change from baseline in ATP max in skeletal muscle (via MRS)
  Percent change from baseline in contraction number during a single muscle fatigue test
  The two primary endpoints will be assessed on the hand muscle (FDI—first dorsal interosseus)
Secondary Endpoints
  Percent change from baseline in ATP max in skeletal muscle (via MRS) (on the Tibialis Anterior leg muscle).
  Percent change from baseline in contraction number during a single muscle fatigue test (on the Tibialis Anterior leg muscle)
  Change in SPPB Scores at the end of study intervention compared to baseline
  Change in leg power output, exercise efficiency, time to fatigue, Borg perceived exertion scale and VO2 at 85% of the estimated maximum heart rate (HRmax) will be determined at the end of study intervention compared to baseline (via cycle ergometry)
  Change in hand grip strength at the end of study intervention compared to baseline
  Change in leg muscle strength (via Cybex one-repetition max and ten-repetition max testing)
  Change in 6 minute walking distance (6MWD) at the end of study intervention compared to baseline
  Change in muscle size (cross-sectional area of the muscles) before and after intervention
  Change in mitochondrial function on muscle biopsy samples at the end of study intervention compared to baseline (respirometry)
  To assess the effect of Urolithin A on mitochondrial gene and protein expression in muscle tissue before and after study intervention
  To assess the effect of Urolithin A on plasma acylcarnitine levels
  To assess the effect of Urolithin A on quality of life questionnaire (SF36)
  Change from baseline in plasma lipid profile
  Change from baseline in plasma for circulating biomarkers (myostatin, follistatin, proteomics, metabolomics)
Safety Assessments:
  Number of adverse events
  Laboratory data
  ECG
  Physical examination
  Vital Signs and temperature
  AEs will be coded according to the MedDRA
Statistical Methods:
  Primary efficacy endpoints (on the hand muscle FDI)
  Percent change from baseline in improvement in ATP max in skeletal muscle (via MRS)
  Percent change from baseline in improvement in the number of contractions in the single muscle fatigue test
  The analysis of primary efficacy parameters is done using an analysis of co-variance (ANCOVA) using the factor treatment as independent factor, the baseline measurement as covariable and the change from baseline as dependent variable. 95% confidence intervals for treatment differences and corresponding non-adjusted p-values will be calculated.
  A 5% significance level will be applied for the comparison of the Urolithin A dose versus Placebo.
  In order to account for the two primary efficacy endpoints, a priori-ordered hypothesis are stated, i.e. percent number of contractions will only be tested for confirmatory decisions if change in ATPmax resulted in a statistical significant difference in Urolithin A dose compared to Placebo. If the Urolithin A dose resulted in a significant result for ATPmax, the testing procedure continues for testing muscle endurance in the muscle fatigue test.
  This trial is powered to detect a difference in change from baseline in ATPmax between treatment groups.
  Previous studies in endurance training in subjects aged >65 to <90 years suggest a change in ATPmax can be achieved over a 6 month time period of 0.103 under treatment and −0.03 under Placebo. Based on a clinical relevant difference of 0.133 and a standard deviation of 0.149 under treatment and 0.154 under Placebo this results in a sample size of 27 per group using a 5% two-sided significance level and 88% power.
  Assuming a 10% drop-out rate, 30 subjects per group will be enrolled (60 subjects in total)

The invention claimed is:

1. A method of improving mitochondrial function or muscle function or muscle performance, comprising orally administering to a human in need thereof urolithin A or a salt thereof;
  wherein the urolithin A or a salt thereof is administered at 1000 mg/day, over a period of 28 days; and the urolithin A or salt thereof is administered in the form of a soft gel capsule which further comprises lecithin, medium chain triglycerides (MCT), and glycerol monostearate.

2. The method of claim 1, wherein the urolithin A or salt thereof is administered once per day.

3. The method of claim 1, wherein the urolithin A or salt thereof is administered twice per day.

4. The method of claim 1, wherein mitochondrial function is improved.

5. The method of claim 1, wherein muscle function or muscle performance is improved.

6. The method of claim 4, wherein the urolithin A or salt thereof is administered once per day.

7. The method of claim 4, wherein the urolithin A or salt thereof is administered twice per day.

8. The method of claim 5, wherein the urolithin A or salt thereof is administered once per day.

9. The method of claim 5, wherein the urolithin A or salt thereof is administered twice per day.

10. A method of improving mitochondrial function or muscle function or muscle performance, comprising orally administering to a human in need thereof urolithin A or a salt thereof;
  wherein the urolithin A or a salt thereof is administered at 1000 mg/day, over a period of 28 days; the urolithin A or salt thereof is administered in the form of a soft gel capsule which further comprises lecithin, medium chain triglycerides (MCT), and glycerol monostearate; and the human is elderly.

11. The method of claim 10, wherein the urolithin A or salt thereof is administered as a dietary, nutritional or health supplement.

12. The method of claim 10, wherein the urolithin A or salt thereof is administered once per day.

13. The method of claim 10, wherein the urolithin A or salt thereof is administered twice per day.

14. The method of claim 10, wherein mitochondrial function is improved.

15. The method of claim 10, wherein muscle function or muscle performance is improved.

16. The method of claim 14, wherein the urolithin A or salt thereof is administered once per day.

17. The method of claim 14, wherein the urolithin A or salt thereof is administered twice per day.

18. The method of claim 15, wherein the urolithin A or salt thereof is administered once per day.

19. The method of claim 15, wherein the urolithin A or salt thereof is administered twice per day.

\* \* \* \* \*